(12) United States Patent
Joubert et al.

(10) Patent No.: US 11,278,627 B2
(45) Date of Patent: Mar. 22, 2022

(54) ANTIBODY-DRUG CONJUGATES AND THE USE OF SAME IN THERAPY

(71) Applicant: McSAF, Tours (FR)

(72) Inventors: Nicolas Joubert, Saint Avertin (FR); Marie Claude Viaud-Massuard, Tours (FR); Renaud Respaud, Tours (FR)

(73) Assignee: MC SAF, Tours (FR)

( * ) Notice: Subject to any disclaimer, the term of this patent is extended or adjusted under 35 U.S.C. 154(b) by 6 days.

(21) Appl. No.: 16/381,803

(22) Filed: Apr. 11, 2019

(65) Prior Publication Data

US 2019/0365914 A1  Dec. 5, 2019

Related U.S. Application Data

(62) Division of application No. 14/904,353, filed as application No. PCT/FR2014/051802 on Jul. 11, 2014, now Pat. No. 10,307,488.

(30) Foreign Application Priority Data

Jul. 11, 2013  (FR) ..................................... 1356837

(51) Int. Cl.
| A61K 47/65 | (2017.01) |
| A61K 47/68 | (2017.01) |
| A61K 49/00 | (2006.01) |
| A61K 51/02 | (2006.01) |
| C07D 207/456 | (2006.01) |
| C07K 16/32 | (2006.01) |
| C07K 16/28 | (2006.01) |
| C07K 16/40 | (2006.01) |
| C12N 9/10 | (2006.01) |
| C12N 9/24 | (2006.01) |

(52) U.S. Cl.
CPC .......... *A61K 47/65* (2017.08); *A61K 47/6849* (2017.08); *A61K 47/6871* (2017.08); *A61K 47/6889* (2017.08); *A61K 49/00* (2013.01); *A61K 51/02* (2013.01); *C07D 207/456* (2013.01); *C07K 16/2887* (2013.01); *C07K 16/32* (2013.01); *C07K 16/40* (2013.01); *C12N 9/1077* (2013.01); *C12N 9/24* (2013.01); *C12N 9/2497* (2013.01); *C12Y 204/02036* (2013.01); *C12Y 302/00* (2013.01); *C12Y 302/02022* (2013.01)

(58) Field of Classification Search
CPC .... A61K 47/00; A61K 47/65; A61K 47/6889; A61K 47/6849; A61K 47/6871; A61K 49/00; A61K 51/00; A61K 51/02; C07K 16/2887; C07K 16/40; C07K 16/32; C12N 9/1077; C12N 9/24; C12N 9/2497; C07D 207/456; C12Y 204/02036; C12Y 302/00; C12Y 302/02022; A61P 7/04; A61P 37/06; A61P 37/02; A61P 37/00; A61P 35/02; A61P 35/00; A61P 29/00; A61P 19/02; A61P 17/06; A61P 1/04
USPC .......... 424/1.11, 1.49, 1.65, 1.69, 1.81, 1.85, 424/1.89, 9.1, 9.2, 9.6; 514/1, 1.1, 19.2, 514/19.3, 19.4, 19.5, 19.6; 534/7, 10–16; 530/300
See application file for complete search history.

(56) References Cited

U.S. PATENT DOCUMENTS

| 10,307,488 B2 * | 6/2019 | Joubert .............. A61K 47/6871 |
| 2010/0260786 A1 | 10/2010 | Doronina et al. |
| 2013/0224228 A1 | 8/2013 | Jackson et al. |

FOREIGN PATENT DOCUMENTS

| CH | 617320 A5 | 5/1980 |
| CN | 101490087 A | 7/2009 |
| DE | 19843873 A1 | 3/2000 |
| EP | 0319712 A1 | 6/1989 |
| JP | 2009-517467 A | 4/2009 |
| WO | 2007/064345 A2 | 6/2007 |
| WO | 2007/140371 A2 | 12/2007 |
| WO | 2012/153193 A2 | 11/2012 |
| WO | 2013/132268 A1 | 3/2013 |
| WO | 2013/085925 A1 | 6/2013 |

OTHER PUBLICATIONS

FR Search Report, dated Mar. 31, 2014, from corresponding FR application No. 1356837.
Ducry, "Linker technologies for Antibody-Drug Conjugates," Antibody-drug conjugates, Jan. 1, 2013, pp. 71-100, vol. 1045.
Kalgutkar et al., "Design, Synthesis and Biochemical Evaluation of N-Substituted Maleimides as Inhibitors of Prostaglandin Endoperoxide Synthases," J. Med. Chem., 1986, pp. 1692-1703, vol. 39.
Ochi et al., "Supramolecular hydrogels based on bola-amphiphilic glycolipids showing color change in response to glycosidases," Chemical Communications, Dec. 24, 2012, pp. 2115-2117, vol. 48, No. 21.
Ryan et al., "Tunable reagents for multi-functional bioconjugation: reversible or permanent chemical modification of proteins and peptides by control of malemide hydrolysis," Chemical Communications, Jan. 1, 2011, p. 5452, vol. 47, No. 19.

(Continued)

*Primary Examiner* — D. L. Jones
(74) *Attorney, Agent, or Firm* — MH2 Technology Law Group LLP

(57) ABSTRACT

Disclosed are novel antibody-drug conjugates and use thereof in therapy, in particular in anticancer or anti-inflammatory therapy, as well as synthetic products useful as linkers, composed of a linker head and a linker body, and also a method for preparing the linkers and the antibody-drug conjugates.

25 Claims, 15 Drawing Sheets
(10 of 15 Drawing Sheet(s) Filed in Color)

(56) References Cited

OTHER PUBLICATIONS

Schumacher et al., "Homogeneous antibody fragment conjugation by disulfide bridging introduces spinostics," Scientific Reports, Mar. 22, 2013, vol. 3.

Shcerbakov et al., "Organotin Derivatives of Certain N-(2,2'-Dichloromaleoyl)-Protected Aminoacids and Dipeptides," Organomettalic Chemistry in the USSR, vol. 5, No. 3, Jan. 1, 1992, pp. 305-310.

Smith et al., "Protein modification biconjugation, and disulfide bridging using bromomaleimides," Journal of the American Chemical Society, vol. 132, No. 6, Feb. 17, 2010, pp. 1960-1965.

* cited by examiner

|  | MEASUREMENT OF MASS (MAX) | CALCULATION DAR4 | AVERAGE DEGREE OF GRAFTING |
|---|---|---|---|
| IgG1 | 148209 | | |
| NJ177 | 149695 | 149685 | 4,0 |

FIG. 3

| CENTRO 0 | CENTRO 1 | CENTRO 2 | CENTRO 3 | CENTRO 4 | CENTRO 5 | CENTRO 6,7,8 |
|---|---|---|---|---|---|---|
| 8% | 0% | 0% | 3% | 89% | | |

FIG. 4

ANTIBODY-DRUG CONJUGATES AND THE USE OF SAME IN THERAPY

FIELD OF INVENTION

The present invention relates to novel antibody-drug conjugates and use thereof in therapy, in particular in anticancer or anti-inflammatory therapy. The present invention also relates to synthetic products useful as linkers, composed of a linker head and a linker body. The present invention also relates to a method for preparing the linkers and the antibody-drug conjugates.

BACKGROUND OF THE INVENTION

An antibody-drug conjugate is a new form of drug, in particular used as an anticancer agent with targeted action. The therapeutic antibody binds to one or more cell types as a $function$ of its specificity and conventionally releases a cytotoxic agent in the cells.

An antibody-drug conjugate constitutes a means for selective delivery of a cytotoxic agent. This engineering therefore makes it possible to combine the specificity of targeting by antibodies with powerful new effector functions by the agents with which they are conjugated.

To date, more than 20 antibody-drug conjugates are under development (Senter, P. D. et al. *Annu. Rev. Med.* 2013, 64, 15-29).

The general structure of an antibody-drug conjugate is as described in FIG. 1.

The product linking the antibody and the drug is called a linking agent or linker. It can be grafted onto the antibody via at least one of the eight cysteines forming the 4 interchain disulphide bridges or onto at least one of the eight lysines.

The number of drug molecules grafted onto the antibody determines a ratio called the Drug-Antibody Ratio (DAR).

After binding to its target antigen, the antibody is internalized in the cell by receptor-mediated endocytosis. The vesicles fuse with lysosomes where the cytotoxic molecule is released from the antibody by various mechanisms. The active cytotoxic agent then acts directly on the cell, inducing its death, and sometimes on the neighbouring cancer cells by transport or diffusion in the environment.

The antibody is therefore used mainly as a vector and delivers the cytotoxic agent into the cell.

By "cytotoxic agent" is meant a molecule capable of inhibiting or preventing the function of a cell.

The cytotoxic agent bound to the antibody is a prodrug that becomes active in the tumour cell after release (Jaracz et al. 2005). The activity of the free molecule must be sufficient to kill the cancer cell, even at low concentration.

Despite their growing success, antibody-drug conjugates have a notable drawback, because they are more complex and have a heterogeneous structure compared to the corresponding original antibody. Attachment of a cytotoxic agent via a linker has a significant influence on the pharmacokinetics and pharmacodynamics of the antibody (PK-PD) and therefore on the therapeutic index.

The antibody-drug conjugates preferably have an average DAR equal to 4 for optimum activity but this ratio can vary from 1 to 13, knowing that for a DAR there can be a population of distinct entities.

Many researchers are working on this heterogeneity. Tests have been carried out with the aim of modifying the sequence of the antibody, by introducing natural or non-natural amino acids (Mallet, W. et al. Nat. Biotechnol. 2008, 26, 925-932 and Schultz, P. G. et al. Proc. Natl. Acad. Sci. 2012, 109, 16101-16106). Nevertheless, this method has a disadvantage, that of having to be transposed for each antibody of interest, which requires consistent work on the starting antibody.

Consequently, the technical problem that arises from the prior art is to obtain a technological means allowing controlled grafting of a cytotoxic agent without modifying the sequence of the antibody of interest—a technological means that can be adapted to any antibody.

SUMMARY OF THE INVENTION

One aspect of the invention is a synthetic product useful as a linker head.

Another aspect of the invention is a product defined as a linker head, bound to an element L representing a linker body.

Another aspect of the invention is a linker bound to an element M defined as a cytotoxic drug.

Another aspect of the invention is a linker associated with a cytotoxic drug and associated with a protein, which can in particular be an antibody or an antibody fragment.

The present invention is mainly based on a product that is characterized in that it corresponds to formula I selected from formulae IB and IA:

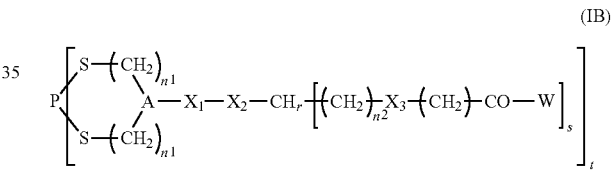

(IB)

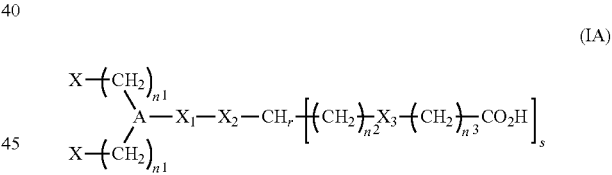

(IA)

in which:

X is a halogen, or a nucleofuge, or a

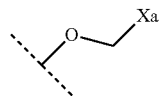

group, or a

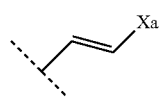

group, $X_a$ being a halogen or a nucleofuge.

A represents either an aryl or cycloalkyl radical, said aryl or cycloalkyl radicals being carbocyclic or heterocyclic,
or A represents
a

group, a

group or a

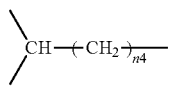

group
$X_1$ is a C=O or a single bond
$X_2$ is an NH group or a single bond
$X_3$ is an oxygen or a single bond
s is equal to 1, 2 or 3
r is equal to 0, 1 or 2
it being understood that the sum r+s is equal to 3
$n_1$ is an integer equal to 0, 1, 2 or 3; $n_2$ is an integer equal to 1, 2 or 3 and $n_3$ is an integer equal to 1, 2 or 3,
W represents
an —OH radical,
an -L radical which represents a linker body comprising a terminal reactive function,
an —FL fluorophore group used in diagnostics or analysis, involving detection of fluorescence preferably selected from rhodamine or a derivative thereof, preferably rhodamine B, fluorescein isothiocyanate (FITC), a Cy dye preferably selected from Cy5, Cy5.5, Cy7, an Alexa fluor dye preferably selected from Alexa Fluor 647, 700 or 750, Texas Red, allophycocyanin (APC) and conjugates thereof with other fluorochromes in particular those mentioned above, phycoerythrin (PE) and conjugates thereof with other fluorochromes in particular those mentioned above,
an R* radioactive radical, which preferably contains
either a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA;
or a bifunctional ligand preferably selected from one of the acyclic chelating agents from the list constituted by EDTA, CyEDTA, EDTMP, DTPMP, DTPA, CyDTPA, Cy$_2$DTPA, DTPA-MA, DTPA-BA, BOPA;
or a bifunctional ligand preferably selected from one of the macrocyclic chelating agents from the list constituted by DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA;
or a bifunctional chelating agent of the cationic, anionic, neutral or cleavable type;
or a radionuclide preferably selected from $^{67}$Cu, $^{64}$Cu, $^{90}$Y, $^{109}$Pd, $^{111}$Ag, $^{149}$Pm, $^{153}$Sm, $^{166}$Ho, $^{177}$Lu, $^{186}$Re, $^{188}$Re, $^{99m}$Tc, $^{67}$Ga, $^{68}$Ga, $^{111}$In, $^{90}$Y, $^{177}$Lu, $^{186}$Re, $^{188}$Re, $^{197}$Au, $^{198}$Au, $^{199}$Au, $^{105}$Rh, $^{165}$Ho, $^{166}$Ho, $^{161}$Tb, $^{149}$Pm, $^{44}$Sc, $^{47}$Sc, $^{70}$As, $^{71}$As, $^{72}$As, $^{73}$As, $^{74}$As, $^{76}$As, $^{77}$As, $^{212}$Pb, $^{212}$Bi, $^{213}$Bi, $^{225}$Ac, $^{117m}$Sn, $^{67}$Ga, $^{201}$Tl, $^{121}$I, $^{131}$I, $^{160}$Gd, $^{148}$Nd, $^{89}$Sr, $^{211}$At,
an -L-M radical in which L has the meaning given above and M represents a cytotoxic drug selected from a chemotherapeutic agent or a toxin,
P is a protein comprising at least one disulphide bridge and t represents an integer from 1 to 15, preferably from 1 to 6 and 13
as well as the derivatives of the carboxylic acid function or functions such as the salts, esters or amides, preferably the amide formed with butanimide.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The conventional modification sites are as follows:
4 lysines
Average of 4 residues modified among the 8 residues accessible for modification from among 80, consequently numerous DAR species.
4 disulphide bridges
After reduction with TCEP (tris(2-carboxyethyl)phosphine), 8 cysteine residues accessible, consequently numerous species with DAR from 0 to 8.
DAR=drug-antibody ratio (or drug-to-antibody ratio).
The average DAR is approximately 4 with conventional modifications.

Figure 1:
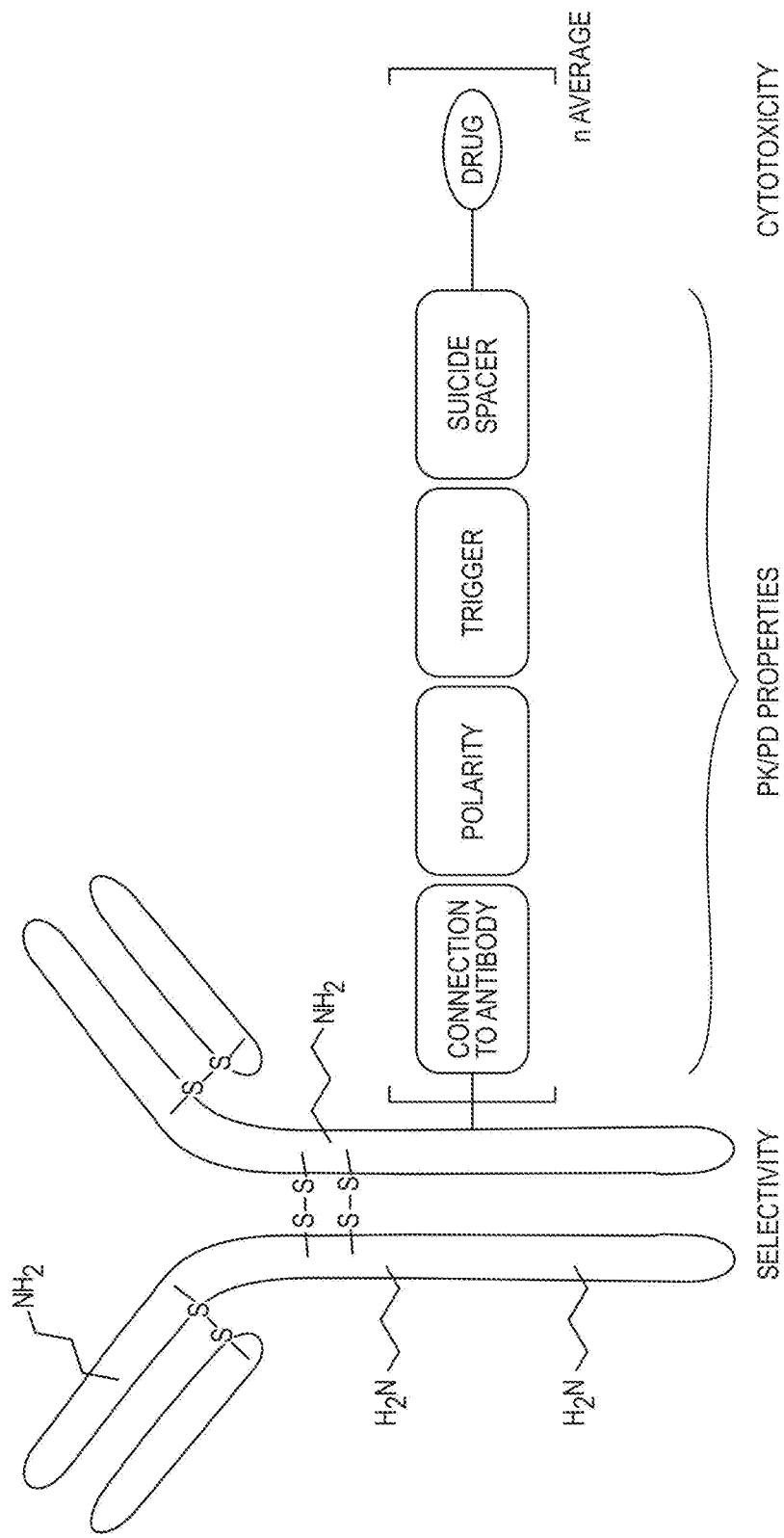
FIG. 1 presents the general structure of an antibody-drug conjugate.
Figure 2:
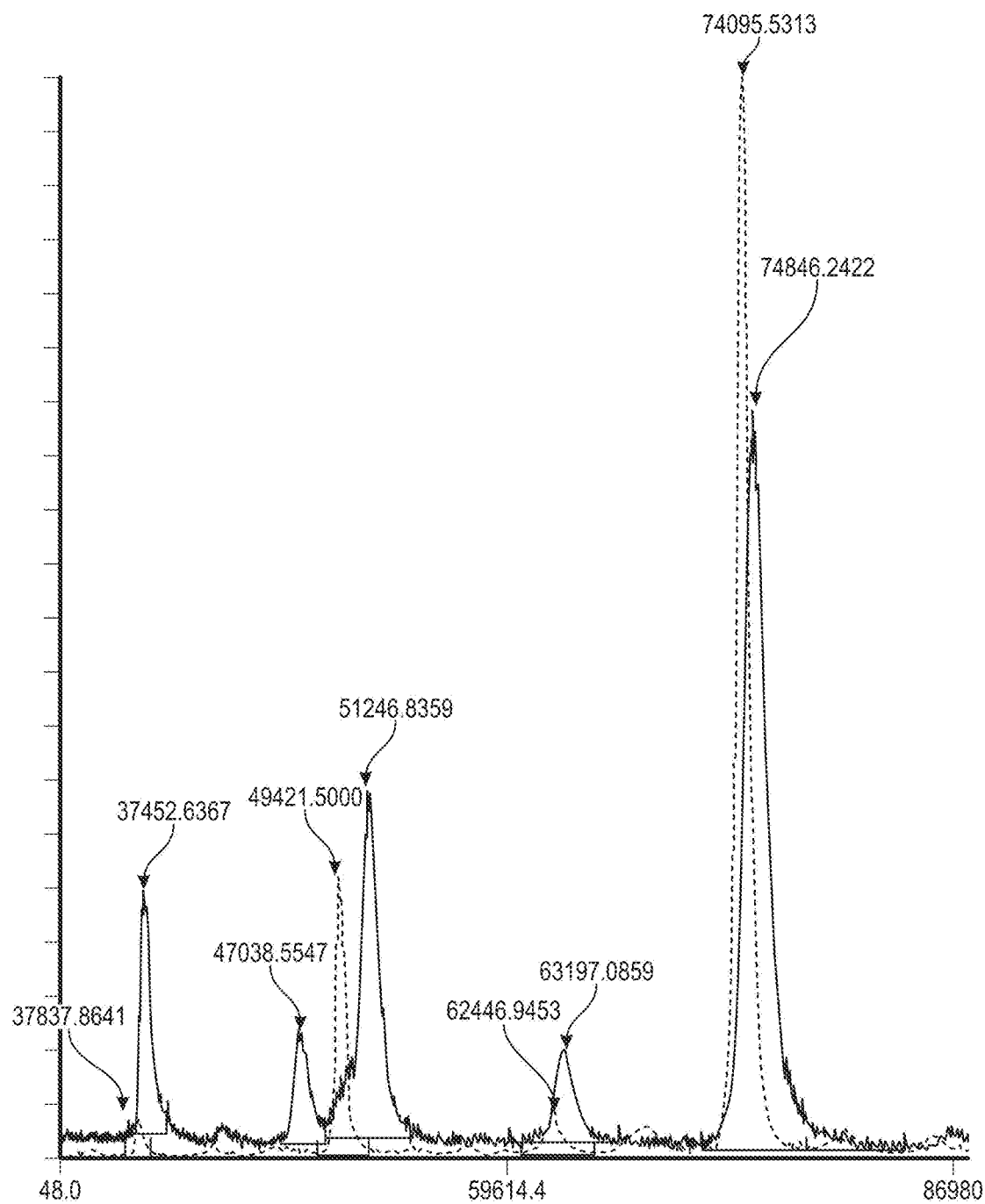

FIG. 2 presents the MALDI-TOF mass spectrometry analysis of trastuzumab (peak at 74095 and peaks indicated by the dotted arrows) and of grafted trastuzumab reconstructed by the linker (spacer) 6-(3,4-dibromomaleimido) hexanoic acid (peak at 74846 and peaks indicated by the solid arrows).

Figure 5:
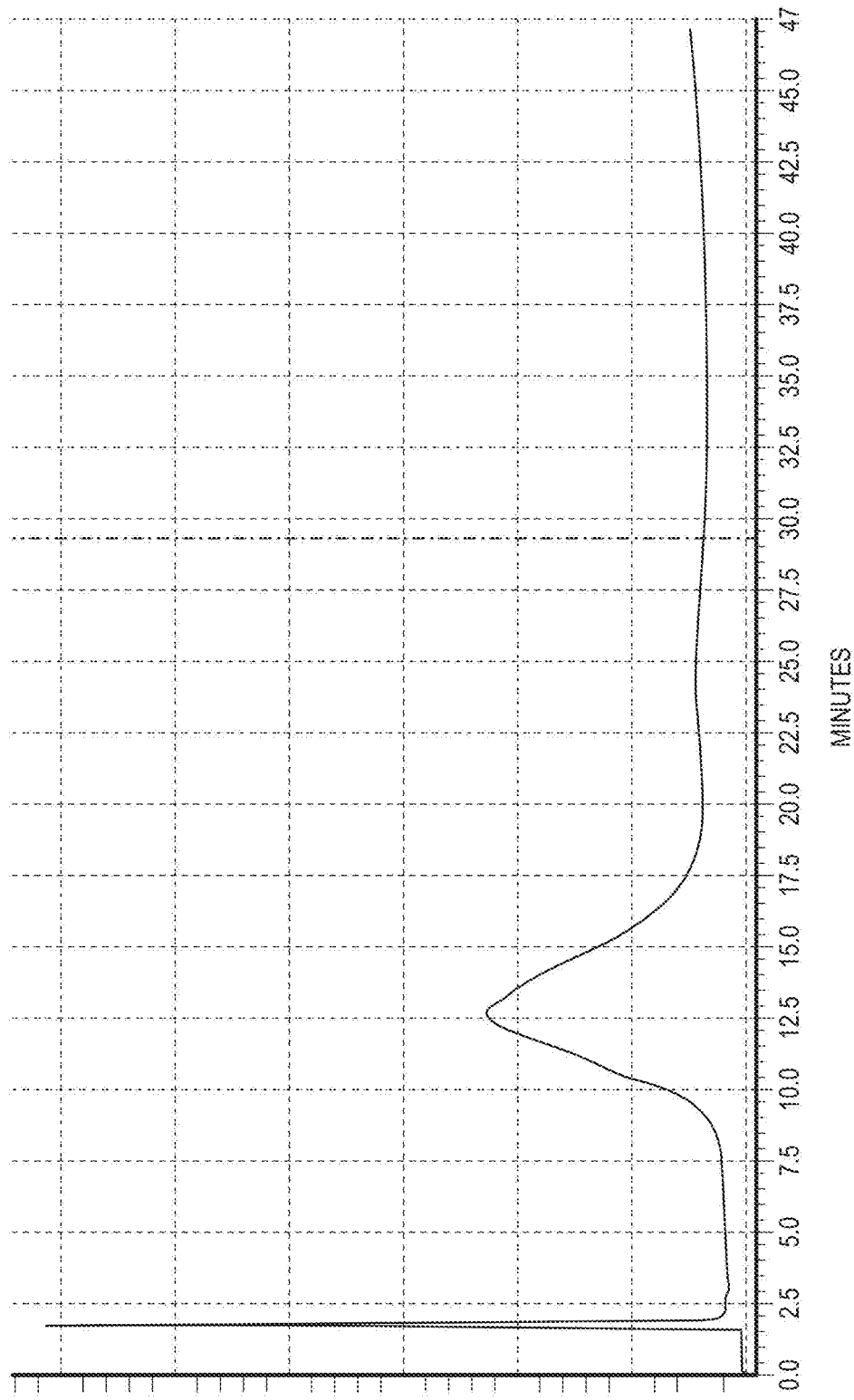

FIG. 3 presents that this analysis is able to confirm that the reaction mixture (peak at 74095) contains 89% of the species resulting from grafting 4 linkers of 6-(3,4-dibromomaleimido)hexanoic acid on the antibody, the grafting average being 4.0:

FIG. 4 presents the calculation of the distribution of the different species by deconvolution of the main peak (peak at 74846):

FIG. 5 presents the HIC-HPLC chromatogram of the trastuzumab antibody 24 purified and reconstructed after reduction by TCEP and then addition of the linker 6-(3,4-dibromomaleimido)hexanamide-Val-Cit-PAB-OH.

A small quantity of DAR=0 remains (confirmation of the MALDI-TOF results) and DAR=4 is the main species.

Figure 6A:
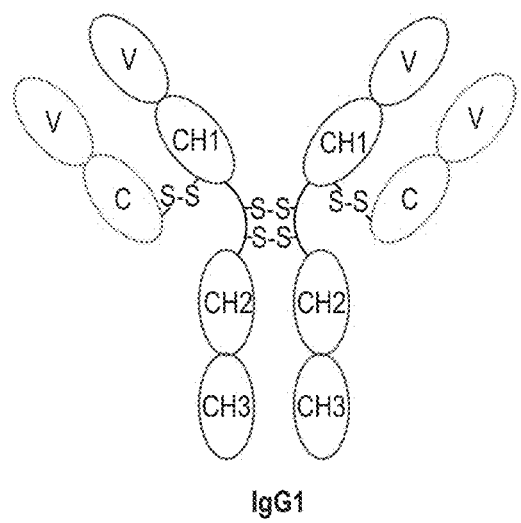
Figure 6B:
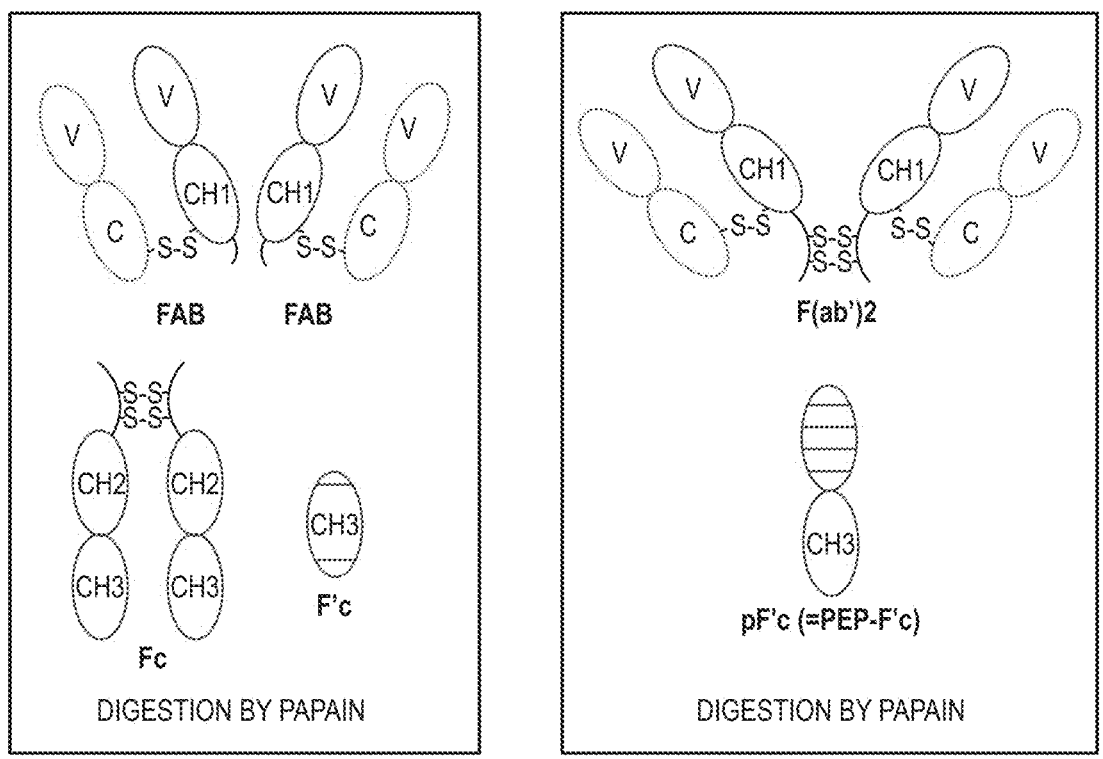
Figure 6C:
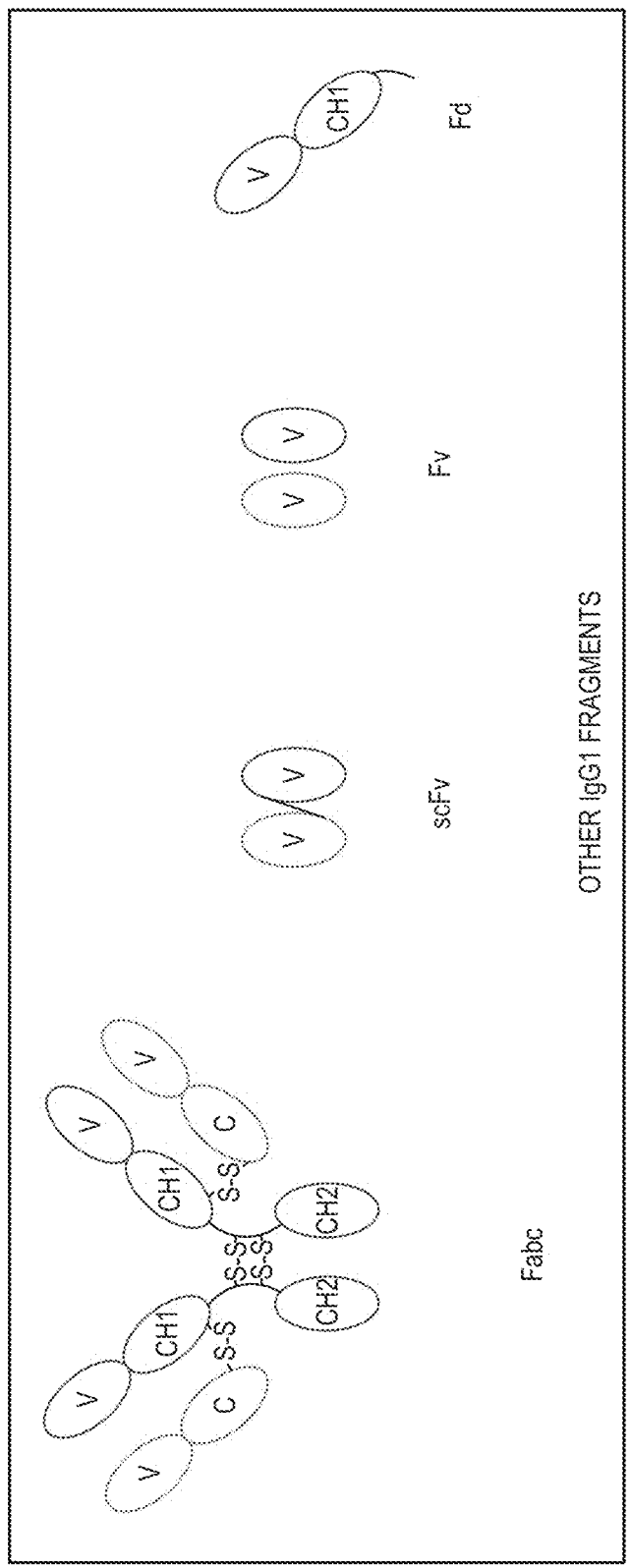

FIGS. 6A to 6C present the nomenclature of the different antibody fractions. FIG. 6A presents the Ig1 fragments obtained after digestion with papain (Fc and F'c) or pepsin (Fc'=pepF'c).

FIG. 6B presents the Fabc, Fd, Fv and scFv fragments.

FIG. 6C presents the structure of the chimeric and humanized antibodies.

Figure 7:
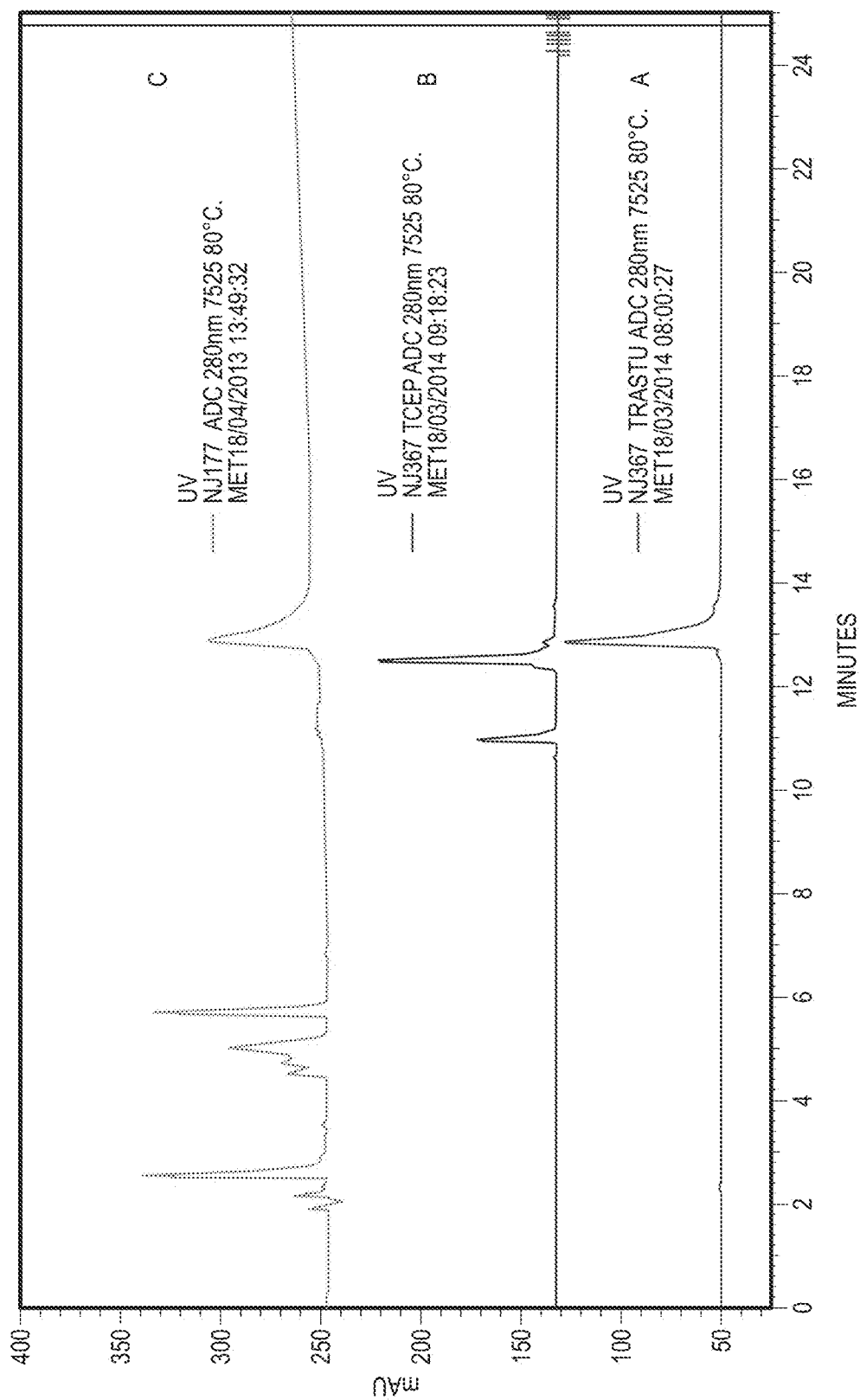

FIG. 7 presents the RP-HPLC chromatogram of the trastuzumab-(maldiBr-linker7) 4 antibody 24 obtained in example 5.2.

A: trastuzumab.

B: antibody reduced by TCEP: the heavy and light chains of trastuzumab are separated due to the denaturing nature of RP-HPLC analysis.

C: reconstructed trastuzumab 24 (crude reaction mixture): a single peak is observed, proof that the bridges between the chains have been reconstructed by the linker 7 6-(3,4-dibromomaleimido)hexanoic acid.

The peaks where the retention times are less than 10 minutes represent the linker residues.

Figure 8:
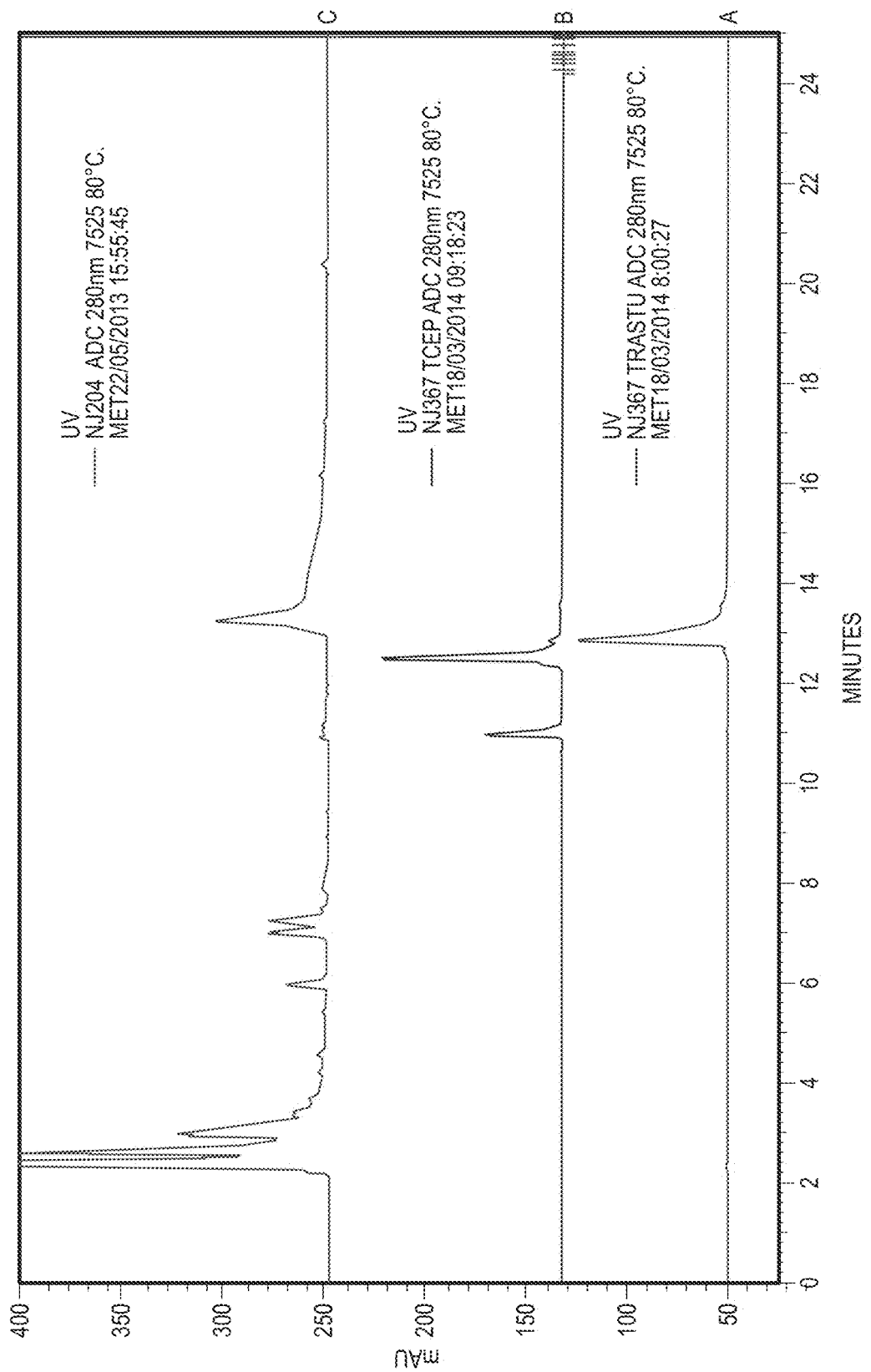

FIG. 8 presents the RP-HPLC analysis of trastuzumab-(maldiBr-linker8)4 25 obtained in example 5.3.

A: native trastuzumab.

B: trastuzumab reduced by TCEP.

C: trastuzumab 25 reconstructed by the linker 8 6-(3,4-dibromomaleimido)hexanamide-Val-Cit-PAB-OH.

Figure 9:
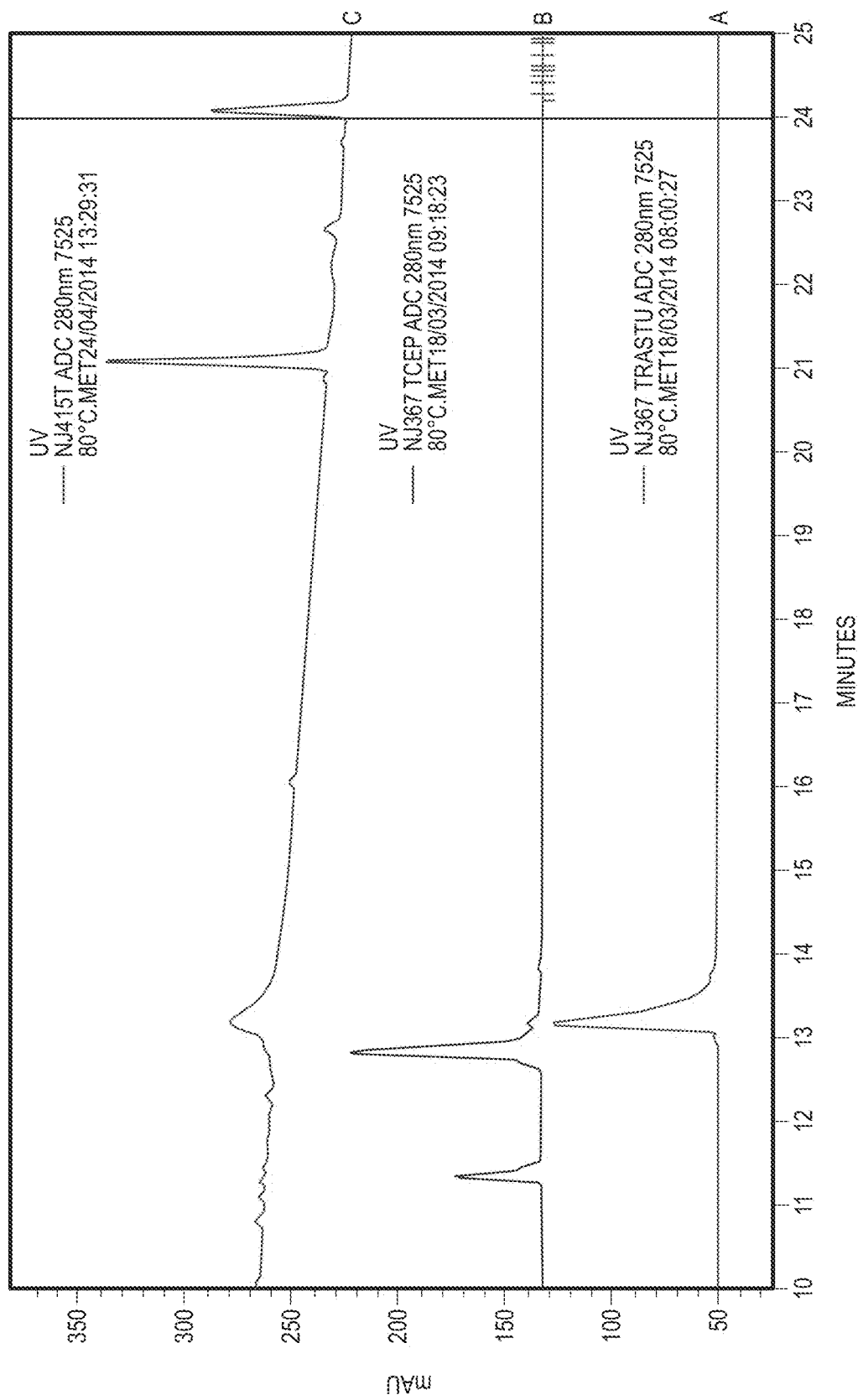

FIG. 9 presents the RP-HPLC analysis of trastuzumab-(maldiSPh-linker26)4 27 obtained in example 5.4.

A: native trastuzumab.

B: trastuzumab reduced by TCEP.

C: trastuzumab 27 reconstructed by the linker 26 6-(3,4-dithiophenylmaleimido)hexanamide-Val-Cit-PAB-OH.

Figure 10:
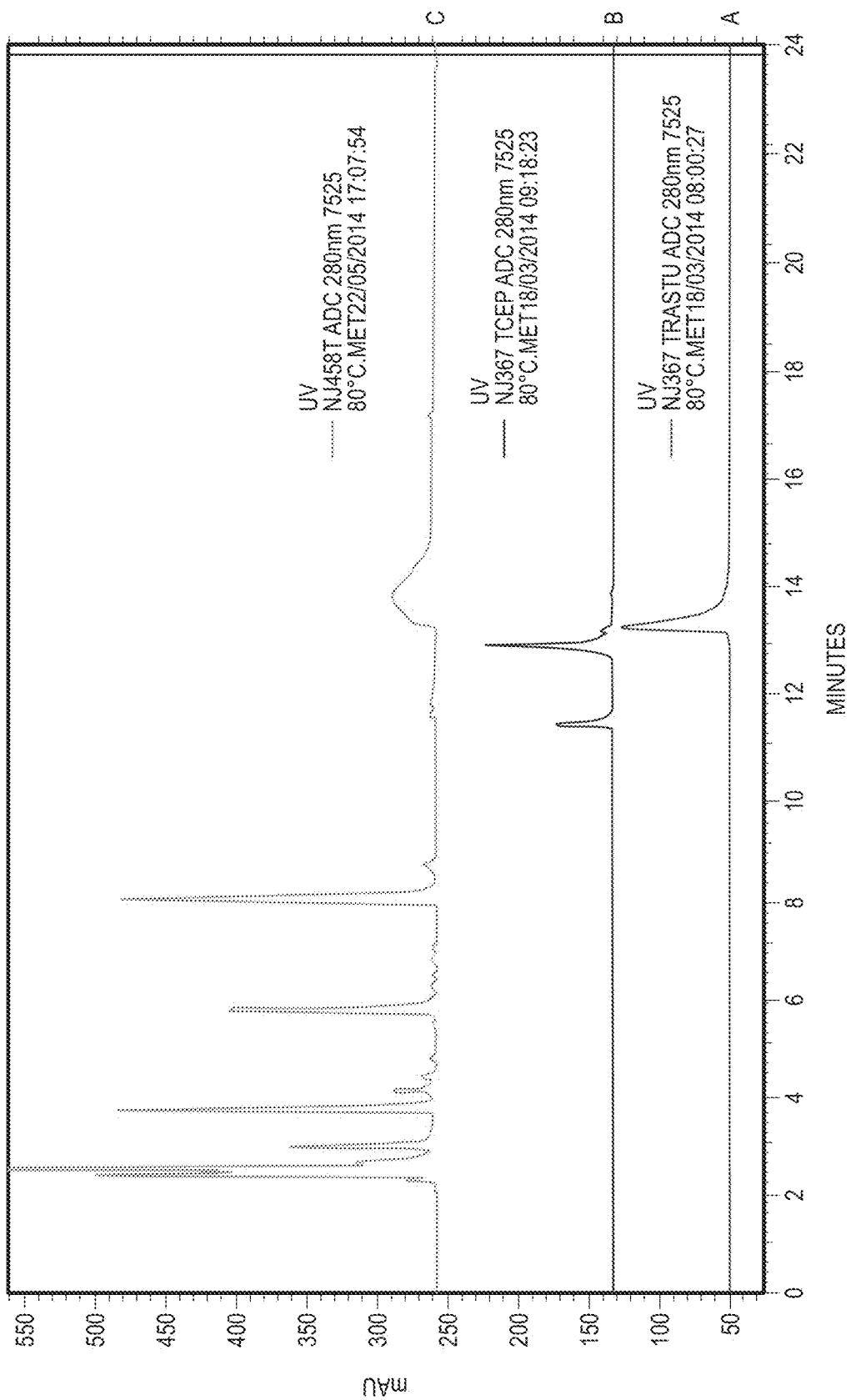

FIG. 10 presents the RP-HPLC analysis of trastuzumab-(PydiMediBr-linker20)4 28 obtained in example 5.5.

A: native trastuzumab.

B: trastuzumab reduced by TCEP.

C: trastuzumab 28 by the linker 20 6-(2,6-bis(bromomethyl)isonicotinamido) hexanoic acid.

Figure 11:
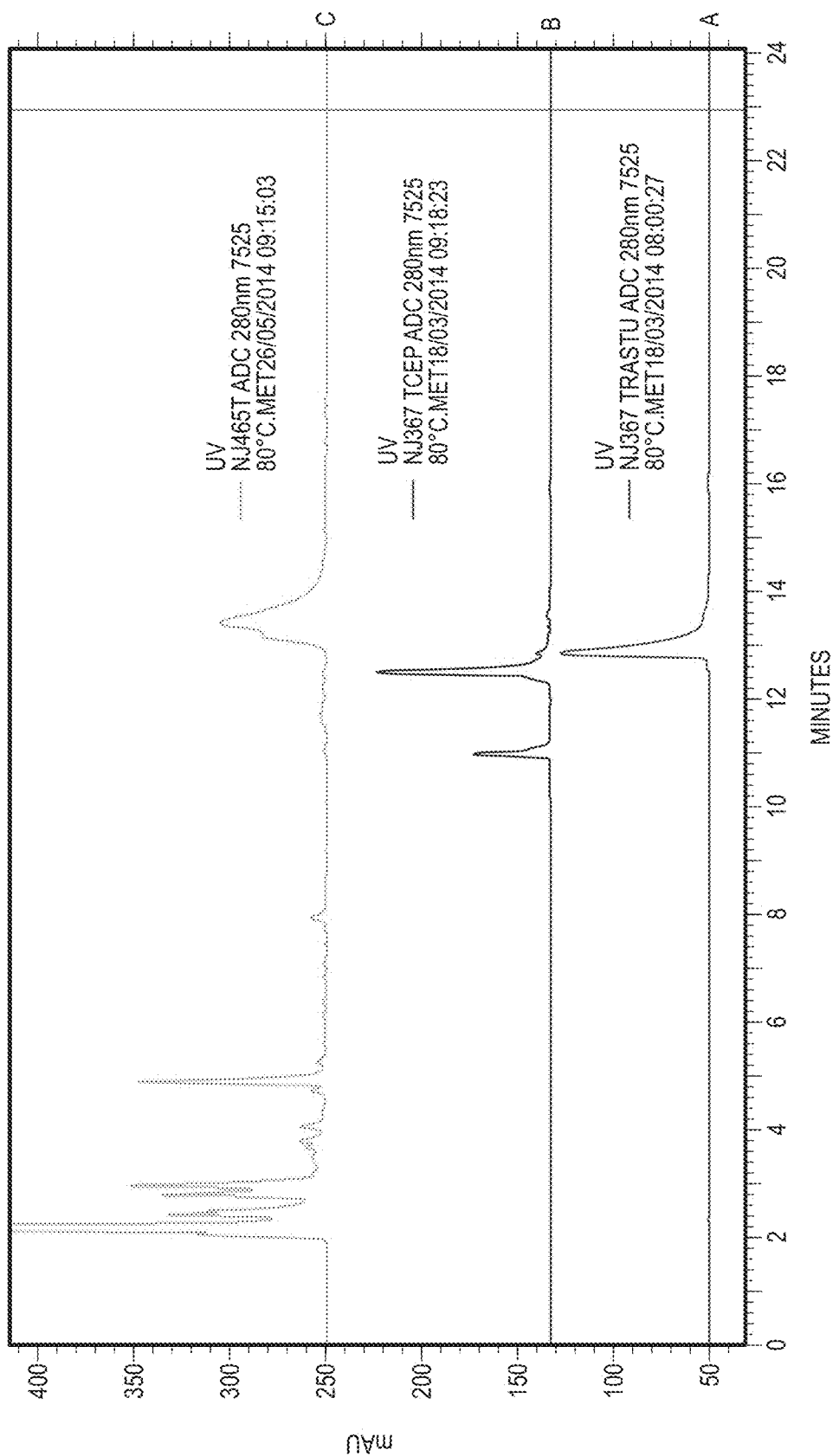

FIG. 11 presents the RP-HPLC analysis of trastuzumab-(PydiMediBr-linker22)4 29 obtained in example 5.6.

A: native trastuzumab.

B: trastuzumab reduced by TCEP.

C: trastuzumab 29 by the acid linker 22 6-(2,6-bis(bromomethyl)isonicotinamido)hexanamide-Val-Cit-PAB-OH.

Figure 12:
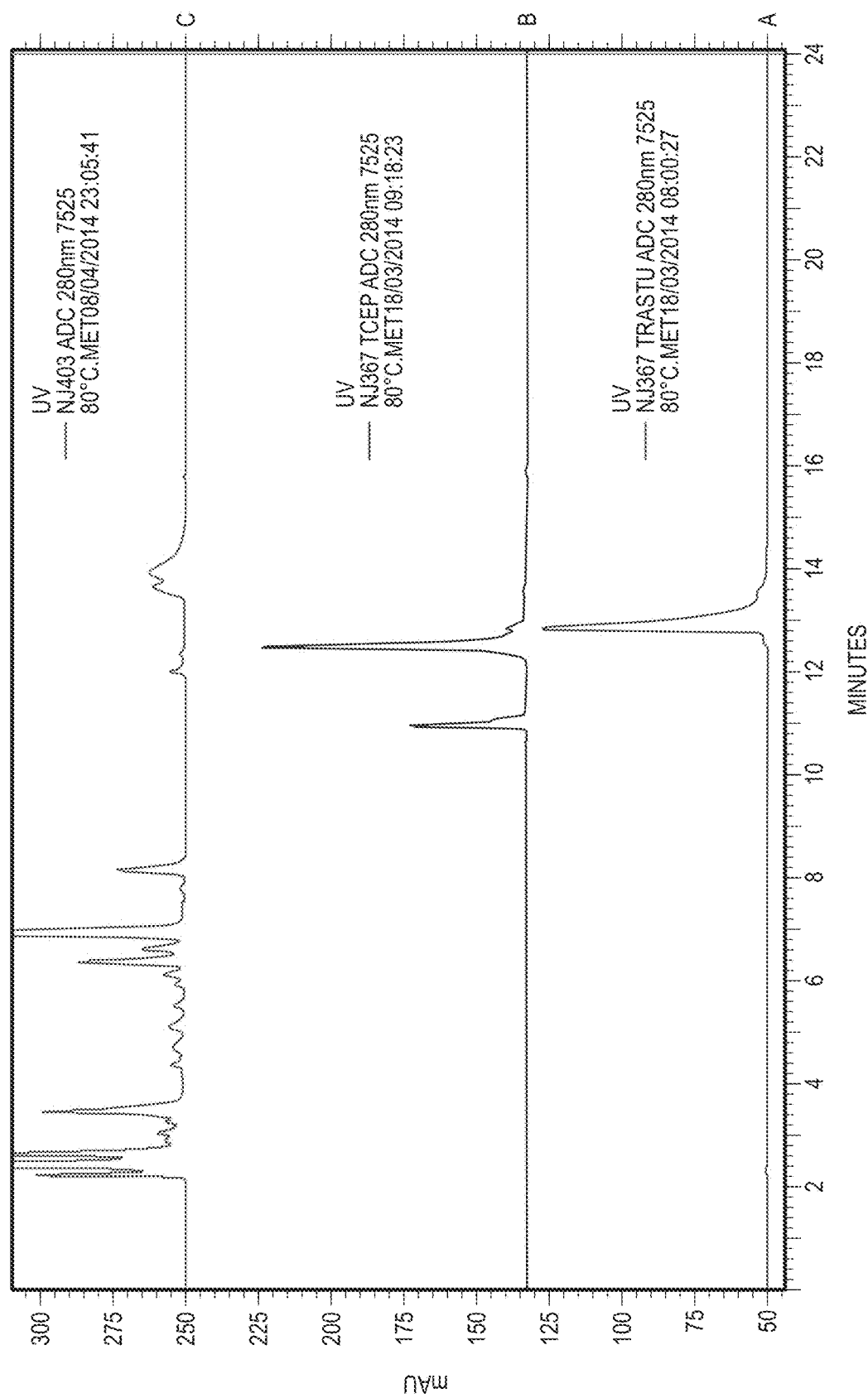

FIG. 12 presents the RP-HPLC analysis of trastuzumab-(PhdiMediBr-linker15)4 30 obtained in example 5.7.

A: native trastuzumab.

B: trastuzumab reduced by TCEP.

C: Trastuzumab 30 partially reconstructed by the acid linker 15 6-(2,6-bis(bromomethyl)benzamido)hexanamide-Val-Cit-PAB-OH.

Figure 13:
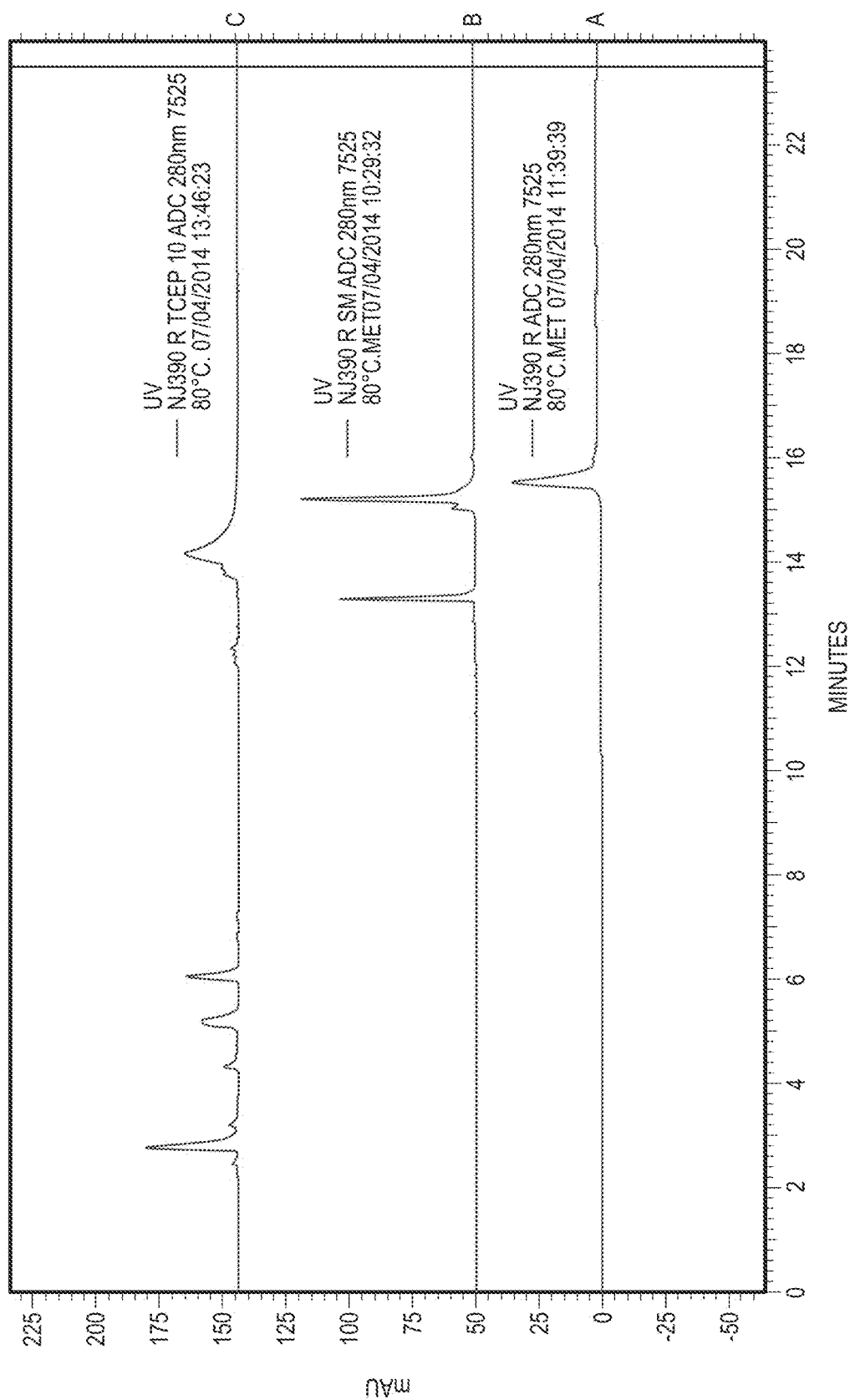

FIG. 13 presents the RP-HPLC analysis of rituximab-(maldiBr-linker7)4 31 obtained in example 5.8.

A: native rituximab.

B: rituximab reduced by TCEP.

C: rituximab 31 reconstructed by the linker 7 6-(3,4-dibromomaleimido) hexanoic acid.

Figure 14:
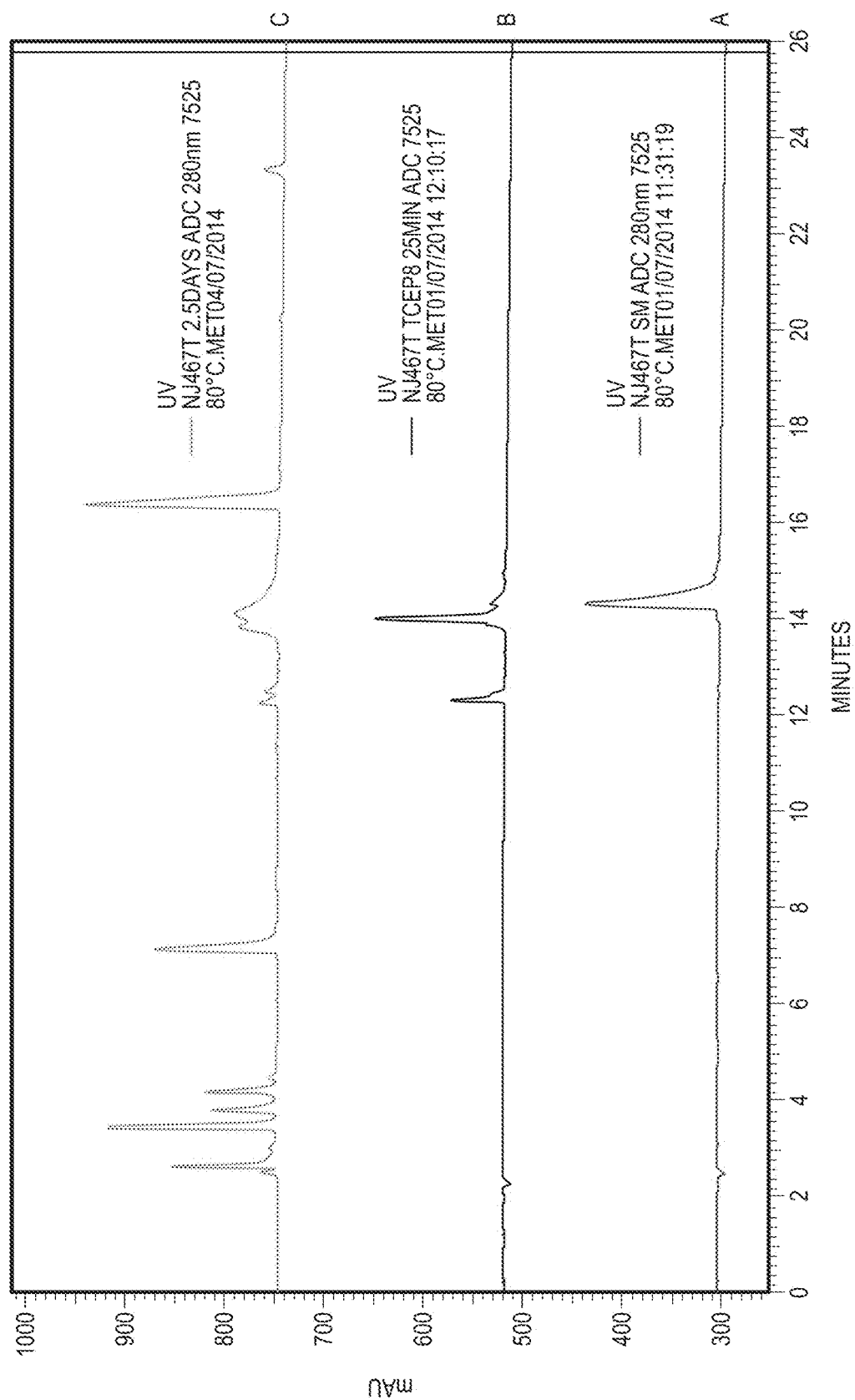

FIG. 14 presents the RP-HPLC analysis of trastuzumab-(maldiBr-linker9-MMAE)4 32 obtained in example 5.9.

A: native trastuzumab.

B: trastuzumab reduced by TCEP.

C: trastuzumab 32 reconstructed by the linker 9-MMAE 6-(3,4-dibromomaleimido)hexanamide-Val-Cit-PAB-MMAE.

Figure 15:
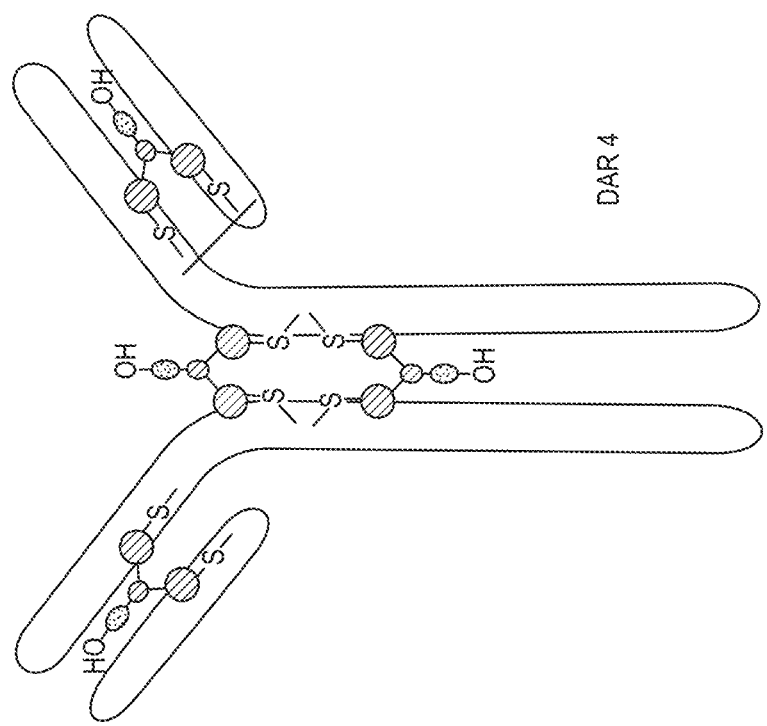
Figure 15:
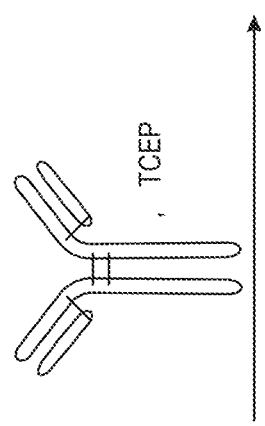
Figure 15:
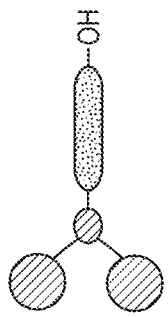

FIG. 15 illustrates the general procedure 4 for bioconjugation as described in Example 5.

DETAILED DESCRIPTION OF THE INVENTION

Within the meaning of the present invention, by "nucleofuge" is meant any ion or substituent that is able to break away from a molecule.

The carbocyclic or heterocyclic aryl radical that A can represent is preferably selected from the phenyl, naphthyl, pyridyl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, pyrrolyl, isothiazolyl radicals, and which is optionally substituted with one or more $C_1$ to $C_6$ alkyl, $C_1$ to $C_6$ alkoxy, halogen, amino or oxo groups, the preferred radical being dioxo-pyrrolyl.

The carbocyclic or heterocyclic cycloalkyl radical that A can represent is preferably selected from the cyclopropyl, cyclobutyl, cyclopentyl, or cyclohexyl radicals or a heterocyclic cycloalkyl, which can be monocyclic or condensed, for example pyrrolidinyl, piperidinyl, piperazinyl, morpholinyl, or thiazinyl.

The halogen atom is selected from fluorine, chlorine, bromine and iodine, preferably iodine.

The salts are selected from the group comprising the alkaline salts, in particular of sodium or potassium, the lithium, magnesium, calcium and barium salts, the ammonium salts, the salts of amines, the salts of amino alcohols such as triethanolamine or monoethanolamine.

The carboxylic acid esters are preferably formed with the linear or branched alkyls having from 1 to 6 carbon atoms, preferably tert-butyl.

In particular embodiments of the invention, the product corresponding to formula (I) is composed of an element X that represents a halogen, and an element A represented by an aryl radical, or an element X represented by a halogen and an element A represented by a cycloalkyl, or an element X represented by a halogen and an element A represented by a

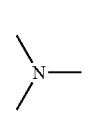

group, or an element X represented by a halogen and an element A represented by

a group, or an element X represented by a halogen and an element A represented by

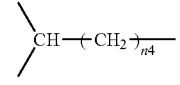

group, or an element X represented by a nucleofuge and an element A represented by an aryl radical, or an element X represented by a nucleofuge and an element A represented by a cycloalkyl, or an element X represented by a nucleofuge and an element A represented by a

group, or an element X represented by a nucleofuge and an element A represented by a

group, or an element X represented by a nucleofuge and an element A represented by a

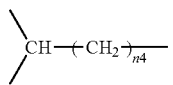

group, or an element X represented by a

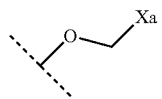

group and an element A represented by an aryl radical, or an element X represented by a

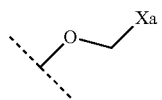

group and an element A represented by a cycloalkyl, or an element X represented by a

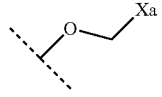

group and an element A represented by a

group, or an element X represented by a

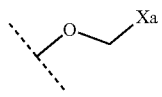

group and an element A represented by a

group, or an element X represented by a

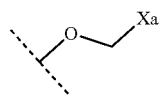

group and an element A represented by a

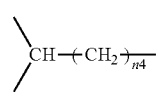

group, or an element X represented by a

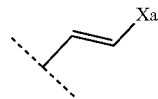

group and an element A represented by an aryl radical, or an element X represented by a

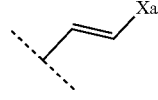

group and an element A represented by a cycloalkyl, or an element X represented by a

group and an element A represented by a

group, or an element X represented by a

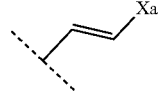

group and an element A represented by a

group, or an element X represented by a

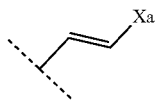

group and an element A represented by a

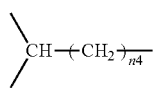

group, $X_1$ being a C=O or a single bond
$X_2$ being an NH group or a single bond
$X_3$ being an oxygen or a single bond
s is equal to 1, 2 or 3
r being equal to 0, 1 or 2
it being understood that the sum r+s is equal to 3
$n_1$ is an integer equal to 0, 1, 2 or 3; $n_2$ is an integer equal to 1, 2 or 3 and $n_3$ is an integer equal to 1, 2 or 3,
$n_4$ is an integer equal to 1, 2, 3 or 4,
W represents
an —OH radical,
an -L radical which represents a linker body comprising a terminal reactive function,
an —FL fluorophore group used in diagnostics or analysis, involving detection of fluorescence preferably selected from rhodamine or a derivative thereof, preferably rhodamine B, fluorescein isothiocyanate (FITC), a Cy dye preferably selected from Cy5, Cy5.5, Cy7, an Alexa fluor dye preferably selected from Alexa Fluor 647, 700 or 750, Texas Red, allophycocyanin (APC) and conjugates thereof with other fluorochromes in particular those mentioned above, phycoerythrin (PE) and conjugates thereof with other fluorochromes in particular those mentioned above,
an R* radioactive radical, which preferably contains either a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA;
or a bifunctional ligand preferably selected from one of the acyclic chelating agents from the list constituted by EDTA, CyEDTA, EDTMP, DTPMP, DTPA, CyDTPA, $Cy_2DTPA$, DTPA-MA, DTPA-BA, BOPA;
or a bifunctional ligand preferably selected from one of the macrocyclic chelating agents from the list constituted by DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA;
or a bifunctional chelating agent of the cationic, anionic, neutral or cleavable type;
or a radionuclide preferably selected from $^{67}Cu$, $^{64}Cu$, $^{90}Y$, $^{109}Pd$, $^{111}Ag$, $^{149}Pm$, $^{153}Sm$, $^{166}Ho$, $^{177}Lu$, $^{186}Re$, $^{188}Re$, $^{99m}Tc$, $^{67}Ga$, $^{68}Ga$, $^{111}In$, $^{90}Y$, $^{177}Lu$, $^{186}Re$, $^{188}Re$, $^{197}Au$, $^{198}Au$, $^{199}Au$, $^{105}Rh$, $^{165}Ho$, $^{166}Ho$, $^{161}Tb$, $^{149}Pm$, $^{44}Sc$, $^{47}Sc$, $^{70}As$, $^{71}As$, $^{72}As$, $^{73}As$, $^{74}As$, $^{76}As$, $^{77}As$, $^{212}Pb$, $^{212}Bi$, $^{213}Bi$, $^{225}Ac$, $^{117m}Sn$, $^{67}Ga$, $^{201}Tl$, $^{123}I$, $^{131}I$, $^{160}Gd$, $^{148}Nd$, $^{89}Sr$, $^{211}At$, an -L-M radical in which L has the meaning given above and M represents a cytotoxic drug selected from a chemotherapeutic agent or a toxin, P is a protein comprising at least one disulphide bridge and t represents an integer from 1 to 15, preferably from 1 to 6 and 13 as well as the derivatives of the carboxylic acid function or functions such as the salts, esters or amides, preferably the amide formed with butanimide.

Advantageously, the invention relates to a product characterized in that it corresponds to formula I selected from the formulae IB, IB1, IB2 and IA:

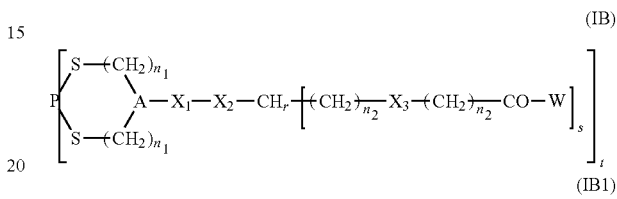
(IB)

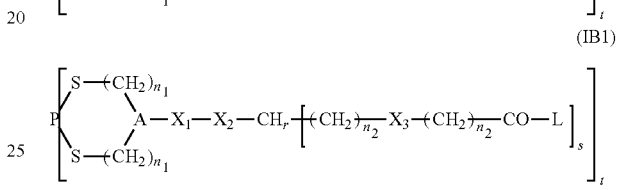
(IB1)

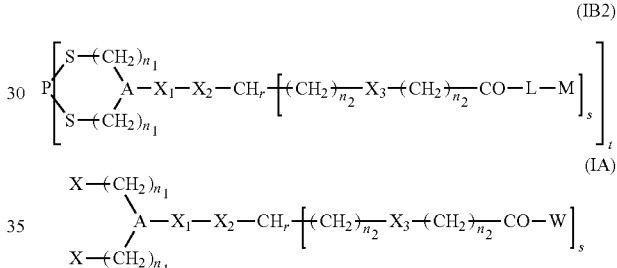
(IB2)

(IA)

in formulae IA and IB:
X is Br or I, or a

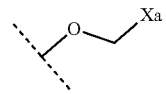

group, or a

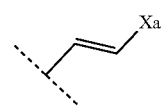

group, $X_a$ being a halogen or a nucleofuge.
A represents either an aryl or cycloalkyl radical, said aryl or cycloalkyl radicals being carbocyclic or heterocyclic,
or A represents
a

group, a

group or a

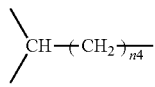

group $X_1$ is a C=O or an NH group or a single bond
$X_2$ is an NH group or a C=O or a single bond
$X_3$ is an oxygen or a single bond
s is equal to 1, 2 or 3
r is equal to 0, 1 or 2
it being understood that the sum r+s is equal to 3
$n_1$ is an integer equal to 0 or 1; $n_2$ is an integer equal to 1, 2 or 3 and $n_3$ is an integer equal to 1, 2 or 3
$n_4$ is an integer equal to 1, 2, 3 or 4
W represents
an -L radical which represents a linker body comprising a terminal reactive function,
an —FL fluorophore group used in diagnostics or analysis, involving detection of fluorescence preferably selected from rhodamine or a derivative thereof, preferably rhodamine B, fluorescein isothiocyanate (FITC), a Cy dye preferably selected from Cy5, Cy5.5, Cy7, an Alexa fluor dye preferably selected from Alexa Fluor 647, 700 or 750, Texas Red, Nile Blue A, allophycocyanin (APC) and conjugates thereof with other fluorochromes in particular those mentioned above, phycoerythrin (PE) and conjugates thereof with other fluorochromes in particular those mentioned above,
an R* radioactive radical which preferably contains
either a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA,
or a bifunctional ligand preferably selected from one of the acyclic chelating agents from the list constituted by EDTA, CyEDTA, EDTMP, DTPMP, DTPA, CyDTPA, $Cy_2$DTPA, DTPA-MA, DTPA-BA, BOPA,
or a bifunctional ligand preferably selected from one of the macrocyclic chelating agents from the list constituted by DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA,
or a bifunctional chelating agent of the cationic, anionic, neutral or cleavable type,
or a radionuclide preferably selected from $^{67}$Cu, $^{64}$Cu, $^{90}$Y, $^{109}$Pd, $^{111}$Ag, $^{149}$Pm, $^{153}$Sm, $^{166}$Ho, $^{177}$Lu, $^{186}$Re, $^{188}$Re, $^{99m}$Tc, $^{67}$Ga, $^{68}$Ga, $^{111}$In, $^{90}$Y, $^{177}$Lu, $^{186}$Re, $^{188}$Re, $^{197}$Au, $^{198}$Au, $^{199}$Au, $^{105}$Rh, $^{165}$Ho, $^{166}$Ho, $^{161}$Tb, $^{149}$Pm, $^{44}$Sc, $^{47}$Sc, $^{70}$As, $^{71}$As, $^{72}$As, $^{73}$As, $^{74}$As, $^{76}$As, $^{77}$As, $^{212}$Pb, $^{212}$Bi, $^{213}$Bi, $^{225}$Ac, $^{117m}$Sn, $^{67}$Ga, $^{201}$Tl, $^{123}$I, $^{131}$I, $^{160}$Gd, $^{148}$Nd, $^{89}$Sr, $^{211}$At, a cytotoxic drug M selected from a chemotherapeutic agent or a toxin, in particular monomethyl auristatin E or monomethyl auristatin F,
an -L-M radical in which L and M have the meanings given above, P is a protein comprising at least one disulphide bridge and t represents an integer from 1 to 15, preferably from 1 to 6 and 13 as well as the derivatives of the carboxylic acid function or functions such as the salts, esters or amides, preferably the amide formed with butanimide.

In a particular embodiment of the invention, at least one of the elements X1, X2 or X3 is not a single bond.

In a particular embodiment of the invention, the element X is Br or I.

In a particular embodiment of the invention, the product characterized in that it corresponds to formula (I) above has at its end a group corresponding to the following formula:

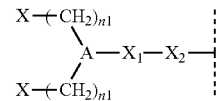

which is selected from the following radicals:

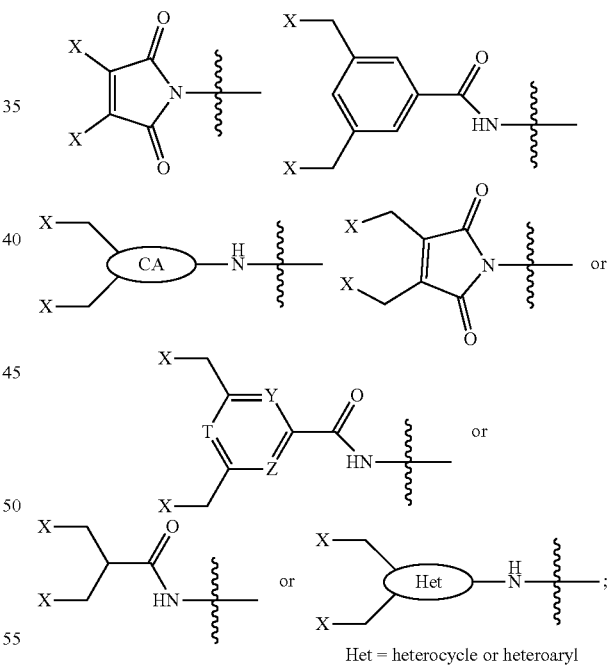

Het = heterocycle or heteroaryl or aryl and in that the

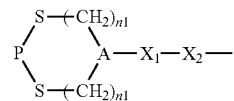

group is selected from the following radicals:

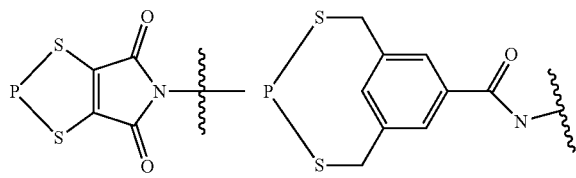

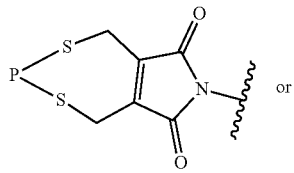 or

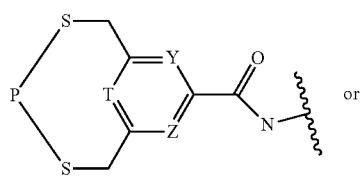 or

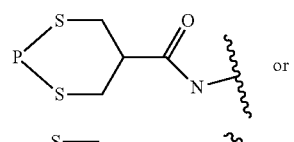 or

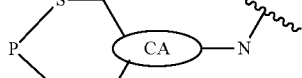

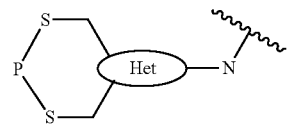

Het = heterocycle or heteroaryl
or aryl;
CA = cycloalkyl radicals in which X is a halogen, or a nucleofuge, in the triad of atoms (T,Y,Z) each of these atoms represents, independently of the other two atoms, a carbon or nitrogen atom, and Het represents a carbocyclic or heterocyclic aryl radical or a heterocyclic cycloalkyl radical and CA represents a cycloalkyl radical.

The three atoms T, Y and Z can correspond to the triad of atoms (C,C,C) or (N,C,C) or (C,N,C) or (C,C,N) or (C,N,N) or (N,C,N) or (N,N,C) or (N,N,N), preferably (C,C,C) and (N,C,C).

In a particular embodiment of the invention, the product characterized in that it corresponds to formula (I) above has at its end a group corresponding to the following formula:

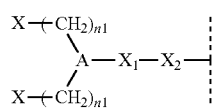

which is selected from the following radicals:

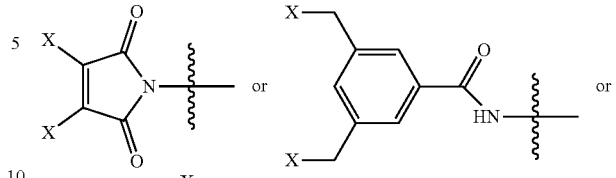

and in that the

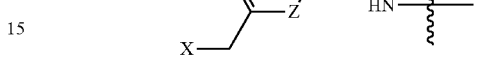

group is selected from the following radicals:

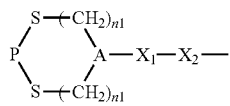 or

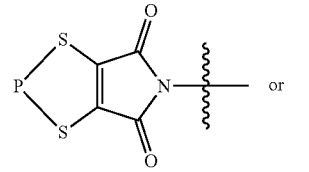 or

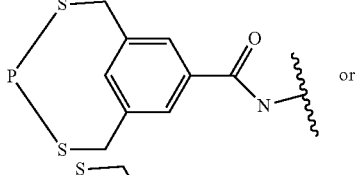

radicals in which X is Br or I, and in the triad of atoms (T,Y,Z) each of these atoms represents, independently of the other two atoms, a carbon or nitrogen atom, in particular T is a nitrogen atom and Y and Z represent CH.

In a particular embodiment of the invention, the product characterized in that it corresponds to formula (I), selected from formulae IA and IB, comprises a

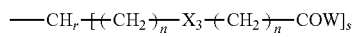

group which can be represented by a —$(CH_2)_5$—$CO_2H$ radical.

In another embodiment of the invention, the product corresponding to general formula (I) constituted by formulae IA and IB in which W corresponds to an element L, so as to correspond to the following general formula IA1:

which is selected from the following radicals:

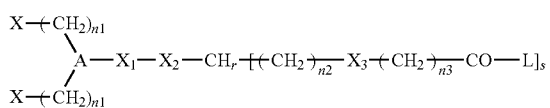
(IA1)

or IB1:

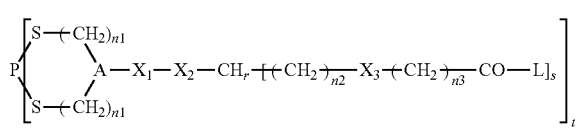
(IB1)

in which:
X is Br or I, or a

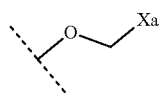

group, or a

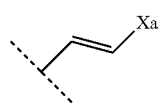

group

A represents either an aryl or cycloalkyl radical, said aryl or cycloalkyl radicals being carbocyclic or heterocyclic,
or A represents
a

group, a

group or a

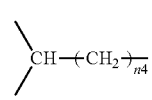

group
$X_1$ is a C=O or an NH group or a single bond
$X_2$ is an NH group or a C=O or a single bond
$X_3$ is an oxygen or a single bond s is equal to 1, 2 or 3 r is equal to 0, 1 or 2 it being understood that the sum r+s is equal to 3

$n_1$ is an integer equal to 0 or 1; $n_2$ is an integer equal to 1, 2 or 3 and $n_3$ is an integer equal to 1, 2 or 3, $n_4$ is an integer equal to 1, 2, 3, or 4, L represents a linker body comprising a terminal reactive function;

P is a protein comprising at least one disulphide bridge, and t represents an integer from 1 to 15, preferably from 1 to 6 and 13, as well as the derivatives of the carboxylic acid function or functions such as the salts, esters or amides, preferably the amide formed with butanimide.

Within the meaning of the present invention, by "terminal reactive function" is meant any atom or group of atoms allowing one or more molecular assemblies by conventional organic chemistry or combinatorial chemistry.

In another particular embodiment of the invention, the product according to the invention comprises a linker body L corresponding to general formula III, IIIa or IIIb below:

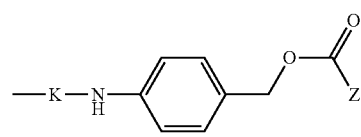
(III)

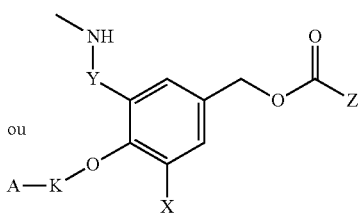
(IIIa)

ou

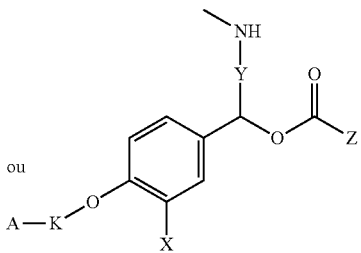
(IIIb)

ou in which K represents a (AA) $n_5$ radical representing a sequence of n5 identical or different, natural or non-natural amino acids or K represents a cleavage site recognized by an enzyme or K represents a hydrazino radical optionally coupled to the (AA) $n_5$ radical, or K represents a saccharide group preferably selected from a beta-glucuronic acid or a beta-D-galactose or a beta-D-glucose or an alpha-D-mannose or an N-acetyl-D-glucosaminyl or an N-acetyl-D-galactosaminyl, a D-glucuronyl, an L-iduronyl, a D-glucopyranosyl, a D-galactopyranosyl, a D-mannopyranosyl or L-fucopyranosyl.

X represents a hydrogen or an $NO_2$ group,

A preferably represents a hydrogen atom,

Y represents a

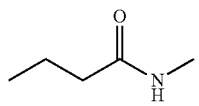

chain or a single bond or a chemical spacer arm preferably selected from the group formed by the linear or branched alkyl radicals having from 1 to 30 carbon atoms optionally interrupted by one or more oxygen, sulphur or nitrogen atoms, for example a polyethylene glycol.

Z represents a leaving group, and $n_5$ represents an integer from 1 to 6.

The leaving group Z can be selected from the group comprising para nitro or para cyano phenyloxy. Preferably, the leaving group Z is one of the following radicals:

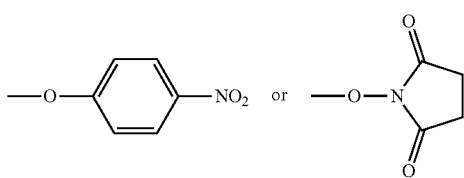

or a chlorine atom.

In another embodiment of the invention, the product corresponding to general formula III, or IIIa or IIIb comprises the (AA) $n_5$ radical, which is such that $n_5$ is equal to 1, 2, 3, 4 or 5, and AA is a pair of amino acids, said amino acids being selected from the group constituted by: a valine, a citrulline, a phenylalanine, a lysine, an aspartic acid, a methionine, an asparagine, a proline, an isoleucine, an alanine, an arginine, a glycine or a glutamic acid.

In a preferred embodiment, $n_5$ is equal to 2 or 3, preferably 2 and (AA) $n_5$ is a pair of amino acids selected from: a valine and a citrulline, or a phenylalanine and a lysine, or a valine and an alanine, or a valine and an aspartic acid, or a lysine and a methionine, or a lysine and an asparagine, or a proline and an isoleucine, or a proline and a lysine, or a lysine and a methionine, or a lysine and an asparagine, or a valine and a lysine, or an alanine and a lysine, or a phenylalanine and a lysine, or two phenylalanines and a lysine, or an alanine, or a phenylalanine and a lysine, or two arginines, or a lysine and an arginine, or a glutamic acid, or a glycine and an arginine, or two glycines and an arginine.

In a particular embodiment of the invention, the product corresponding to formula III, or IIIa, or IIIb, comprises an element K that represents a site of cleavage by an enzyme selected from the enzymes of the cathepsin B, cathepsin C, cathepsin D type, the enzymes selected from plasmin, a lysosomal protease, a lysosomal enzyme, or urokinase plasminogen activator (uPA), elastase, proteinase 3, cathepsin G.

K can also represent a recognition site of cleavage by an enzyme of the matrix metalloproteinase (MMP) type. In this case, the enzyme of the matrix metalloproteinase (MMP) type is preferably selected from collagenases 1, 2 and 3 (MMP-1, MMP-8, MMP-13), gelatinases A and B (MMP-2 and MMP-9), stromelysins 1 and 2 (MMP-3 and MMP-10), matrilysins 1, 2 and 3 (MMP-7, MMP-26, MMP-11), macrophage metalloelastase (MMP-12), the membrane MMPs (MMP-14, MMP-15, MMP-16, MMP-17, MMP-24 and MMP-25), enamelysin (MMP-20), CA-MMP (MMP-23), epilysin (MMP-18) and PSMA.

K can also represent a recognition site of cleavage by an esterase, a carboxylesterase, alkaline phosphatases, proteases, peptidases, cathepsins, glucosidase, galactosidase, β-D-galactosidase, induronidase, β-glucuronidase, mannosidase, N-acetyl-D-glucosaminidase or N-acetyl-D-galactosaminidase.

In the context of the present invention, by "cleavage site" is meant the position where cleavage of the peptide chain by an enzyme takes place, for example the Valine-Citrulline site, the above cleavage sites K or the position where enzyme recognition takes place.

In a particular embodiment of the invention, the product corresponds to general formula IA2

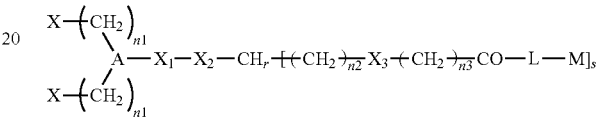

(IA2)

or to formula IB2

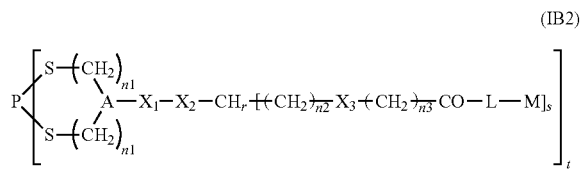

(IB2)

in which X is Br or I, or a

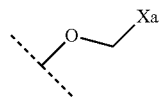

group, or a

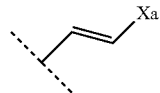

group

A represents either an aryl or cycloalkyl radical, said aryl or cycloalkyl radicals being carbocyclic or heterocyclic, or A represents a

group, a

group or a

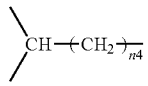

group $X_1$ is a C=O or an NH group or a single bond
$X_2$ is an NH group or a C=O or a single bond
$X_3$ is an oxygen or a single bond
s is equal to 1, 2 or 3
r is equal to 0, 1 or 2
it being understood that the sum r+s is equal to 3
$n_1$ is an integer equal to 0 or 1; $n_2$ is an integer equal to 1, 2 or 3 and $n_3$ is an integer equal to 1, 2 or 3, $n_4$ is an integer equal to 1, 2, 3 or 4,
and L represents a linker body comprising a terminal reactive function,
P is a protein comprising at least one disulphide bridge,
t represents an integer from 1 to 15, preferably from 1 to 6 and 13,
M is a cytotoxic drug selected from a chemotherapeutic agent or a toxin,
as well as the derivatives of the carboxylic acid function or functions such as the salts, esters or amides, preferably the amide formed with butanimide.

Within the meaning of the present application, by "cytotoxic drug" is meant any natural or synthetic molecule capable of inhibiting or preventing the function of the cells. By "cytotoxic" is also meant the property of a chemical or biological agent of altering cells, optionally until they are destroyed.

In a particular embodiment of the invention, the drug M is a drug selected from any compound for which marketing authorization has been obtained and which is used in anti-cancer or anti-inflammatory therapy, and any molecule undergoing clinical evaluation in anticancer or anti-inflammatory therapy. The drug M will be selected for example from paclitaxel (Taxol®) or docetaxel (Taxotere®) or a derivative thereof, topotecan, bortezomib, daunorubicin, the analogues of daunorubicin, vincristine, mitomycin C, retinoic acid, methotrexate, Ilomedin, aspirin, an IMIDs, lenalidomide, pomalidomide.

In another particular embodiment of the invention, the drug M is selected from the group constituted by duocarmycin and its analogues, the dolastatins, combretastatin, calicheamicin, N-acetyl-γ-calicheamycin (CMC), a calicheamycin derivative, maytansine and its analogues, DM-I, auristatin E, auristatin EB (AEB), auristatin EFP (AEFP), monomethyl auristatin E (MMAE), monomethyl auristatin F (MMAF), tubulysin, disorazole, the epothilones, echinomycin, estramustine, cemadotine, eleutherobin, methopterin, actinomycin, mitomycin A, camptothecin, a camptothecin derivative, SN38, maytansine, a derivative of the maytansinoid type, DM1, DM4, TK1, amanitin, a pyrrolobenzodiazepine, a pyrrolobenzodiazepine dimer, a pyrrolopyridodiazepine, a pyrrolopyridodiazepine dimer, a DNA intercalator, a histone deacetylase inhibitor, or a tyrosine kinase inhibitor.

In another particular embodiment of the invention, the drug M is selected from *pseudomonas* exotoxin (PE), deBouganin, Bouganin, diphtheria toxin (DT) and ricin.

In another particular embodiment of the invention, the product according to the invention corresponds to the following formula IB2:

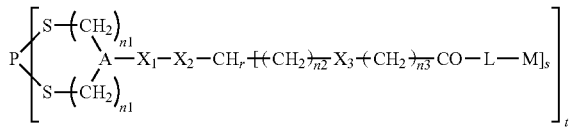

(IB2)

in which:
X is Br or I, or a

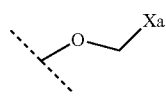

group, or a

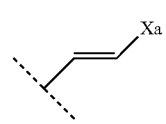

group
A represents either an aryl or cycloalkyl radical, said aryl or cycloalkyl radicals being carbocyclic or heterocyclic,
or A represents
a

group, a

group or a

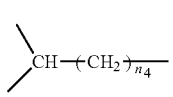

group
$X_1$ is a C=O or an NH group or a single bond
$X_2$ is an NH group or a C=O or a single bond
$X_3$ is an oxygen or a single bond
s is equal to 1, 2 or 3
r is equal to 0, 1 or 2
it being understood that the sum r+s is equal to 3

$n_1$ is an integer equal to 0 or 1; $n_2$ is an integer equal to 1, 2 or 3 and $n_3$ is an integer equal to 1, 2 or 3, $n_4$ is an integer equal to 1, 2, 3 or 4, L represents a linker body comprising a terminal reactive function, M is a cytotoxic drug or a toxin, P is a protein comprising at least one disulphide bridge, and t represents an integer, preferably from 1 to 6 and 13, as well as the derivatives of the carboxylic acid function or functions such as the salts, esters or amides, preferably the amide formed with butanimide.

In a particular embodiment of the invention, the protein P comprising at least one disulphide bridge is selected from an agonist or an antagonist, an antibody or an antibody fragment, a fusion protein comprising an antibody or an antibody fragment, an albumin or a peptide.

By "agonist" is meant any molecule which, on binding specifically to a given cell receptor, triggers the same effects as the natural ligand.

By "antagonist" is meant any molecule which, on binding specifically to a given cell receptor, can thus block the action of the endogenous ligand by opposing binding of the ligand to its receptor.

By "antibody", also commonly called "immunoglobulin", is meant a heterotetramer constituted by two heavy chains of approximately 50-70 kDa each (called the H chains, for Heavy) and two light chains of approximately 25 kDa each (called the L chains, for Light), joined together by intra- and interchain disulphide bridges.

Each chain is constituted, in the N-terminal position, by a variable region or domain, called VL for the light chain, VH for the heavy chain and, in the C-terminal position, by a constant region, constituted by a single domain called CL for the light chain and of three or four domains called CH1, CH2, CH3, CH4, for the heavy chain.

By "antibody fragment" is meant any part of an immunoglobulin obtained by enzymatic digestion or obtained by bioproduction.

The antibody according to the present invention can be a chimeric monoclonal antibody, humanized or human, monospecific or bispecific.

By "chimeric antibody" is meant an antibody in which the sequences of the variable regions of the light chains and of the heavy chains belong to a species different from that of the sequences of constant regions of the light chains and of the heavy chains.

For the purposes of the invention, the sequences of the variable regions of the heavy and light chains are preferably of murine origin whereas the sequences of the constant regions of the heavy and light chains belong to a non-murine species. In this respect, for the constant regions, all the species of non-murine mammals can be used, and in particular human, monkey, Old-World swine, bovines, equines, felids, canines or birds, this list not being exhaustive.

Preferably, the chimeric antibodies according to the invention contain sequences of constant regions of heavy and light chains of human origin and the sequences of variable regions of heavy and light chains of murine origin.

By "humanized antibody" is meant an antibody for which some or all of the sequences of the regions involved in antigen recognition (the hypervariable regions or CDR: Complementarity Determining Region) and sometimes certain amino acids of the FR regions (FR: Framework Regions)) are of non-human origin whereas the sequences of the constant regions and variable regions not involved in antigen recognition are of human origin.

By "human antibody" is meant an antibody containing only human sequences, both for the variable and constant regions of the light chains and for the variable and constant regions of the heavy chains.

In another particular embodiment of the invention, the protein P can be an antibody fragment. This antibody fragment is selected from the group constituted by: Fab, F(ab')2, Fc, F'c, pFc', ScFv, Fv, Fd, Fabc, diabody, minibody, ScFv-Fc or ScFv-Fv.

Enzymatic digestion of the immunoglobulins by papain generates two identical fragments, which are called the Fab (Fragment antigen binding) fragments, and one Fc (Fragment crystallizable) fragment.

Enzymatic digestion of the immunoglobulins by pepsin generates a F(ab')2 fragment and an Fc fragment split into several peptides.

F(ab')2 is formed by two Fab' fragments linked by interchain disulphide bridges.

The Fab parts are constituted by the variable regions and the CH1 and CL domains, whereas the Fc region is constituted by the two globular domains CH2 and CH3 (and CH4 when it is present).

The Fab' fragment is constituted by the Fab region and a hinge region. Fab'-SH refers to a Fab' fragment in which the cysteine residue of the hinge region bears a free thiol group (Carter et al., Nature BioTechnology 10: 163-167 (1992)). The Fv fragment is composed of the domains VH and VL linked by disulphide bridges. It is the smallest fragment retaining antigen binding activity.

The Fd fragment is formed by the VH and CH1 domains.

The "F'c", "pFc'", and "Fabc" fragments are defined in FIGS. 6A to 6C.

The scFv (single chain Fragment variable) is a fragment originating from protein engineering which is constituted only by the variable domains VH and VL. The structure is stabilized by a short flexible peptide arm, called a linker, which is placed between the two domains.

The ScFv fragment can be bound to an Fc fragment in order in order to produce an ScFv-Fc or to an Fv fragment in order in order to produce an ScFv-Fv.

If the size of the binding peptide is reduced, new steric constraints appear between the scFvs; the VH and VL domains can no longer combine into a functional structure and multimeric structures are obtained (dimeric: "diabody", trimeric: "triabody" and tetrameric: "tetrabody").

In the context of the present invention, diabodies can be used. They can have multiple valences and specificities.

The term "valent" denotes the presence of a defined number of antigen binding sites in an antibody molecule.

The term "specific" refers to the different types of antigens that can bind to the same antibody.

Thus, in the present invention, by "diabody" is meant an scFv dimer, said diabody being divalent, mono- or bispecific according to whether it binds two identical or different antigens.

The Fab, Fv and scFv fragments are monovalent and monospecific.

By "minibody" is meant a fragment composed of a light chain, of a heavy chain bound to a CH3 group.

In the context of the present invention, the antibody or antibody fragment is directed against a tumour antigen or inflammation antigen.

In a particular embodiment of the invention, the antibody or antibody fragment is directed against one of the antigens of the cluster of differentiation (CD), the identification number of which varies between CD1a and CD363; in this list, the following CDs are preferred: CD1a, CD363, CD3, CD4, CD13, CD19, CD20, CD21, CD22, CD25, CD30, CD31, CD33, CD34, CD37, CD39, CD40, CD44, CD47, CD52, CD56, CD66e, CD70, CD72, CD73, CD74, CD79, CD79b, CD80, CD86, CD117, CD138, CD194, CD205, CD227 or CD248. The antibody or antibody fragment can also be directed against one of the antigens selected from the list formed by the following: CA125, G250, GD2, HLA-DRβ, MUC1, VEGF, VEGFA, VEGF-R1/2, TRAIL-R2 (DR5), EpCAM, GPIIb, GPIIIa, TNF alpha, TNFR, TNT, Lewis Y, EGFR, HER-2, HER-3, HER-3 MM-111, HER-4, homodimer or heterodimer between members of the erbbn family (n between 1 and 4), AXL, Protein F, IgE-Fc, VEGF-A, integrin α4, integrin α4β7, integrin αV, C5, IL-6R, IL-6Rα, IL12, IL15, IL18, IL23, IL-1β, IL-1, TPO-R, GPNMB, PSMA, PSA, PAP, PSM, integrin αv, Cripto, TACSTD2 (TROP2 or EGP1), CEA, Folate receptor 1, Mucin 16, Endothelin Receptor ETB, STEAP1, SLC44A4 (AGS-5), Nectin 4, AGS-16, Guanylyl cyclase C, Mucin 1, EGFRvIII, Mesothelin, IL2R, A33, Can, VEGF-B, VEGF-C, VEGF-D, VEGF-E, VEGFR-1, VEGFR-2. VEGFR-3, TGFβ, TGFβR, FGF, FGF8b, FGFR, PDGF, PDGFR, PDGFRα, PDGFRβ, Ang-1, Ang-2, integrin, αvβ3, αvβ5, α3β1, α6β4, α2β1, anti-integrin α4, RANK-L, BLyS, c-MET, DR, DR10, TCRαβ, ICOS, CTLA-4, CAIX (MN), EphA2, CA6, ovarian CA6, cervical CA6, breast CA6, angiopoietin-2, Cripto, ENPP3, Mesothelin, FOLR1, Nectin-4, TIM-1, Muc-16, Tissue Factor, LIV-1, GM2, α 5 integrin, TLR-7, PD-1, AFP, CA125 (MUC16), Sialyl LewisY, CAMPATH-1, HLA-DR, anti-idiotype, carcinoembryonic antigen (CEA), TAG-72, Folate-binding protein, A33, G250, gangliosides (including GD2, GD3, GM2), LeY, collagen 4 (collagen IV), collagen 18 (collagen XVIII), SC6, CA-125, CA19-9, p185HER2, de2-7 EGFR, Fibroblast activation protein (FAP), Tenascin, metalloproteinases, Endosialin, Carbonic anhydrase, Galectin 9, Aldolase A, eIFγ4, Tyrosinase, Galectin 4, HERKV-K10, p53, NY-LU-12, Restin, NY-CO-38, MAGE-1, MAGE-4a, SSX2, NY-ESO-1, SCP-1, HGFR, PTK 7, CCK-4, PDGFR, PTP-LAR, CDCP1, CADM1, IGSF4, Lu, BCAM, CEACAM6, JAM-A, PTGFRN (CD9P-1), MCAM, MUC18, MCP, EMMPRIN, TfR, TRAILR2, C1qR, hTERT, Survivin, MDM2, CYP1B1, Melan-A, MART-1, MART-2, Melanosomal proteins, gp100, neo-PAP, CDC27, MAGEs, WT1, MUM-1, MUM-2, MUM-3, BRAF, TPI, fibronectin, K-ras, β-catenin, CDK4, caspase-8, p14ARF, p16INK4a, TGFβRII, bcr-ab1, SYT-SSX, TRP-1, TRP-2, GnT-V, tyrosinase, FGF5, TEL-AML1, Proteinase 3, HER2/neu, AFP, MUC-1, EBV-EBNA, HTLV-1 tax, HPV16-E7, mutated HLA-A2, HA1, SART3, GnT-V, CEACAM5, AGS-16, GPNMB, ESAT-6, RANK, CanAg, fibrin, TF, PRAME, CA19-9, CA50, CA125, CA195, CAM17.1/WGA, AFP, β2-MG, DU-PAN2, HE4, b-2 microglobulin, transferrin, transthyretin, ApoA1, TROP-2, CTLA-4, GITR, PD-1, PD-L1, c-KIT, CD11b-CD18 integrin heterodimer, DNA/Histon H1 Folate, EpCAM, Tenascin-c, ECM (proteoglycan or fibronectin), fibrinogen, SV40 large T antigen, SC6-Ag, SC—Ag, DR4 (death receptor 4), DR5, ESA, mucin, hPAM4, hRS7, HLA-DR, CCR4, MTX1, MTX2, PECAM, thrombomodulin Tn, cathepsin D, TYRO-3, MER. The antibody or antibody fragment can also be directed against a PF4/heparin complex.

The invention also relates to a method for preparing the products of formulae I, characterized in that, if desired, a product of formula IA3

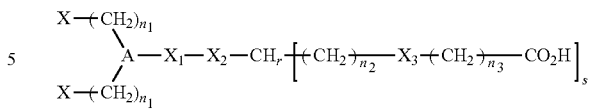

as well as the derivatives of the carboxylic acid function or functions such as the salts, esters or amides, preferably the amide formed with butanimide, where in formula IA3:

X is Br or I, or a

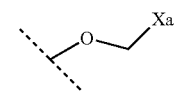

group, or a

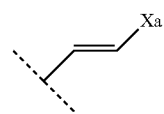

group, $X_a$ being a halogen or a nucleofuge

A represents either an aryl or cycloalkyl radical, said aryl or cycloalkyl radicals being carbocyclic or heterocyclic, or A represents a

group, a

group or a

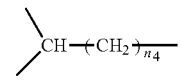

group $X_1$ is a C=O or an NH group or a single bond
$X_2$ is an NH group or a C=O or a single bond
$X_3$ is an oxygen or a single bond
s is equal to 1, 2 or 3
r is equal to 0, 1 or 2
it being understood that the sum r+s is equal to 3
$n_1$ is an integer equal to 0 or 1; $n_2$ is an integer equal to 1, 2 or 3 and $n_3$ is an integer equal to 1, 2 or 3,
$n_4$ is an integer equal to 1, 2, 3, or 4,
is reacted with a product of formula H2N-L, or HO-L in which L represents a linker body comprising a terminal reactive function, in order to obtain a product of formula IA1:

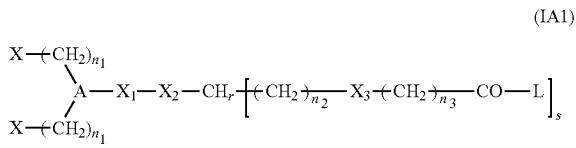

(IA1)

and, if desired, the product of formula IA1 is reacted with a product of formula:

H2N—M, or HO—M in which M represents a cytotoxic drug selected from a chemotherapeutic agent or a toxin, in order to obtain a product of formula IA2:

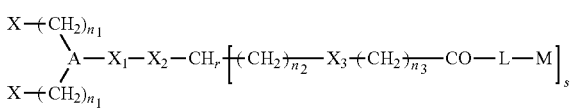

(IA2)

or product of formula IA3 which, if desired, is reacted with a residue of an —FL fluorescent radical in order to obtain a product of formula (IA4)

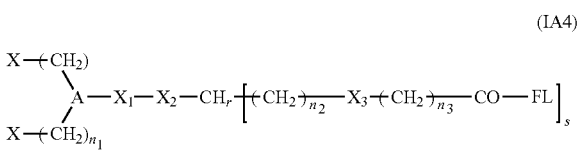

(IA4)

or product of formula IA3 which, if desired, is reacted with a residue of an —R* radioactive radical in order to obtain a product of formula (IA5)

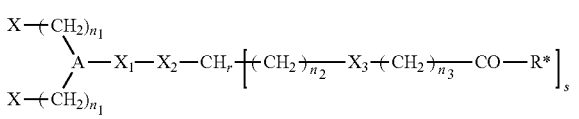

(IA5)

The products of formulae IA1 to IA5 corresponding to the products of formula IA which, if desired, are reacted with a product of formula P, P being a protein comprising at least one disulphide bridge and t represents an integer from 1 to 15, preferably from 1 to 6 and 13, in order to obtain a product of formula (IB):

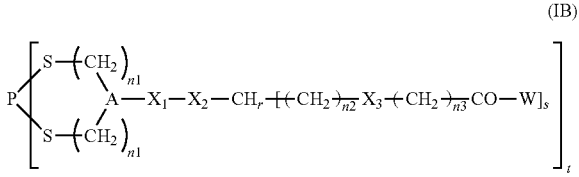

(IB)

in which W represents
an -L radical which represents a linker body comprising a terminal reactive function,
an —FL fluorophore group used in diagnostics or analysis, involving detection of fluorescence preferably selected from rhodamine or a derivative thereof, preferably rhodamine B, fluorescein isothiocyanate (FITC), a Cy dye preferably selected from Cy5, Cy5.5, Cy7, an Alexa fluor dye preferably selected from Alexa Fluor 647, 700 or 750, Texas Red, Nile Blue A, allophycocyanin (APC) and conjugates thereof with other fluorochromes in particular those mentioned above, phycoerythrin (PE) and conjugates thereof with other fluorochromes in particular those mentioned above, an R* radioactive radical which preferably contains
either a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA, or a bifunctional ligand preferably selected from one of the acyclic chelating agents from the list constituted by EDTA, CyEDTA, EDTMP, DTPMP, DTPA, CyDTPA, $Cy_2DTPA$, DTPA-MA, DTPA-BA, BOPA, or a bifunctional ligand preferably selected from one of the macrocyclic chelating agents from the list constituted by DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA, or a bifunctional chelating agent of the cationic, anionic, neutral or cleavable type, or a radionuclide preferably selected from $^{67}Cu$, $^{64}Cu$, $^{90}Y$, $^{109}Pd$, $^{111}Ag$, $^{149}Pm$, $^{153}Sm$, $^{166}Ho$, $^{177}Lu$, $^{186}Re$, $^{188}Re$, $^{99m}Tc$, $^{67}Ga$, $^{68}Ga$, $^{111}In$, $^{90}Y$, $^{177}Lu$, $^{186}Re$, $^{188}Re$, $^{197}Au$, $^{198}Au$, $^{199}Au$, $^{105}Rh$, $^{165}Ho$, $^{166}Ho$, $^{161}Tb$, $^{149}Pm$, $^{44}Sc$, $^{47}Sc$, $^{70}As$, $^{71}As$, $^{72}As$, $^{73}As$, $^{74}As$, $^{76}As$, $^{77}As$, $^{212}Pb$, $^{212}Bi$, $^{213}Bi$, $^{225}Ac$, $^{117m}Sn$, $^{67}Ga$, $^{201}Tl$, $^{123}I$, $^{131}I$, $^{160}Gd$, $^{148}Nd$, $^{89}Sr$, $^{211}At$, a cytotoxic drug M selected from a chemotherapeutic agent or a toxin, in particular monomethyl auristatin E or monomethyl auristatin F, an -L-M radical, in which L and M have the meanings given above.

In a particular embodiment of the invention, the products of formula IA1 to IA5 of the method of preparation according to the invention are attached to the protein P on at least one of its disulphide bridges by a reaction of nucleophilic substitution, typically in a phosphate buffer, in the presence of TCEP.

In a particular embodiment of the invention, the products of formula IB and in particular the products of formula IB2 are used in the treatment of a tumour, in particular colorectal cancer, hepatocarcinoma, a lung cancer, pancreatic cancer, non-small cell lung cancer, small cell lung cancer, colorectal cancer, K-RAS mutated colorectal cancer, a breast cancer, triple-negative breast cancer, metastatic breast cancer, liver cancer, head and neck cancer, Castleman disease, thyroid cancer, medulloblastoma, glioblastoma multiforme, glioma, sarcoma, anaplastic astrocytoma, kidney cancer, stomach cancer, malignant ascites, prostate cancer (metastatic or not), solid tumours, acute myeloid leukaemia, chronic lymphocytic leukaemia, melanoma, myeloma, multiple myeloma, lymphomas, mantle cell lymphoma, Hodgkin's lymphoma, non-Hodgkin's lymphoma, follicular lymphoma.

In another particular embodiment of the invention, the products of formula IB and in particular the products of formula IB2 are used in the treatment of an inflammatory or autoimmune disease in particular graft rejection, rheumatoid arthritis, Crohn's disease, psoriasis, multiple sclerosis, cryopyrin-associated periodic syndromes, thrombocytopenic purpura.

In another embodiment of the invention, the products of formula I, constituted by formulae IA:

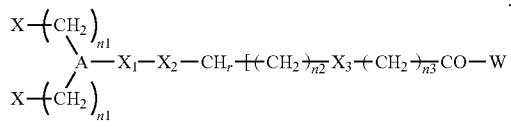

and IB:

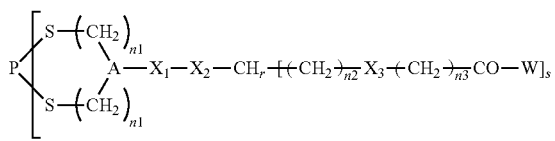

in which:

X is Br or I, or a

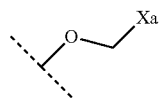

group, or a

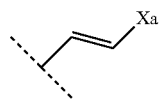

group, $X_a$ being a halogen or a nucleofuge

A represents either an aryl or cycloalkyl radical, said aryl or cycloalkyl radicals being carbocyclic or heterocyclic, or A represents a

group, a

group or a

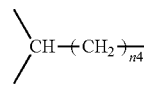

group $X_1$ is a C=O or an NH group or a single bond
$X_2$ is an NH group or a C=O or a single bond
$X_3$ is an oxygen or a single bond
s is equal to 1, 2 or 3
r is equal to 0, 1 or 2
it being understood that the sum r+s is equal to 3
$n_1$ is an integer equal to 0 or 1; $n_2$ is an integer equal to 1, 2 or 3 and $n_3$ is an integer equal to 1, 2 or 3,
$n_4$ is an integer equal to 1, 2, 3 or 4,
W represents
an -L radical which represents a linker body comprising a terminal reactive function,
an —FL fluorophore group used in diagnostics or analysis, involving detection of fluorescence preferably selected from rhodamine or a derivative thereof, preferably rhodamine B, fluorescein isothiocyanate (FITC), a Cy dye preferably selected from Cy5, Cy5.5, Cy7, an Alexa fluor dye preferably selected from Alexa Fluor 647, 700 or 750, Texas Red, Nile Blue A, allophycocyanin (APC) and conjugates thereof with other fluorochromes in particular those mentioned above, phycoerythrin (PE) and conjugates thereof with other fluorochromes in particular those mentioned above,
an R* radioactive radical which preferably contains
either a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA,
or a bifunctional ligand preferably selected from one of the acyclic chelating agents from the list constituted by EDTA, CyEDTA, EDTMP, DTPMP, DTPA, CyDTPA, $Cy_2$DTPA, DTPA-MA, DTPA-BA, BOPA,
or a bifunctional ligand preferably selected from one of the macrocyclic chelating agents from the list constituted by DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA,
or a bifunctional chelating agent of the cationic, anionic, neutral or cleavable type,
or a radionuclide preferably selected from $^{67}$Cu, $^{64}$Cu, $^{90}$Y, $^{109}$Pd, $^{111}$Ag, $^{149}$Pm, $^{153}$Sm, $^{166}$Ho, $^{177}$Lu, $^{186}$Re, $^{188}$Re, $^{99m}$Tc, $^{67}$Ga, $^{68}$Ga, $^{111}$In, $^{90}$Y, $^{177}$Lu, $^{186}$Re, $^{188}$Re, $^{197}$Au, $^{198}$Au, $^{199}$Au, $^{105}$Rh, $^{165}$Ho, $^{166}$Ho, $^{161}$Tb, $^{149}$Pm, $^{44}$Sc, $^{47}$Sc, $^{70}$As, $^{71}$As, $^{72}$As, $^{73}$As, $^{74}$As, $^{76}$As, $^{77}$As, $^{212}$Pb, $^{212}$Bi, $^{213}$Bi, $^{225}$Ac, $^{117m}$Sn, $^{67}$Ga, $^{201}$Tl, $^{123}$I, $^{131}$I, $^{160}$Gd, $^{148}$Nd, $^{89}$Sr, $^{211}$At,
a cytotoxic drug M selected from a chemotherapeutic agent or a toxin, in particular monomethyl auristatin E or monomethyl auristatin F,
an -L-M radical in which L and M have the meanings given above,
P is a protein comprising at least one disulphide bridge, and t represents an integer, preferably from 1 to 6 and 13, are used in diagnostics or in an analysis involving detection of fluorescence.

In another particular embodiment of the invention, the products of formula IA4:

(IA4)

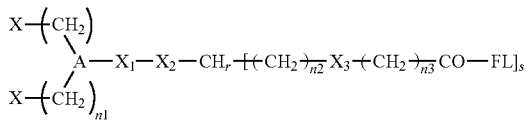

or of formula IB4

(IB4)

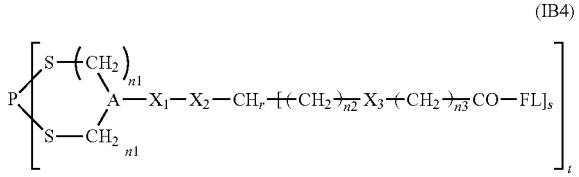

in which:
X is Br or I, or a

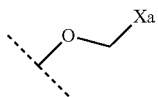

group, or a

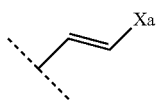

group, $X_a$ being a halogen or a nucleofuge
A represents either an aryl or cycloalkyl radical, said aryl or cycloalkyl radicals being carbocyclic or heterocyclic, or A represents a

group, a

group or a

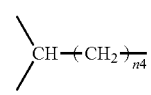

group
$X_1$ is a C=O or an NH group or a single bond
$X_2$ is an NH group or a C=O or a single bond
$X_3$ is an oxygen or a single bond s is equal to 1, 2 or 3
r is equal to 0, 1 or 2
it being understood that the sum r+s is equal to 3
$n_4$ is an integer equal to 0 or 1; $n_2$ is an integer equal to 1, 2 or 3 and $n_3$ is an integer equal to 1, 2 or 3,
$n_4$ is an integer equal to 1, 2, 3 or 4,
W represents
an -L radical which represents a linker body comprising a terminal reactive function,
an —FL fluorophore group used in diagnostics or analysis, involving detection of fluorescence preferably selected from rhodamine or a derivative thereof, preferably rhodamine B, fluorescein isothiocyanate (FITC), a Cy dye preferably selected from Cy5, Cy5.5, Cy7, an Alexa fluor dye preferably selected from Alexa Fluor 647, 700 or 750, Texas Red, Nile Blue A, allophycocyanin (APC) and conjugates thereof with other fluorochromes in particular those mentioned above, phycoerythrin (PE) and conjugates thereof with other fluorochromes in particular those mentioned above,
an R* radioactive radical which preferably contains
either a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA,
or a bifunctional ligand preferably selected from one of the acyclic chelating agents from the list constituted by EDTA, CyEDTA, EDTMP, DTPMP, DTPA, CyDTPA, $Cy_2DTPA$, DTPA-MA, DTPA-BA, BOPA,
or a bifunctional ligand preferably selected from one of the macrocyclic chelating agents from the list constituted by DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA,
or a bifunctional chelating agent of the cationic, anionic, neutral or cleavable type,
or a radionuclide preferably selected from $^{67}$Cu, $^{64}$Cu, $^{90}$Y, $^{109}$Pd, $^{111}$Ag, $^{149}$Pm, $^{153}$Sm, $^{166}$Ho, $^{177}$Lu, $^{186}$Re, $^{188}$Re, $^{99m}$Tc, $^{67}$Ga, $^{68}$Ga, $^{111}$In, $^{90}$Y, $^{177}$Lu, $^{186}$Re, $^{188}$Re, $^{197}$Au, $^{198}$Au, $^{199}$Au, $^{105}$Rh, $^{165}$Ho, $^{166}$Ho, $^{161}$Tb, $^{149}$Pm, $^{44}$Sc, $^{47}$Sc, $^{70}$As, $^{71}$As, $^{72}$As, $^{73}$As, $^{74}$As, $^{76}$As, $^{77}$As, $^{212}$Pb, $^{212}$Bi, $^{213}$Bi, $^{225}$Ac, $^{117m}$Sn, $^{67}$Ga, $^{201}$Tl, $^{123}$I, $^{131}$I, $^{160}$Gd, $^{148}$Nd, $^{89}$Sr, $^{211}$At,
a cytotoxic drug M selected from a chemotherapeutic agent or a toxin, in particular monomethyl auristatin E or monomethyl auristatin F,
an -L-M radical in which L and M have the meanings given above,
P is a protein comprising at least one disulphide bridge, and t represents an integer, preferably from 1 to 6 and 13, correspond to the products of formula IA and IB in which W represents an —FL fluorescent radical, are used in diagnostics or in analysis involving detection of fluorescence. In this case, FL is a fluorophore (or fluorochrome) preferably selected from rhodamine or a derivative thereof (preferably rhodamine B), fluorescein isothiocyanate (FITC), a Cy Dye (preferably selected from Cy5, Cy5.5, Cy7), an Alexa fluor dye (preferably selected from Alexa Fluor 647, 700 or 750), Texas Red, Nile Blue A, allophycocyanin (APC) and conjugates thereof with other fluorochromes in particular those mentioned above, phycoerythrin (PE) and conjugates thereof with other fluorochromes in particular those mentioned above, or any fluorophore used in diagnostics or analysis, involving detection of fluorescence.

The use of radioactive elements is very widespread in the medical field, whether for the needs of imaging or of therapy as illustrated by the article by Cutler et al., Chemical Reviews, 2013, 113, 858-883.

In yet another particular embodiment of the invention, the products of formula (IA5):

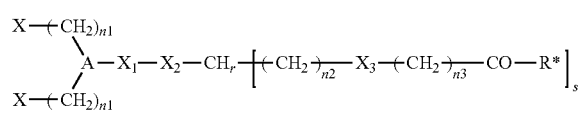

(IA5)

or of formula (IB5):

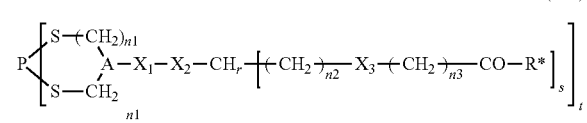

(IB5)

in which X is Br or I, or a

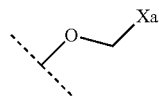

group, or a

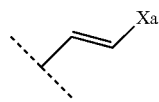

group, $X_a$ being a halogen or a nucleofuge

A represents either an aryl or cycloalkyl radical, said aryl or cycloalkyl radicals being carbocyclic or heterocyclic, or A represents a

group, a

group or a

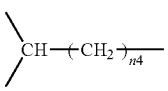

group $X_1$ is a C=O or an NH group or a single bond
$X_2$ is an NH group or a C=O or a single bond
$X_3$ is an oxygen or a single bond
s is equal to 1, 2 or 3
r is equal to 0, 1 or 2
it being understood that the sum r+s is equal to 3
$n_1$ is an integer equal to 0 or 1; $n_2$ is an integer equal to 1, 2 or 3 and $n_3$ is an integer equal to 1, 2 or 3,
$n_4$ is an integer equal to 1, 2, 3 or 4,
and R* is a radioactive radical,
P is a protein comprising at least one disulphide bridge,
and t represents an integer, preferably from 1 to 6 and 13 are used in diagnostics or in analysis involving detection of radioactivity. R* contains a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA. R* contains a bifunctional ligand preferably selected from one of the following acyclic chelating agents: EDTA, CyEDTA, EDTMP, DTPMP, DTPA, CyDTPA, Cy2DTPA, DTPA-MA, DTPA-BA, BOPA. R* contains a bifunctional ligand preferably selected from one of the following macrocyclic chelating agents: DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA.

R* contains a bifunctional chelating agent of the cationic, anionic, neutral or cleavable type.

R* contains a radionuclide preferably selected from $^{67}Cu$, $^{64}Cu$, $^{90}Y$, $^{109}Pd$, $^{111}Ag$, $^{149}Pm$, $^{153}Sm$, $^{166}Ho$, $^{177}Lu$, $^{186}Re$, $^{188}Re$, $^{99m}Tc$, $^{67}Ga$, $^{68}Ga$, $^{111}In$, $^{90}Y$, $^{177}Lu$, $^{186}Re$, $^{188}Re$, $^{197}Au$, $^{198}Au$, $^{199}Au$, $^{105}Rh$, $^{165}Ho$, $^{166}Ho$, $^{161}Tb$, $^{149}Pm$, $^{44}Sc$, $^{47}Sc$, $^{70}As$, $^{71}As$, $^{72}As$, $^{73}As$, $^{74}As$, $^{76}As$, $^{77}As$, $^{212}Pb$, $^{212}Bi$, $^{213}Bi$, $^{225}Ac$, $^{117m}Sn$, $^{67}Ga$, $^{201}Tl$, $^{123}I$, $^{131}I$, $^{160}Gd$, $^{148}Nd$, $^{89}Sr$, $^{211}At$, The products of formula (IA5) and (IB5) can also be used for non-invasive imaging techniques, used in diagnostics for measuring distribution and function in a biological system, of the PET (positron emission tomography) or SPECT (single photon emission computed tomography) type.

The products of formula (IA5) and (IB5) can also be used as radiopharmaceuticals, for example for treating a cancer.

In a particular embodiment of the invention, the products of formula (IA5) and (IB5) are used in non-invasive imaging techniques, used in diagnostics for measuring distribution and function in a biological system, of the PET (positron emission tomography) or SPECT (single photon emission computed tomography) type.

In another particular embodiment of the invention, the products of formula (IA5) and (IB5) are used as radiopharmaceuticals, for example for treating a cancer.

The invention also relates to a method for preparing the products of formula IB as defined above, characterized in that a product of formula IA

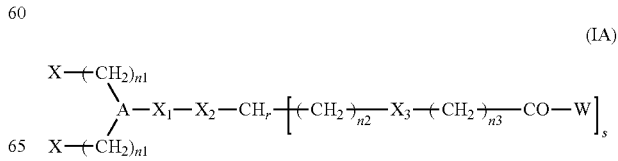

(IA)

where in formula (IA)
X is Br or I, or a

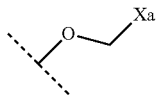

group, or a

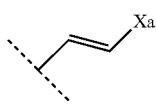

group, $X_a$ being a halogen or a nucleofuge.

A represents either an aryl or cycloalkyl radical, said aryl or cycloalkyl radicals being carbocyclic or heterocyclic,
or A represents a

group, a

group or a

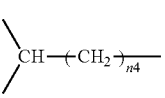

group
$X_1$ is a C=O or an NH group or a single bond
$X_2$ is an NH group or a C=O or a single bond
$X_3$ is an oxygen or a single bond
s is equal to 1, 2 or 3
r is equal to 0, 1 or 2
it being understood that the sum r+s is equal to 3
$n_1$ is an integer equal to 0 or 1; $n_2$ is an integer equal to 1, 2 or 3 and $n_3$ is an integer equal to 1, 2 or 3,
$n_4$ is an integer equal to 1, 2, 3 or 4,
W represents
an -L radical which represents a linker body comprising a terminal reactive function,
an —FL fluorophore group used in diagnostics or analysis, involving detection of fluorescence preferably selected from rhodamine or a derivative thereof, preferably rhodamine B, fluorescein isothiocyanate (FITC), a Cy dye preferably selected from Cy5, Cy5.5, Cy7, an Alexa fluor dye preferably selected from Alexa Fluor 647, 700 or 750, Texas Red, Nile Blue A, allophycocyanin (APC) and conjugates thereof with other fluorochromes in particular those mentioned above, phycoerythrin (PE) and conjugates thereof with other fluorochromes in particular those mentioned above, an R* radioactive radical, which preferably contains
either a bifunctional ligand, optionally bimodal, preferably selected from the derivatives of DOTA, DTPA, C-DOTA, NODAGA, NETA, C-NETA, DEPA, C-DEPA, TETA, TE2A, HYNIC, DAT, MAMA;
or a bifunctional ligand preferably selected from one of the acyclic chelating agents from the list constituted by EDTA, CyEDTA, EDTMP, DTPMP, DTPA, CyDTPA, $Cy_2DTPA$, DTPA-MA, DTPA-BA, BOPA;
or a bifunctional ligand preferably selected from one of the macrocyclic chelating agents from the list constituted by DOTA, TRITA, TETA, DOTA-MA, DO3A-HP, DOTMA, DOTA-pNB, DOTP, DOTMP, DOTEP, DOTMPE, F-DOTPME, DOTPP, DOTBzP, DOTA-monoamide, p-NCS-DOTA, p-NCS-PADOTA, BAT, DO3TMP-Monoamide, p-NCS-TRITA, NOTA, CHX-A"-DTPA;
or a bifunctional chelating agent of the cationic, anionic, neutral or cleavable type;
or a radionuclide preferably selected from $^{67}Cu$, $^{64}Cu$, $^{90}Y$, $^{109}Pd$, $^{111}Ag$, $^{149}Pm$, $^{153}Sm$, $^{166}Ho$, $^{177}Lu$, $^{186}Re$, $^{188}Re$, $^{99m}Tc$, $^{67}Ga$, $^{68}Ga$, $^{111}In$, $^{90}Y$, $^{177}Lu$, $^{186}Re$, $^{188}Re$, $^{197}Au$, $^{198}Au$, $^{199}Au$, $^{105}Rh$, $^{165}Ho$, $^{166}Ho$, $^{161}Tb$, $^{149}Pm$, $^{44}Sc$, $^{47}Sc$, $^{70}As$, $^{71}As$, $^{72}As$, $^{73}As$, $^{74}As$, $^{76}As$, $^{77}As$, $^{212}Pb$, $^{212}Bi$, $^{213}Bi$, $^{225}Ac$, $^{117m}Sn$, $^{67}Ga$, $^{201}Tl$, $^{123}I$, $^{131}I$, $^{160}Gd$, $^{148}Nd$, $^{89}Sr$, $^{211}At$,
a cytotoxic drug M selected from a chemotherapeutic agent or a toxin, in particular monomethyl auristatin E or monomethyl auristatin F,
an -L-M radical in which L and M have the meanings given above, in particular the

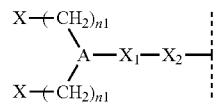

group is selected from the following radicals:

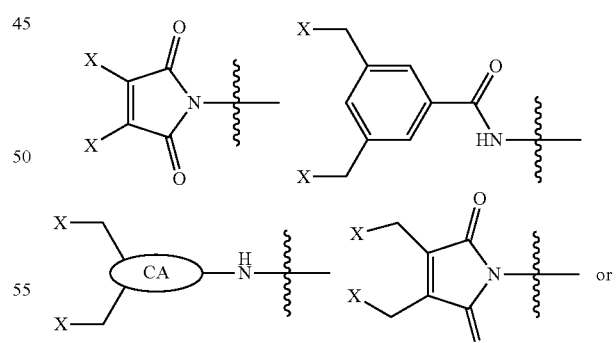

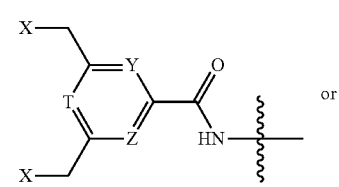

-continued

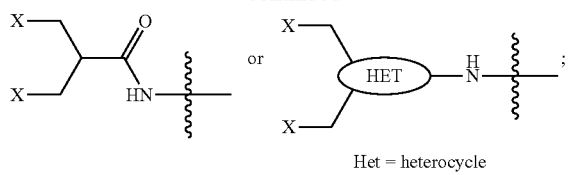

Het = heterocycle
or heteroaryl
or aryl as well as the derivatives of the carboxylic acid function or functions such as the salts, esters or amides, preferably the amide formed with butanimide, is reacted with a product of formula P, in which P is a protein comprising at least one disulphide bridge, in order to obtain a product of formula (IB):

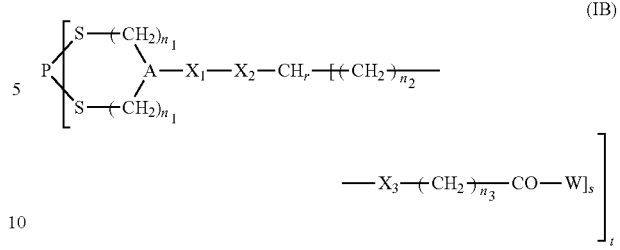

in which t represents an integer from 1 to 15, preferably from 1 to 6 and 13.

EXAMPLES

Example 1: Valine-Citrulline-Alcohol Para-Aminobenzyl Group

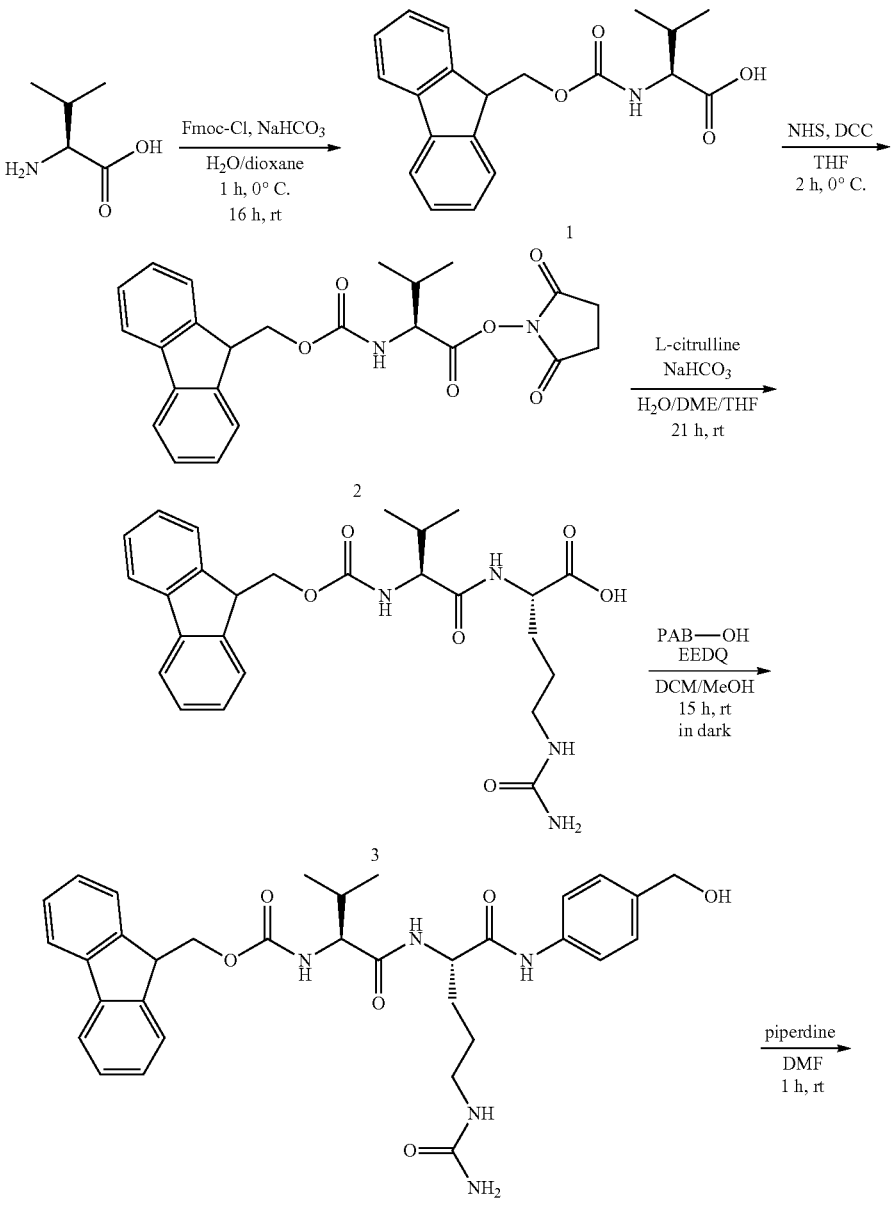

-continued

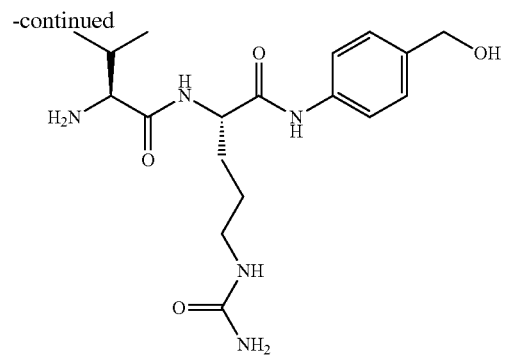

5

Valine (1.09 g, 9.31 mmol, 1 eq) is dissolved in 20 mL of water, and then 20 mL of dioxane and NaHCO$_3$ (1.56 g, 18.62 mmol, 2 eq) are added. The medium is cooled to 0° C., then Fmoc-Cl (2.65 g, 10.24 mmol, 1.1 eq) is introduced and the reaction is left for 1 h at 0° C. and then stirred overnight at ambient temperature. The next day, the reaction medium is acidified to pH=2 with 1M HCl solution and then extracted with EtOAc (3×60 mL). After evaporation under vacuum, the yellow oil obtained is purified by flash chromatography from 0 to 40% of EtOAc in cyclohexane. A white solid is obtained (2.23 g, 71%).

$^1$H NMR (300 MHz, CDCl$_3$): δ(ppm) 7.78-7.29 (m, 8H; Ar Fmoc), 5.25 (d, J=9.0 Hz, 1H; CONH Val), 4.43 (d, J=7.0 Hz, 2H; CH$_2$ Fmoc), 4.37 (dd, J=4.5 Hz, J=9.0 Hz, 1H; H$_α$ Val), 4.24 (t, J=7.0 Hz, 1H; CH Fmoc), 2.29-2.23 (m, 1H; H$_β$ Val), 1.02, 0.96 (2d, J=7.0 Hz, 6H; CH$_3$ Val)

$^{13}$C NMR (75 MHz, CDCl$_3$): δ(ppm) 176.50 (1C, COOH), 156.48 (1C, C=O Fmoc), 143.85, 141.47 (4C, C—Ar Fmoc), 127.89, 127.23, 125.21, 120.16 (8C, CH—Ar Fmoc), 67.27 (1C, CH$_2$ Fmoc), 58.93 (1C, C$_α$ Val), 47.32 (1C, CH Fmoc), 31.15 (1C, C$_β$ Val), 19.17, 17.59 (2C, CH$_3$ Val)

1.2. Synthesis of Fmoc-Val-OSu (2)

Fmoc-Val-OH (735 mg, 2.17 mmol, 1 eq) and N-hydroxysuccinimide (375 mg, 3.26 mmol, 1.5 eq) are dissolved in 5.5 mL of THF. DCC (448 mg, 2.17 mmol, 1 eq) is added at 0° C. and the reaction is stirred for 2 h at this temperature. The medium is then filtered on a frit and the solid is washed with THF (3×3 mL). The organic phase is dried over MgSO$_4$ and evaporated under vacuum and then purified by flash chromatography from 0 to 40% of EtOAc in cyclohexane in order to produce a colourless gum (865 mg, 91%).

HRMS: m/z calculated: 437.10671 [M+H]+, found: 437.17074.

$^1$H NMR (300 MHz, CDCl$_3$): δ(ppm) 7.78-7.29 (m, 8H; Ar Fmoc), 5.28 (d, J=9.0 Hz, 1H; CONH Val), 4.69 (dd, J=5.0 Hz, J=9.0 Hz, 1H; H$_α$ Val), 4.45 (d, J=7.0 Hz, 2H; CH$_2$ Fmoc), 4.24 (t, J=7.0 Hz, 1H; CH Fmoc), 2.84 (s, 4H; NCOCH$_2$), 2.40-2.29 (m, 1H; H$_β$ Val), 1.07, 1.05 (2d, J=7.0 Hz, 6H; CH$_3$ Val)

$^{13}$C NMR (75 MHz, CDCl$_3$): δ(ppm) 168.72, 167.87 (3C, C=O Su, C=O Val), 155.97 (1C, C=O Fmoc), 143.94, 143.72, 141.42 (4C, C—Ar Fmoc), 127.85, 127.23, 125.17, 120.10 (8C, CH—Ar Fmoc), 67.35 (1C, CH$_2$ Fmoc), 57.60 (1C, C$_α$ Val), 47.25 (1C, CH Fmoc), 31.75 (1C, C$_β$ Val), 25.69 (2C, CH$_2$C(O)NO), 18.82, 17.41 (2C, CH$_3$ Val)

1.3. Synthesis of Fmoc-Val-Cit-OH (3)

L-Citrulline (84 mg, 0.481 mmol, 1.05 eq) and NaHCO$_3$ (40 mg, 0.481 mmol, 1.05 eq) are dissolved in 1.2 mL of water and a solution of Fmoc-Val-OSu (200 mg, 0.458 mmol, 1 eq) in 1.2 mL of DME is added. To improve the solubility, 1.2 mL of THF is added and the medium is stirred for 21 h. 2.3 mL of 15% citric acid is added and the medium precipitates; it is extracted with a 10% iProH/EtOAc mixture (3×3 mL). The combined organic phases are washed with NaCl solution (2×4.5 mL), dried over MgSO$_4$ and then evaporated. When the white solid obtained is properly dry, it is washed with ether in order to produce an electrostatic white solid (140 mg, 62%).

HRMS: m/z calculated: 497.26142 [M+H]+, found: 497.23945.

$^1$H NMR (300 MHz, DMSO-d$_6$): δ(ppm) 12.50 (br s, 1H; COOH), 8.17 (d, J=7.5 Hz, 1H; CONH Cit), 7.88-7.27 (m, 9H; Ar Fmoc, CONH Val), 5.91 (t, J=5.5 Hz, 1H; NH Cit), 5.36 (s, 2H; NH$_2$ Cit), 4.25-4.07 (m, 4H; CH$_2$ Fmoc, CH Fmoc, H$_α$ Cit), 3.89 (dd, 7.0 Hz, J=9.0 Hz, 1H; H$_α$ Val), 2.94-2.88 (m, 2H; NCH$_2$ Cit), 1.97-1.88 (m, 1H; H$_β$ Val), 1.70-1.31 (m, 4H; CH$_2$ Cit), 0.86, 0.82 (2d, J=7.0 Hz, 6H; CH$_3$ Val)

$^{13}$C NMR (75 MHz, DMSO-d$_6$): δ(ppm) 173.45, 171.31 (2C, COOH, C=O Val), 158.76 (1C, NH$_2$CO Cit), 156.07 (1C, C=O Fmoc), 143.95, 143.80, 140.72 (4C, C—Ar Fmoc), 127.67, 127.09, 125.43, 120.11 (8C, CH—Ar Fmoc), 65.69 (1C, CH$_2$ Fmoc), 59.83 (1C, C$_α$ Val), 51.90 (1C, C$_α$ Cit), 46.69 (1C, CH Fmoc), 38.76 (1C, NCH$_2$ Cit), 30.56 (1C, C$_β$ Val), 28.38, 26.71 (2C, CH$_2$ Cit), 19.19, 18.24 (2C, CH$_3$ Val)

1.4. Synthesis of Fmoc-Val-Cit-PAB-OH (4)

Fmoc-Val-Cit-OH (518 mg, 1.04 mmol, 1 eq) and p-aminobenzyl alcohol (256 mg, 2.08 mmol, 2 eq) are dissolved in 18 mL of DCM/MeOH 2/1 and EEDQ (514 mg, 2.08 mmol, 2 eq) is added. The medium is stirred for 15 h in the dark at ambient temperature. The solvents are evaporated, and the yellow solid obtained is triturated with ether. The suspension is sonicated for 5 min and left to stand for 30 min. It is then filtered and the solid is rinsed several times with ether in order to produce a yellow powder (559 mg, 89%).

HRMS: m/z calculated: 601.85499 [M+H]+, found: 602.29758.

$^1$H NMR (300 MHz, DMSO-d$_6$): δ(ppm) 9.97 (s, 1H; NH PAB), 8.10 (d, J=7.0 Hz, 1H; CONH Cit), 7.87-7.18 (m, 13H; Ar Fmoc, Ar PAB, CONH Val), 5.95 (br t, J=5.5 Hz, 1H; NH Cit), 5.40 (s, 2H; NH$_2$ Cit), 5.09 (t, J=5.5 Hz, 1H; OH PAB), 5.39 (d, J=5.5 Hz, 1H; CH$_2$ PAB), 4.27-4.19 (m, 4H; CH$_2$ Fmoc, CH Fmoc, Hα Cit), 3.89 (dd, J=8.0 Hz, J=8.0 Hz, 1H; H$_α$ Val), 3.03-2.84 (m, 2H; NCH$_2$ Cit), 1.98-1.92 (m, 1H; H$_β$ Val), 1.69-1.27 (m, 4H; CH$_2$ Cit), 0.84, 0.82 (2d, J=7.0 Hz, 6H; CH$_3$ Val)

$^{13}$C NMR (75 MHz, DMSO-$d_6$): δ(ppm) 171.30, 170.43 (2C, C=O Cit, C=O Val), 158.94 (1C, NH$_2$CO Cit), 156.17 (1C, C=O Fmoc), 143.94, 143.81, 140.75 (4C, C—Ar Fmoc), 137.55, 137.48 (2C, C—Ar PAB), 127.70, 127.13, 125.40, 120.14 (8C, CH—Ar Fmoc), 126.98, 118.91 (4C, CH—Ar PAB), 65.73 (1C, CH$_2$ Fmoc), 62.63 (1C, CH$_2$ PAB), 60.14 (1C, C$_α$ Val), 53.11 (1C, C$_α$ Cit), 46.72 (1C, CH Fmoc), 38.96 (1C, NCH$_2$ Cit), 30.48 (1C, C$_β$ Val), 29.57, 26.81 (2C, CH$_2$ Cit), 19.26, 18.31 (2C, CH$_3$ Val)

1.5. Synthesis of H-Val-Cit-PAB-OH (5)

Fmoc-Val-Cit-PAB-OH (298 mg, 0.495 mmol, 1 eq) is dissolved in 4 mL of DMF and 1 mL of piperidine is added. After reaction for 1 h the medium is evaporated. The viscous solid obtained is triturated with DCM in order to produce a beige solid after filtration (189 mg, 100%).

HRMS: m/z calculated: 601.85499 [M+H]+, found: 602.29758.

$^1$H NMR (300 MHz, DMSO-$d_6$): δ(ppm) 10.04 (s, 1H; NH PAB), 8.16 (d, J=7.5 Hz, 1H; CONH Cit), 7.52, 7.22 (2d, J=8.5 Hz, 4H; Ar PAB), 5.97 (br t, J=5.5 Hz, 1H; NH Cit), 5.40 (s, 2H; NH$_2$ Cit), 5.10 (br t, J=5.5 Hz, 1H; OH PAB), 4.46-4.40 (m, 3H; CH$_2$ PAB, H$_α$ Cit), 3.52-3.18 (NH$_2$ Val, water), 3.05-2.87 (m, 3H; H$_α$ Val, NCH$_2$ Cit), 1.95-1.89 (m, 1H; H$_β$ Val), 1.71-1.28 (m, 4H; CH$_2$ Cit), 0.87, 0.77 (2d, J=7.0 Hz, 6H; CH$_3$ Val)

$^{13}$C NMR (75 MHz, DMSO-$d_6$): δ(ppm) 170.48 (2C, C=O Cit, C=O Val), 158.86 (1C, NH$_2$CO Cit), 137.52, 137.43 (2C, C—Ar PAB), 126.94, 118.95 (4C, CH—Ar PAB), 62.59 (1C, CH$_2$ PAB), 59.50 (1C, C$_α$ Val), 52.53 (1C, C$_α$ Cit), 38.08 (1C, NCH$_2$ Cit), 31.25 (1C, C$_β$ Val), 30.10, 26.70 (2C, CH2 Cit), 19.46, 16.96 (2C, CH$_3$ Val)

Example 2: Maleimide Derivative as Bioconjugation Head

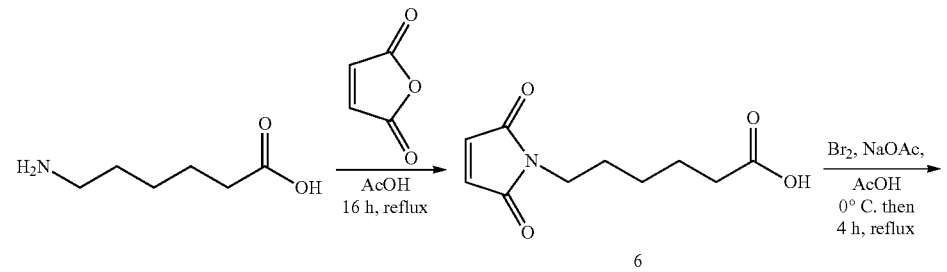

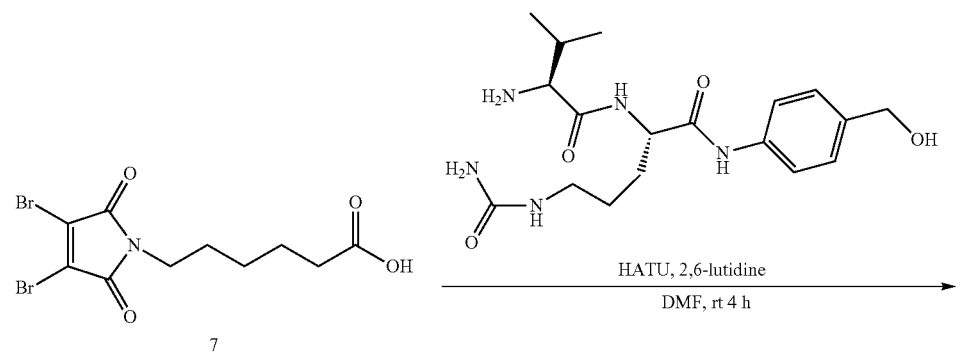

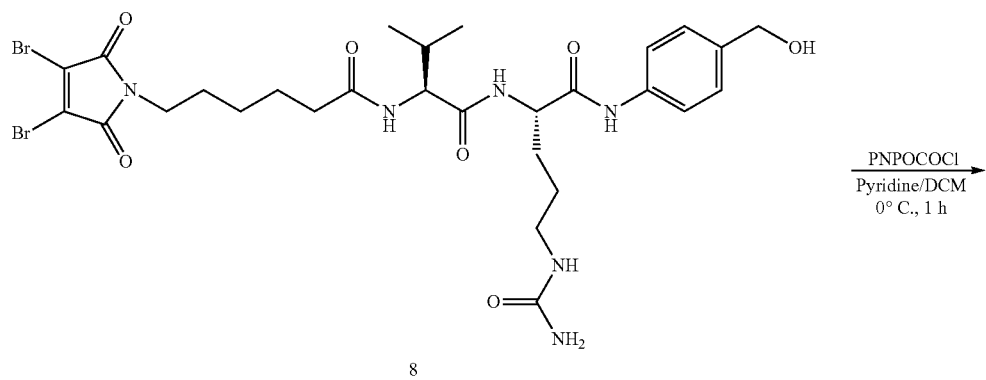

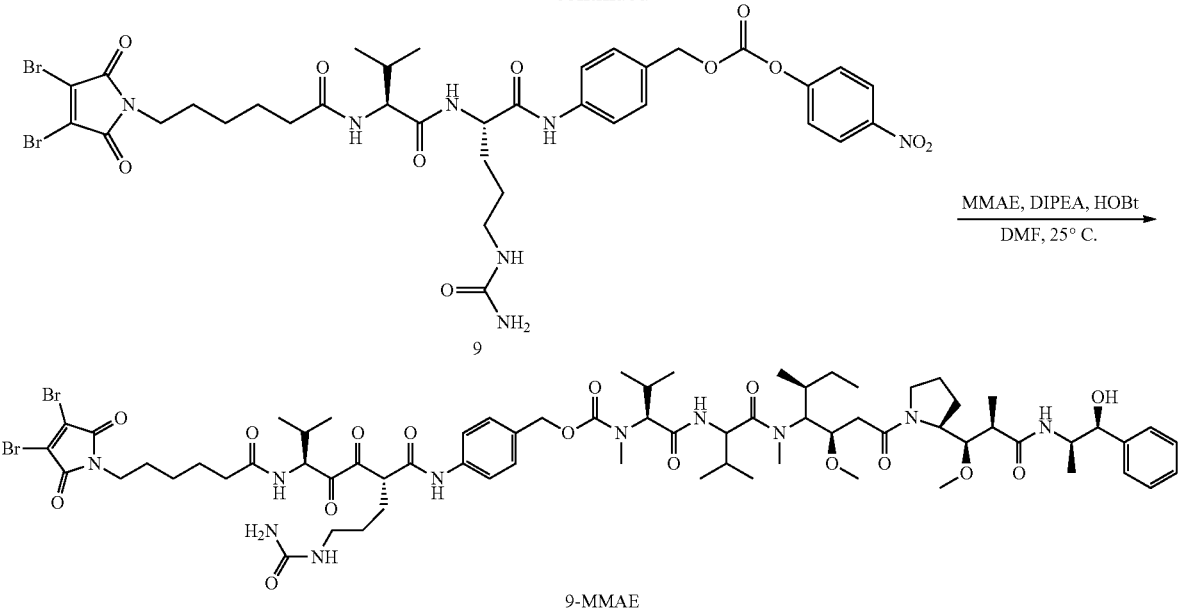

9-MMAE

2.1. Synthesis of 6-maleimidohexanoic Acid (6)

Maleic anhydride (1.50 g, 15.25 mmol, 1 eq) and 6-aminocaproic acid (2.00 g, 15.25 mmol, 1 eq) are stirred under argon in 15 mL of acetic acid. The reaction medium is heated under reflux and stirred overnight. The next day, the mixture has turned orange. The acetic acid is coevaporated three times with 75 mL of toluene and a viscous orange-coloured oil is obtained; it is taken up in 150 mL of DCM and then washed with 150 mL of water. The aqueous phase is extracted again (2×150 mL) and the combined organic phases are dried over $MgSO_4$ and then evaporated under vacuum in order to produce an orange-coloured solid (2.60 g, 81%).

HRMS: m/z calculated: 216.95765 [M+H]% found: 217.09071.

$^1$H NMR (300 MHz, $CDCl_3$): δ(ppm) 6.69 (s, 2H; CH═CH), 3.51 (t, J=7.0 Hz, 2H; $NCH_2$), 2.34 (t, J=7.5 Hz, 2H; $CH_2COOH$), 1.70-1.55 (m, 4H; $NCH_2CH_2CH_2CH_2$), 1.38-1.28 (m, 2H; $NCH_2CH_2CH_2$)

$^{13}$C NMR (75 MHz, $CDCl_3$): δ(ppm) 179.53 (1C, COOH), 171.00 (2C, C═O MC), 134.21 (2C, CH═CH), 37.71 (1C, $NCH_2$), 33.86 (1C, $CH_2COOH$), 28.30 (1C, $NCH_2CH_2$), 26.24 (1C, $NCH_2CH_2CH_2$), 24.21 (1C, $CH_2CH_2COOH$)

2.2. Synthesis of 6-(3,4-dibromomaleimido)hexanoic Acid (7)

Maleimidohexanoic acid (200 mg, 0.947 mmol, 1 eq) and sodium acetate (117 mg, 1.421 mmol, 1.5 eq) are put in a tube under argon and 2.9 mL of acetic acid is added. Dibromine (0.07 mL, 1.421 mmol, 1.5 eq) is added at 0° C., the tube is sealed and then heated under reflux for 4 h. The medium is then left to return to ambient temperature and 16 mL of iced water is added. The aqueous phase is extracted with EtOAc (3×20 mL) and the combined organic phases are washed with 40 mL of a solution of sodium thiosulphate, dried over $MgSO_4$, and coevaporated with toluene. The brown residue obtained is purified by flash chromatography from 0 to 40% of EtOAc in cyclohexane in order to produce a yellow solid (237 mg, 68%).

HRMS: m/z calculated: 368.47706 [M+H]+, found: 367.91255

$^1$H NMR (300 MHz, $CDCl_3$): δ(ppm) 3.62 (t, J=7.0 Hz, 2H; $NCH_2$), 2.36 (t, J=7.5 Hz, 2H; $CH_2COOH$), 1.72-1.59 (m, 4H; $NCH_2CH_2CH_2CH_2$), 1.42-1.31 (m, 2H; $NCH_2CH_2CH_2$)

$^{13}$C NMR (75 MHz, $CDCl_3$): δ(ppm) 178.18 (1C, COOH), 164.10 (2C, C═O MC), 129.50 (2C, C═C), 39.63 (1C, $NCH_2$), 33.60 (1C, $CH_2COOH$), 28.25 (1C, $NCH_2CH_2$), 26.16 (1C, $NCH_2CH_2CH_2$), 24.17 (1C, $CH_2CH_2COOH$)

2.3. Synthesis of 6-(3,4-dibromomaleimido)hexanamide-Val-Cit-PAB-OH (8)

6-(3,4-Dibromomaleimido)hexanoic acid (178 mg, 0.482 mmol, 1 eq) and HATU (238 mg, 0.627 mmol, 1.3 eq) are dissolved in 2.2 mL of anhydrous DMF and then 2,6-lutidine (73 µL, 0.627 mmol, 1.3 eq) is added. The medium is stirred for 1 h, then dipeptide (183 mg, 0.482 mmol, 1 eq) is added and the reaction is left overnight with stirring. 1.6 mL of 1M HCl is then added and the aqueous phase is extracted twice with EtOAc. The combined organic phases are washed three times with saturated NaCl solution, and then evaporated. The residue obtained is purified by silica gel column chromatography with a gradient of DCM/MeOH eluent from 15/1 to 9/1 in order to produce a yellow solid (84 mg, 24%).

HRMS: m/z calculated: 729.15941 [M+H]+, found: 729.12412.

$^1$H NMR (300 MHz, DMSO-$d_6$): δ(ppm) 9.91 (s, 1H; NH PAB), 8.08 (d, J=8.0 Hz, 1H; CONH Cit), 7.83 (d, J=8.5 Hz, 1H; CONH Val), 7.54, 7.22 (2d, J=8.5 Hz, 4H; Ar PAB), 5.98 (br t, J=5.5 Hz, 1H; NH Cit), 5.42 (s, 2H; $NH_2$ Cit), 5.15-5.07 (m, 1H; OH PAB), 4.42-4.33 (m, 3H; $CH_2$ PAB, $H_α$ Cit), 4.19 (dd, J=7.0 Hz, J=8.5 Hz, 1H; $H_α$ Val), 3.46-3.27 ($NCH_2$ MC, water), 3.05-2.89 (m, 2H; $NCH_2$ Cit), 2.23-2.08 (m, 2H; $CH_2CO$ MC), 2.01-1.91 (m, 1H; $H_β$ Val), 1.73-1.16 (m, 10H; $CH_2$ Cit, $NCH_2CH_2CH_2CH_2$), 0.85, 0.81 (2d, J=7.0 Hz, 6H; $CH_3$ Val)

$^{13}$C NMR (75 MHz, DMSO-$d_6$): δ(ppm) 172.33, 171.28, 170.39, 163.13 (5C, C═O Cit, C═O Val, C═O MC), 158.92 (1C, $NH_2CO$ Cit), 137.54, 137.42 (2C, C—Ar PAB), 132.30 (2C, C=C), 126.94, 118.86 (4C, CH—Ar PAB), 62.60 (1C, CH$_2$ PAB), 57.61 (1C, C$_\alpha$ Val), 53.08 (1C, C$_\alpha$ Cit), 38.96 (1C, NCH$_2$ MC), 38.68 (1C, NCH$_2$ Cit), 34.94 (1C, CH$_2$CO MC), 30.39 (1C, C$_\beta$ Val), 29.39, 27.55, 26.78, 25.70, 24.91 (5C, NCH$_2$CH$_2$CH$_2$CH$_2$, CH$_2$ Cit), 19.26, 18.18 (2C, CH$_3$ Val)

2.4. Synthesis of 6-(3,4-dibromomaleimido)hexanamide-Val-Cit-PAB-OCOOPNP (9)

6-(3,4-Dibromomaleimido)hexanamide-Val-Cit-PAB-OH (42 mg, 57.5 µmol, 1 eq) is dissolved in 0.85 mL of anhydrous pyridine. PNPOCOCl (35 mg, 172.5 µmol, 3 eq) is dissolved in 0.6 mL of anhydrous DCM and then added to the solution of 6-(3,4-dibromomaleimido)hexanamide-Val-Cit-PAB-OH in pyridine at 0° C. After 1 h there is no longer any of the starting product. The pyridine is coevaporated three times with toluene and then the residue is purified by column chromatography with a gradient of DCM/MeOH eluent from 15/1 to 8/2 in order to produce an orange-coloured solid (5.9 mg, 11%).

The product is used directly for grafting on the molecule of interest (i.e. drug, fluorochrome, etc.).

2.5. Synthesis of 6-(3,4-dibromomaleimido)hexanamide-Val-Cit-PAB-MMAE (9-MMAE)

6-(3,4-Dibromomaleimido)hexanamide-Val-Cit-PAB-OCOOPNP (9.0 mg, 10 µmol, 1 eq) is dissolved under argon at 25° C. in 1 mL of anhydrous DMF/pyridine mixture: 4/1. DIPEA (1.4 µL, 1.2 eq), HOBt (1.83 mg, 1 eq) and MMAE (7.2 mg, 10 µmol, 1 eq) are added to this solution successively. The mixture is stirred for 24 h (monitoring with HPLC) and the crude reaction product is purified by semi-preparative HPLC in order to provide the linker 9-MMAE (4.3 mg, 29%) in the form of yellow solid, the conformity of which is verified by mass spectroscopy.

Example 3: Benzene Derivative as Bioconjugation Head

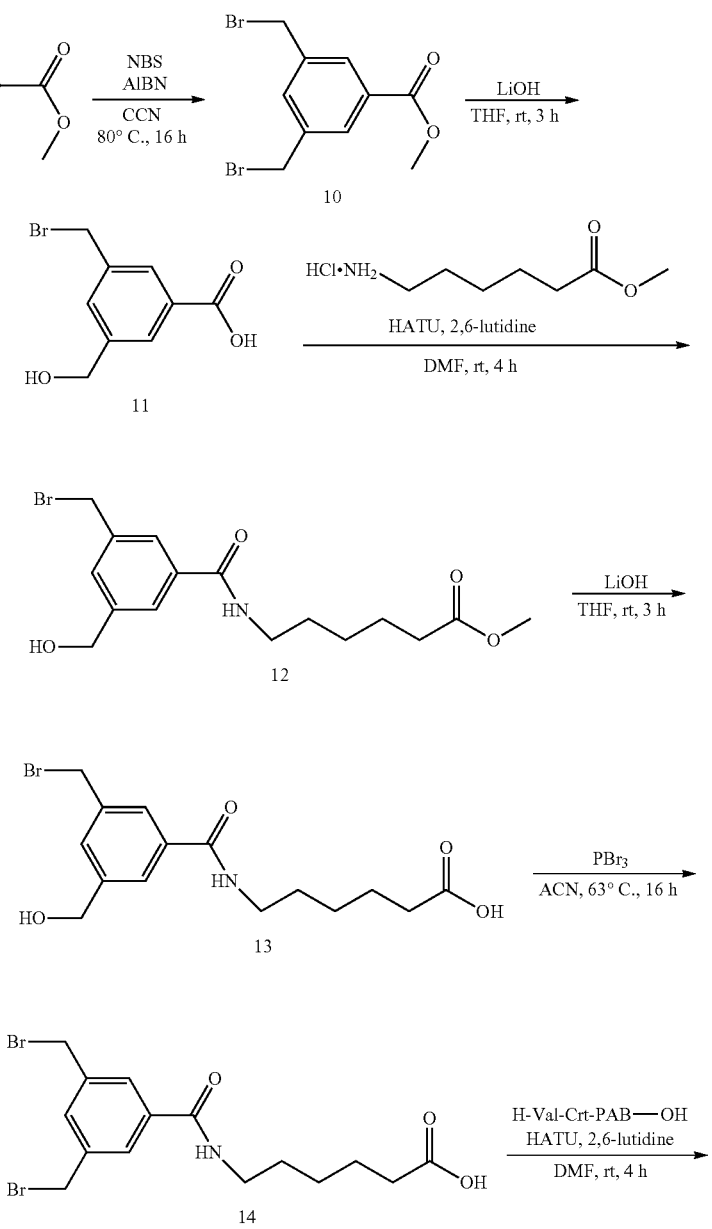

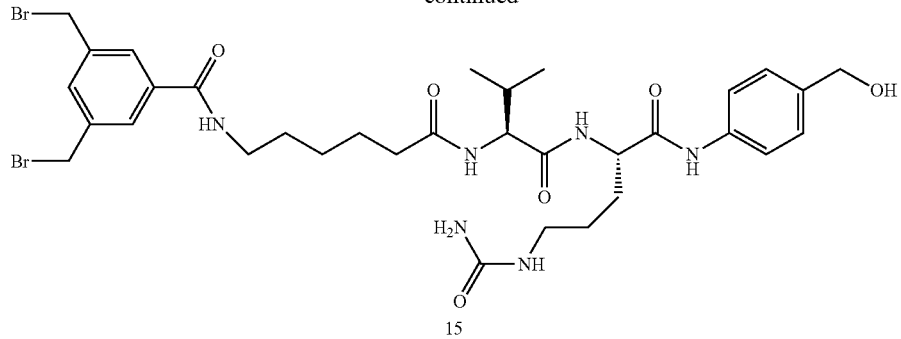

3.1. Methyl 3,5-bis(bromomethyl)benzoate (10)

Methyl 3,5-bis(bromomethyl)benzoate (1.00 g, 6.09 mmol, 1 eq) is dissolved in anhydrous CCl₄ (25 mL) and the mixture is heated under reflux. NBS (2.38 g, 13.40 mmol, 2.2 eq) is added in five equal portions over 8 h followed by the addition of a few milligrams of Bz₂O₂. The mixture is stirred overnight and then filtered. The filtrate is washed with water (50 mL), saturated NaHCO₃ solution (25 mL) and brine (30 mL). The organic layer is dried over MgSO₄ and evaporated. The residue is dissolved in 25 ml of anhydrous THF and diethyl phosphite (1.7 mL, 13.40 mmol, 2.2 eq) and anhydrous DIPEA (2.3 mL, 13.40 mmol, 2.2 eq) is added at 0° C. The mixture is then stirred at ambient temperature for two days. It is evaporated and 50 mL of iced water is added and extracted with ether (3×25 mL). The combined organic layers are washed with 1M HCl solution (25 mL), brine (25 mL) and are dried over MgSO₄. Evaporation of the solvent under reduced pressure produced a residue, which is purified by flash chromatography in a gradient of cyclohexane at 5% of EtOAc in cyclohexane in order to produce 10 in the form of a white solid (0.83 g, 42%).

¹H NMR (300 MHz, CDCl₃): δ(ppm) 8.00 (d, J=2.0 Hz, 2H; H-2, H-6), 7.62 (t, J=2.0 Hz, 1H; H-4), 4.50 (s, 4H; CH₂Br), 3.94 (s, 3H; COCH₃).

¹³C NMR (75 MHz, CDCl₃): δ(ppm) 166.07 (1C, COO), 139.09 (2C, C-3, C-5), 134.00 (1C, CH-4), 131.55 (1C, C-1), 130.18 (2C, CH-2, CH-6), 52.57 (1C, OCH₃), 31.99 (2C, CH₂Br).

3.2. General Procedure 1 for Saponification with Lithium Hydroxide:

The ester (1 mmol) is dissolved in THF (20 mL), and LiOH is added (2.5 eq). The reaction mixture is stirred at ambient temperature until the end of the reaction (generally 3 h, verified by monitoring with TLC). Then 1M of HCl is added until the pH of the solution becomes acid (pH=2), and the mixture is extracted with EtOAc (3×25 mL). The combined organic layers are dried over MgSO₄. Evaporation of the solvent under reduced pressure makes it possible to obtain the corresponding acid.

3.3. General Procedure 2 for Peptide Coupling Using HATU:

The acid (0.2 mmol) is dissolved in anhydrous DMF (1 mL) under argon, to which HATU (1.2 eq) and 2,6-lutidine (1.3 eq) are added at ambient temperature. The reaction mixture is stirred for 15 to 40 min at ambient temperature, then a solution of amine (1.0 eq) in DMF (1 mL) is added, and the mixture is stirred until the end of the reaction (typically 4 hours) at ambient temperature under argon. Then the mixture is diluted by adding a solution of 15% citric acid and EtOAc, and then filtered. The filtrate is extracted three times with EtOac, washed with saturated solutions of NaCl and NaHCO₃. The organic layer is dried (MgSO₄) and evaporated under reduced pressure. The crude product is purified by flash chromatography in order to produce the desired amide.

3.4. General Procedure 3 for Bromination Using Phosphorus Tribromide:

The alcohol is dissolved in anhydrous ACN under argon, then PBr3 is added and the reaction mixture is heated at 60° C. under argon for 16 h. After cooling, the reaction mixture is diluted with water, and extracted three times with EtOAc. The combined organic layers are washed with brine and dried over MgSO₄. Evaporation of the solvent under reduced pressure produced the desired corresponding brominated compound.

3.5. 3-(Bromomethyl)-5-(hydroxymethyl)benzoic acid (11)

Compound 11 is prepared from 10 (317 mg, 0.98 mmol) by general procedure 1 in order to produce 11 (160 mg, 66%) in the form of a white solid.

¹H NMR (300 MHz, CDCl₃): δ(ppm) 8.21-7.97 (m, 2H, H$_{arom}$), 7.69 (d, J=2.0 Hz, 1H, H$_{arom}$), 4.64 (d, J=3.0 Hz, 2H, CH₂OH), 4.53 (d, J=3.0 Hz, 2H, CH₂Br).

¹³C NMR (75 MHz, CDCl₃): δ(ppm) 170.10 (1C, COO), 139.34 (1C, C-5), 137.86 (1C, C-3), 134.91 (1C, CH-4), 134.45 (1C, C-1), 130.71 (1C, C-2), 130.28 (1C, C-3), 45.10 (1C, CH₂OH), 31.81 (1C, CH₂Br).

3.6. Methyl 6-(3-(bromomethyl)-5-(hydroxymethyl)benzamido)hexanoate (12)

Compound 12 is prepared from 11 (50 mg, 0.20 mmol) by general procedure 2 in order to produce 12 (41 mg, 54%) in the form of a white solid.

¹H NMR (300 MHz, CDCl₃): δ(ppm) 7.78-7.50 (m, 3H, H$_{arom}$), 6.35 (s, 1H, NH), 4.60 (d, J=3.1 Hz, 2H, CH₂OH), 4.49 (d, J=3.1 Hz, 2H, CH₂Br), 3.66 (s, 3H, CH₃), 3.47 (dd, J=13.0, 6.9 Hz, 2H, CH₂-5), 2.34 (t, J=7.3 Hz, 2H, CH₂-1), 1.78-1.54 (m, 4H, CH₂-2, CH₂-3), 1.52-1.33 (m, 2H, CH₂-4).

¹³C NMR (75 MHz, CDCl₃): δ(ppm) 174.28 (1C, COO), 166.53 (1C, CONH), 139.08 (1C, C$_{Ar}$-5), 138.75 (1C, C$_{Ar}$-3), 136.08 (1C, C$_{Ar}$-1), 131.98 (1C, C$_{Ar}$-2), 127.62 (1C, C$_{Ar}$-2), 127.17 (1C, C$_{Ar}$-6), 51.71 (1C, CH₂OH), 45.36 (1C, CH-5), 39.90 (1C, CH-1), 33.88 (1C, CH₂Br), 32.19 (1C, CH₃), 29.21 (1C, CH-2), 26.40 (1C, CH-3), 24.37 (1C, CH-4).

3.7. 6-(3-(Bromomethyl)-5-(hydroxymethyl)benzamido)hexanoic acid (13)

Compound 13 is prepared from 12 (215 mg, 0.58 mmol) by general procedure 1 in order to produce 13 (160 mg, 77%) in the form of an electrostatic white solid.

HRMS: m/z calculated: 356.0576 [M+H]+, found: 356.0578.

$^1$H NMR (300 MHz, DMSO-d$_6$): δ(ppm) 12.0 (bs, 1H, COOH), 8.57 (t, J=5.5 Hz, 1H, NH), 7.92-7.61 (m, 3H, H$_{arom}$), 4.90-4.67 (m, 4H, CH$_2$Br, CH$_2$OH), 3.24 (dd, J=12.8, 6.8 Hz, 2H, CH$_2$-5), 2.21 (t, J=7.3 Hz, 2H, CH$_2$-1), 1.62-1.42 (m, 4H, CH$_2$-2, CH$_2$-3), 1.40-1.23 (m, 2H, CH$_2$-4).

$^{13}$C NMR (75 MHz, CDCl$_3$): δ(ppm) 174.50 (1C, COO), 165.21 (1C, CONH), 138.35 (1C, C$_{Ar}$-5), 135.60 (1C, C$_{Ar}$-3), 133.92 (1C, C$_{Ar}$-1), 131.59 (1C, C$_{Ar}$-2), 127.58 (1C, C$_{Ar}$-6), 45.48 (1C, CH$_2$OH), 39.15 (1C, CH-5), 33.62 (2C, CH-1, CH$_2$Br), 28.81 (1C, CH-2), 26.05 (1C, CH-3), 24.27 (1C, CH-4).

3.8. 6-(3,5-bis(Bromomethyl)benzamido)hexanoic acid (14)

Compound 14 is prepared from 13 (20 mg, 0.006 mmol) by general procedure 3 in order to produce 14 (24 mg, quantitative) in the form of an off-white solid.

HRMS: m/z calculated: 419.9732 [M+H]+, found: 419.9808.

$^1$H NMR (300 MHz, DMSO-d$_6$): δ(ppm) 11.8 (bs, 1H, COOH), 8.57 (s, 1H, NH), 7.92-7.62 (m, 3H, H$_{arom}$), 4.78 (dd, J=20.8, 3.3 Hz, 4H, 2×CH$_2$Br), 3.32-3.06 (m, 2H+water, CH$_2$-5), 2.21 (t, J=7.3 Hz, 2H, CH$_2$-1), 1.65-1.41 (m, 4H, CH$_2$-2, CH$_2$-3), 1.40-1.23 (m, 2H, CH$_2$-4).

$^{13}$C NMR (75 MHz, DMSO-d$_6$): δ(ppm) 174.50 (1C, COO), 165.21 (1C, CONH), 138.37 (1C, C$_{Ar}$-5), 135.58 (1C, C$_{Ar}$-3), 132.00 (1C, C$_{Ar}$-1), 131.58 (1C, C$_{Ar}$-2), 127.58 (1C, C$_{Ar}$-6), 45.57 (1C, CH$_2$OH), 39.08 (1C, CH-5), 33.73 (3C, CH-1, CH$_2$Br), 28.89 (1C, CH-2), 26.04 (1C, CH-3), 24.32 (1C, CH-4).

3.9. 6-(3,5-bis(Bromomethyl)benzamido)hexanamide-Val-Cit-PAB-OH (15) Compound 15 is prepared from 14 (124 mg, 0.29 mmol) by general procedure 2 in order to produce 15 (30 mg, 13%) in the form of a beige solid.

HRMS: m/z calculated: 781.1846 [M+H]+, found: 781.1907.

$^1$H NMR (300 MHz, DMSO-d$_6$): δ(ppm) 9.95 (s, 1H, NH PAB), 8.71-8.50 (m, 1H, CONH Cit), 8.10 (d, J=7.5 Hz, 1H, CONH Val), 8.04-7.55 (m, 3H, H$_{arom}$), 7.55, 7.22 (2d, J=8.5 Hz, 4H, Ar PAB), 6.06 (t, J=5.6 Hz, 1H, NH Cit), 5.45 (br s, 2H, NH$_2$ Cit), 5.12 (br s, 1H, OH PAB), 4.82 (s, 4H, 2×CH$_2$Br), 4.46-4.32 (m, 3H, CH$_2$ PAB, H$_α$ Cit), 4.26-4.13 (m, 1H, H$_α$ Val), 3.24 (dd, J=12.8, 6.6 Hz, CH$_2$-5), 3.10-2.84 (m, 2H, NCH$_2$ Cit), 2.29-2.07 (m, 2H, CH$_2$-1), 1.97 (dq, J=13.7, 6.6 Hz, 1H, H$_β$ Val), 1.80-1.05 (m, 10H, CH$_2$CH$_2$ Cit, NCH$_2$CH$_2$CH$_2$), 0.83 (dd, J=8.9, 7.0 Hz, 6H, CH$_3$ Val).

$^{13}$C NMR (75 MHz, DMSO-d$_6$): δ(ppm) 172.44, 171.29, 170.42, 165.18, 165.02, 158.94, 151.89, 151.12, 139.24, 138.32, 138.28, 137.56, 137.41, 135.59, 135.45, 134.46, 133.79, 132.58, 131.55, 129.41, 128.86, 128.73, 128.60, 127.59, 126.92, 121.31, 120.73, 118.86, 81.78, 62.60, 57.67, 53.08, 48.61, 45.49, 45.36, 38.56, 35.17, 30.37, 29.36, 28.86, 26.79, 26.19, 25.23, 19.26, 18.23.

Example 4: Pyridine Derivative as Bioconjugation Head

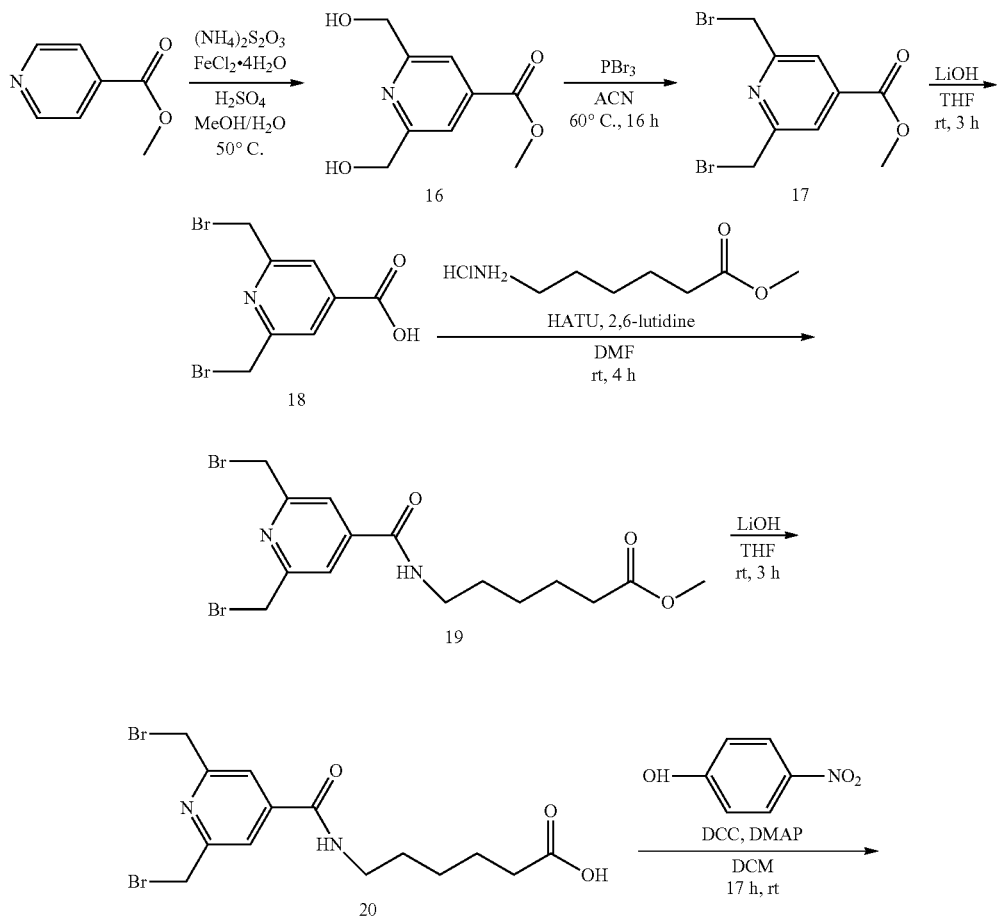

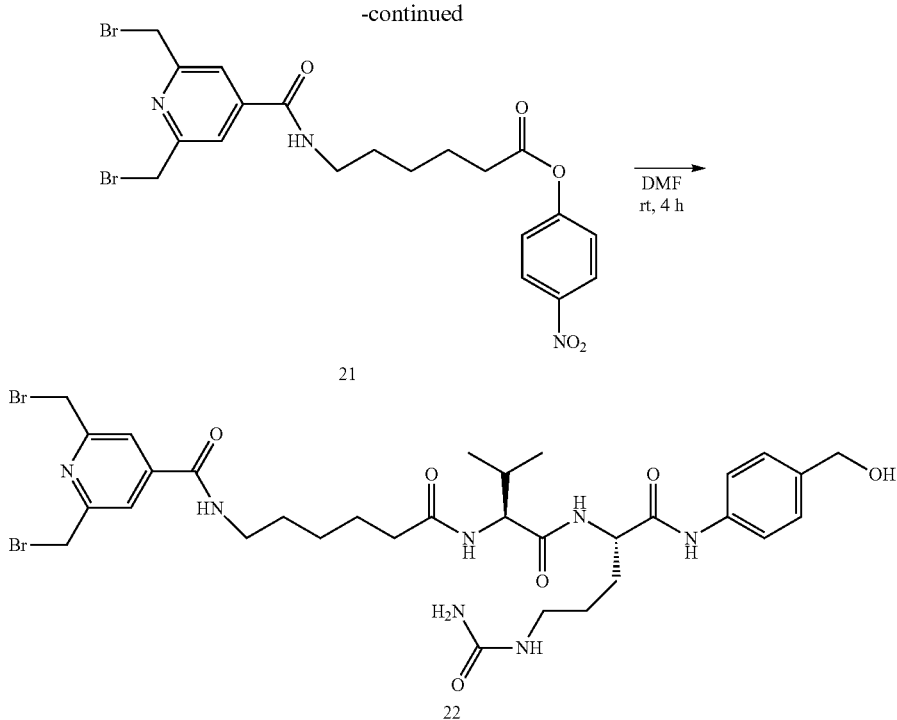

4.1. Methyl 2,6-bis(hydroxymethyl)isonicotinate (16)

Methylisonicotinate (2.12 mL, 18 mmol) is dissolved under argon in a mixture of MeOH/H$_2$O: 1/1 (40 mL), then H$_2$SO$_4$ (78 µl) is added and the mixture is stirred for 30 min. Then ammonium persulphate (32 g, 144 mmol) and iron chloride tetrahydrate (0.89 g, 4.5 mmol) are added carefully at 0° C. and the mixture is heated at 50° C. overnight. After the reaction mixture has cooled, the suspension is filtered and the solid is washed with a small quantity of EtOAc. The filtrate is concentrated under reduced pressure until all the MeOH has been removed. The medium is made basic with Na$_2$CO$_3$ and is then extracted with EtOAc. The organic layer is dried over MgSO$_4$, filtered and concentrated under reduced pressure. The crude product is purified by flash chromatography in a DCM gradient of 10% of MeOH in DCM in order to produce 16 in the form of a dark brown solid (0.54 g, 15%).

$^1$H NMR (300 MHz, CDCl$_3$): δ(ppm) 7.82 (s, 2H, H$_{arom}$), 4.88 (s, 4H, CH$_2$OH), 3.98 (s, 3H, CH$_3$).

$^{13}$C NMR (75 MHz, CDCl$_3$): δ(ppm) 165.57 (1C, COOCH$_3$), 160.00 (1C, C-1), 150.47 (2C, C-3, C-5), 118.77 (2C, C-2, C-6), 64.54 (2C, CH$_2$OH), 52.98 (1C, CH$_3$).

4.2. Methyl 2,6-bis(bromomethyl)isonicotinate (17)

Compound 17 is prepared from 16 (120 mg, 061 mmol) by general procedure 3 in order to produce 17 (141 mg, 72%) in the form of a light pink solid.

$^1$H NMR (300 MHz, CDCl$_3$): δ(ppm) 7.92 (s, 2H, H$_{arom}$), 4.58 (s, 4H, CH$_2$Br), 3.98 (s, 3H, CH$_3$).

$^{13}$C NMR (75 MHz, CDCl$_3$): δ(ppm) 164.8 (1C, COOCH$_3$), 158.0 (1C, C-1), 139.8 (2C, C-3, C-5), 122.3 (2C, C-2, C-6), 53.0 (1C, CH$_3$), 32.8 (2C, CH$_2$Br).

4.3. 2,6-bis(Bromomethyl)isonicotinic acid (18)

Compound 18 is prepared from 17 (137 mg, 0.42 mmol) by general procedure 1 in order to produce 18 (133 mg, quantitative) in the form of an orange-coloured solid.

HRMS: m/z calculated: 307.88441 [M+H]+, found: 307.8917.

$^1$H NMR (300 MHz, DMSO-d$_6$): δ(ppm) 7.92 (s, 2H, Harem), 4.79 (s, 4H, CH$_2$Br), 3.35 (s, 3H, CH$_3$).

$^{13}$C NMR (75 MHz, DMSO-d$_6$): δ(ppm) 165.9 (1C, COOCH$_3$), 158.6 (1C, C-1), 141.0 (2C, C-3, C-5), 122.7 (2C, C-2, C-6), 34.3 (2C, CH$_2$Br).

4.4. Methyl 6-(2,6-bis(bromomethyl)isonicotinamido)hexanoate (19)

Compound 19 is prepared from 18 (260 mg, 0.84 mmol) by general procedure 2 in order to produce 19 (218 mg, 59%) in the form of a yellow solid.

HRMS: m/z calculated: 434.9841 [M+H]+, found: 434.9906.

$^1$H NMR (300 MHz, CDCl$_3$): δ(ppm) 7.70 (s, 2H, H$_{arom}$), 6.41 (s, 1H, NH), 4.58 (s, 4H, CH$_2$Br), 3.69 (s, 3H, OCH$_3$), 3.50 (dd, J=13.5, 7.0 Hz, 2H, CH$_2$-5), 2.36 (t, J=7.0 Hz, 2H, CH$_2$-1), 1.68 (dq, J=13.5, 7.0 Hz, 4H, CH$_2$-2, CH$_2$-4), 1.54-1.34 (m, 2H, CH$_2$-3).

$^{13}$C NMR (75 MHz, CDCl$_3$): δ(ppm) 173.1 (1C, COOCH$_3$), 157.8 (1C, CONH), 155.0 (2C$_{pyridine}$, C-4, C-6), 120.3 (2C$_{pyridine}$, C-3, C-5), 51.7 (1C, CH$_3$), 39.8 (1C, CH$_2$-5), 33.6 (1C, CH$_2$-1), 32.9 (2C, CH$_2$Br), 28.8 (1C, CH$_2$-4), 26.1 (1C, CH$_2$-3), 24.0 (1C, CH$_2$-2).

4.5. 6-(2,6-bis(Bromomethyl)isonicotinamido)hexanoic acid (20)

Compound 20 is prepared from 19 (216 mg, 0.50 mmol) by general procedure 1 in order to produce 20 (201 mg, 96%) in the form of an off-white solid.

HRMS: m/z calculated: 420.9684 [M+H]+, found: 420.9748.

$^1$H NMR (300 MHz, DMSO-d$_6$): δ(ppm) 12.01 (s, 1H, COOH), 8.83 (t, J=6.2 Hz, 1H, NH), 7.84 (s, 2H, H$_{arom}$), 4.74 (s, 4H, CH$_2$Br), 3.6 (dd, J=12.6, 6.2 Hz, 2H, CH$_2$-5), 2.21 (t, J=7.3 Hz, 2H, CH$_2$-1), 1.67-1.43 (m, 4H, CH$_2$-2, CH$_2$-4), 1.54-1.34 (dd, J=8.2, 4.6 Hz, 2H, CH$_2$-3).

$^{13}$C NMR (75 MHz, DMSO-d$_6$): δ(ppm) 174.9 (1C, COOH), 164.3 (1C, CONH), 158.0 (2C$_{pyridine}$, C—CH$_2$Br), 144.6 (1C$_{pyridine}$, C—CONH), 121.3 (2C$_{pyridine}$, CH), 39.5

(1C, CH$_2$-5), 34.6 (2C, CH$_2$Br), 34.0 (1C, CH$_2$-1), 29.0 (1C, CH$_2$-4), 26.4 (1C, CH$_2$-3), 24.7 (1C, CH$_2$-2).

4.6. 4-Nitrophenyl 6-(2,6-bis(bromomethyl)isonicotinamido)hexanoate (21)

Under argon at ambient temperature, the acid 20 (70 mg, 0.17 mmol) is dissolved in anhydrous CH$_2$Cl$_2$ (2.1 mL), and DMAP in catalytic quantities, p-nitrophenol (30 mg, 1.3 eq) and DCC (45 mg, 1.3 eq) are added successively to this mixture. The reaction mixture is stirred for 16 hours at ambient temperature under an argon atmosphere, and then filtered. The filtrate is concentrated under reduced pressure and the crude product is purified by flash chromatography in a gradient of cyclohexane at 40% of EtOAc in cyclohexane in order to produce 21 in the form of a pale yellow solid (56 mg, 62%). The product is verified by $^1$H NMR and is used directly for the next step.

HRMS: m/z calculated: 541.9848 [M+M]$^+$, found: 541.9918.

$^1$H NMR (300 MHz, CDCl$_3$): δ(ppm) 8.34-8.21 (m, 2H, H$_{arom}$ PNP), 7.67 (s, 2H, H$_{arom\ pyridine}$), 7.35-7.18 (m, 2H, H$_{arom\ PNP}$), 6.29 (s, 1H, NH), 4.56 (s, 4H, CH$_2$Br), 3.52 (dd, J=13.0, 7.0 Hz, 1H, CH$_2$-5), 2.66 (t, J=7.0 Hz, 1H, CH$_2$-1), 1.91-1.45 (m, 6H, CH$_2$-2, CH$_2$-3, CH$_2$-4).

4.7. 6-(2,6-bis(Bromomethyl)isonicotinamido)hexanamide-Val-Cit-PAB-OH (22)

4-Nitrophenyl 6-(2,6-bis(bromomethyl)isonicotinamido) hexanoate 21 (56 mg, 0.10 mmol) is dissolved in 2.0 mL of DMF under an argon atmosphere at ambient temperature. After 5 min, H-Val-Cit-PAB-OH (20 mg, 0.05 mmol) is added, and the reaction mixture is stirred for 5 h. The DMF is then removed by lyophilization, and the crude product is purified by flash chromatography in a DCM gradient at 10% of MeOH in DCM in order to produce 22 in the form of a pale yellow solid (8.5 mg, 20%). The product is verified by $^1$H NMR and is used directly for the next step.

HRMS: m/z calculated: 781.1798 [M+M]+, found: 782.1873.

$^1$H NMR (300 MHz, DMSO-d$_6$): δ(ppm) 9.90 (s, 1H, NH PAB), 8.83 (d, J=5.7 Hz, 1H, CONH Cit), 8.07 (d, J=7.5 Hz, 1H, CONH Val), 7.84 (s, 4H, 2CH$_{pyridine}$), 7.54, 7.22 (2d, J=8.5 Hz, 4H, Ar PAB), 5.98 (br t, J=5.7 Hz, 1H, NH Cit), 5.42 (br s, 2H, NH$_2$ Cit), 5.11 (br s, 1H, OH PAB), 4.73 (s, 4H, 2×CH$_2$Br), 4.48-4.31 (m, 3H, CH$_2$ PAB, H$_α$ Cit), 4.19 (dd, J=7.0 Hz, J=8.5 Hz, 1H, H$_α$ Val), 3.48-3.12 (water, CH$_2$-5), 3.06-2.89 (m, 2H, NCH$_2$ Cit), 2.18 (dd, J=14.5, 6.5 Hz, 2H, CH$_2$-1), 2.04-1.86 (m, 1H, H$_β$ Val), 1.79-1.21 (m, 10H, CH$_2$CH$_2$ Cit, NCH$_2$CH$_2$CH$_2$CH$_2$), 0.83 (dd, J=8.9, 6.8 Hz, 6H, CH$_3$ Val).

4.8. Methyl hydrochloride 6 aminohexanoate (23)

Under an argon atmosphere at 0° C., SOCl$_2$ (1.22 mL, 16.7 mmol) is added slowly to MeOH (10 ml) and the reaction mixture is stirred for 20 min. 6-Aminocaproic acid (1.00 g, 7.6 mmol) is added to this solution at 0° C., and the mixture is stirred for 3.5 h. The volatiles are removed under reduced pressure, and the residue is recrystallized from heptane/EtOAc/MeOH mixture in order to obtain the desired ester 23 (1.36 g) in a quantitative yield.

$^1$H NMR (300 MHz, CDCl$_3$): δ(ppm) 7.84 (s, 1H, NH), 3.58 (s, 3H, OCH$_3$), 2.85-2.65 (m, 2H, CH$_2$-1), 2.30 (t, J=7.3 Hz, 2H, CH$_2$-1), 1.65-1.36 (m, 4H, CH$_2$-2, CH$_2$-4), 1.31 (ddd, J=11.9, 7.3, 2.3 Hz, 2H, CH$_2$-3).

Example 5: Bioconjugation—Reconstruction of the Disulphide Bridges 5.1. General Procedure 4 for Bioconjugation (Illustrated in FIG. 15)

A solution of the desired antibody is taken. The interchain disulphide bridges are reduced by TCEP (verified by RP-HPLC), then a solution of the appropriate linker is added. After a suitable reaction time (disappearance of the light and heavy chains and reconstruction of the disulphide bridges are monitored by RP-HPLC), the modified crude antibody is purified on columns of Sephadex PD-10.

5.2. TRASTUZUMAB-(maldiBr-linker7)$_4$ 24

Trastuzumab is reduced and then modified according to general procedure 4, using the noncleavable linker 7, 3,4-dibromomaleimide at 37° C. for 1 h:

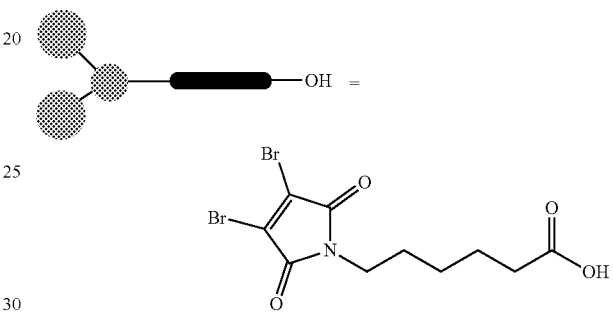

A solution of TCEP (20 eq) in PBS buffer is added to a solution of trastuzumab. A fraction is taken for analysis, to confirm rupture of the disulphide bridges. The mixture is stirred for 15 minutes, then a solution of 6-(3,4-dibromomaleimido)hexanoic acid (20 eq) in DMSO is added. The reaction mixture is stirred for 30 minutes, and then analyzed by RP-HPLC (FIG. 7).

MALDI-TOF mass analysis (FIG. 2) confirms that the reaction mixture (green) contains at 89%, the species resulting from grafting of 4 linkers 6-(3,4-dibromomaleimido) hexanoic acid on the antibody; the grafting average is 4.0.

5.3. TRASTUZUMAB-(maldiBr-linker8)$_4$ 25

Trastuzumab is reduced and then modified according to general procedure 4, using the cleavable linker 8, 3,4-dibromomaleimide at 35° C. for 1 h:

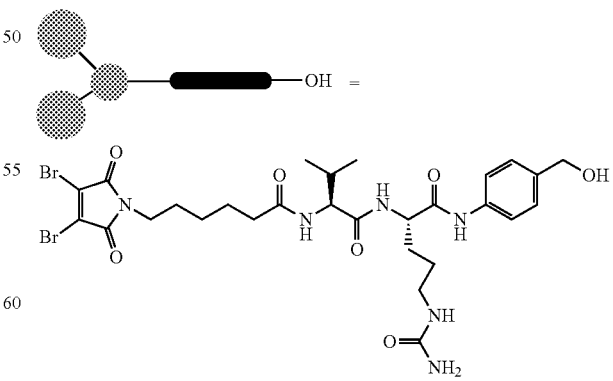

A solution of TCEP (20 eq) in PBS buffer is added to a solution of trastuzumab. The mixture is stirred for 15 minutes, and then a solution of 6-(3,4-dibromomaleimido)

hexanamide-Val-Cit-PAB-OH (20 eq) in DMSO is added. The reaction mixture is stirred for 30 minutes, and then, after purification on a PD-10 column to remove the chemical reagents, the mixture is analyzed by RP-HPLC (FIG. 8), and by HIC-HPLC (FIG. 5).

5.4. TRASTUZUMAB-(maldiSPh-linker26)$_4$ 27

Linker 26 is synthesized in a manner similar to that of WO2013132268, for purposes of comparison between reconstruction of the disulphide bridges using linker 8 dibromomaleimide or linker 26 dithiophenylmaleimide.

Trastuzumab is reduced and then modified according to general procedure 4, using the cleavable linker 8, 3,4-dithiophenylmaleimide at 41° C. for 48 h:

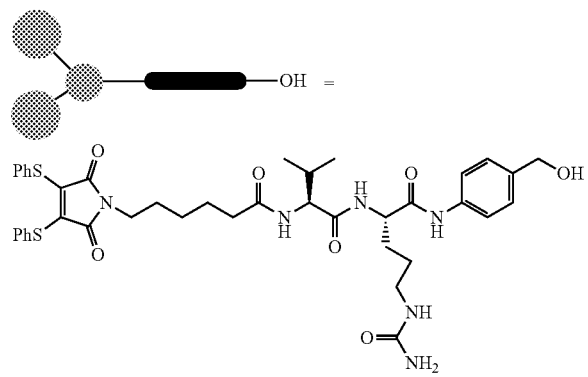

The reaction mixture is then analyzed by RP-HPLC (FIG. 9).

5.5. TRASTUZUMAB-(PydiMediBr-linker20)$_4$ 28

Trastuzumab is reduced and then modified according to general procedure 4, using the non-cleavable linker 20, 6-(2,6-bis(bromomethyl)isonicotinamido) hexanoic acid at 41° C. for 24 h:

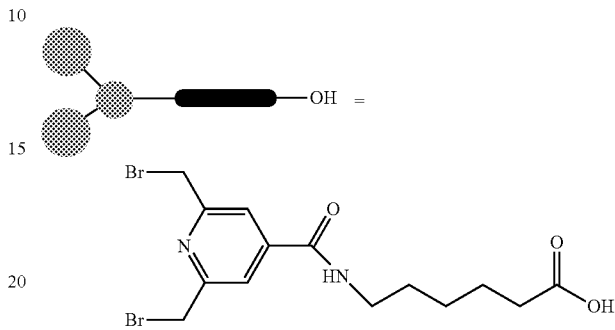

The reaction mixture is then analyzed by RP-HPLC (FIG. 10).

5.6. TRASTUZUMAB-(PydiMediBr-linker22)$_4$ 29

Trastuzumab is reduced and then modified according to general procedure 4, using the cleavable linker 22, 6-(2,6-bis(bromomethyl)isonicotinamido)hexanamide-Val-Cit-PAB-OH at 41° C. for 24 h:

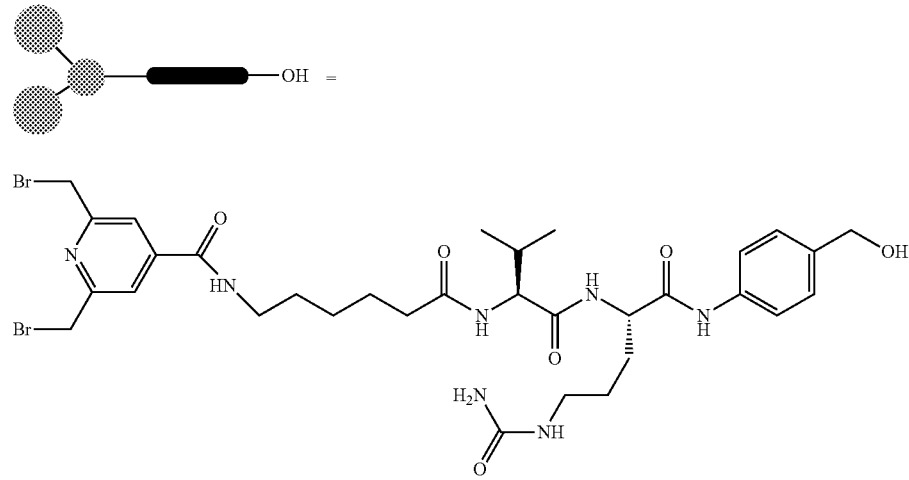

The reaction mixture is then analyzed by RP-HPLC (FIG. 11).

5.7. TRASTUZUMAB-(PhdiMediBr-linker15)$_4$ 30

Trastuzumab is reduced and then modified according to general procedure 4, using the cleavable linker 15, 6-(3,5-bis(bromomethyl)benzamido)hexanamide-Val-Cit-PAB-OH at 41° C. for 72 h:

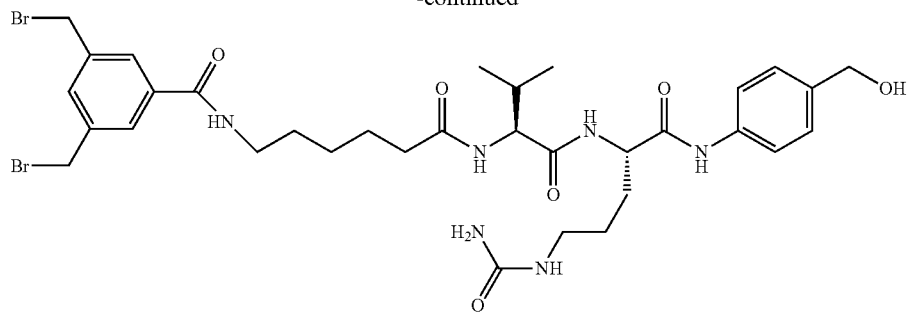

The reaction mixture is then analyzed by RP-HPLC (FIG. 12).

5.8. RITUXIMAB-(maldiBr-linker7)₄ 31

Rituximab is reduced and then modified according to general procedure 4, using the non-cleavable linker 7 at 37° C. for 1 h:

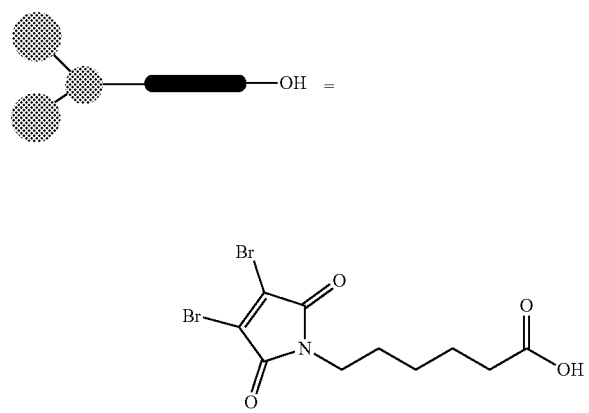

The reaction mixture is then analyzed by RP-HPLC (FIG. 13).

5.9. TRASTUZUMAB-(maldiBr-linker9-MMAE)₄ 32

Trastuzumab is reduced and then modified according to general procedure 4, using the cleavable linker 9-MMAE, 6-(3,4-dibromomaleimido)hexanamide-Val-Cit-PAB-MMAE at 37° C. for 24 h:

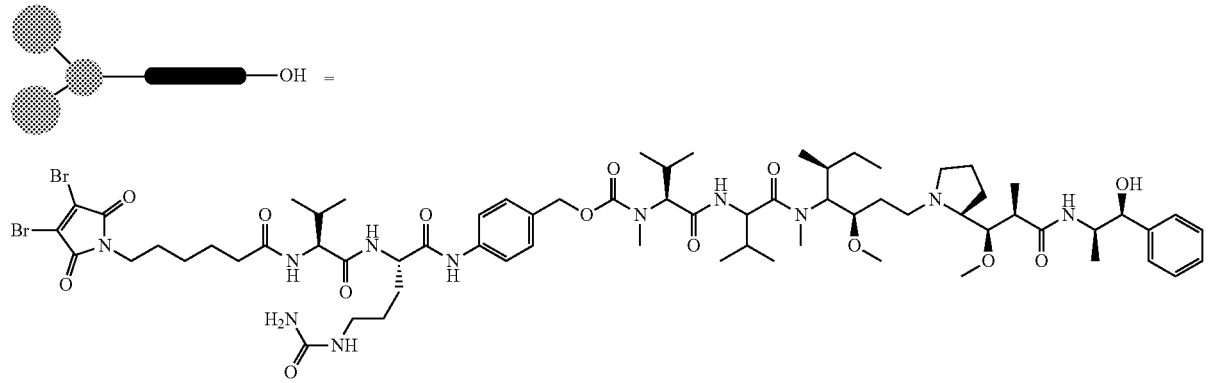

The reaction mixture is then analyzed by RP-HPLC (FIG. 14).

5.10. Additional experimental data for analytical data a—RP-HPLC

The ADCs were analyzed under denaturing and reducing conditions, with an AERIS WIDEPORE 3.6 μM XB-C8 column (250×4.6 mm). The flow rate was 1 mL/min, furnace temperature of 80° C., with a quantity injected of 20 μL per sample. Regarding the method of elution: with two solvents: A was 0.05% trifluoroacetic acid in water and B: 0.04% trifluoroacetic acid in acetonitrile. The method was as follows: 25% B isocratic for 3 min, a linear gradient of 25 min from 25 to 50% B, a linear gradient of 2 min from 50 to 95% B, a linear gradient of 1 min from 95 to 25% B, then 25% B isocratic for 8 min.

b—HIC-HPLC

The ADCs were analyzed under non-denaturing conditions, with a TOSOH BIOSCIENCE 2.5 μM T SKgel butyl-NPR column (100×4.6 mm). The flow rate was 1 mL/min, furnace temperature of 80° C., with an injected quantity of 30 μL per sample. Regarding the method of elution with two solvents: A: 1.5 M $(NH_4)_2SO_4$ in 50 mM PBS phosphate buffer (pH 7) and B: 50 mM PBS phosphate buffer/iProH mixture: 80/20. The method was as follows: a linear gradient of 44 min from 0% B to 80% B, then a linear gradient of 1 min from 80 to 0% B, then 0% B isocratic for 10 min.

The invention claimed is:

1. A method for treating a tumor, comprising a step of administering a product of formula IB2 to a subject in need thereof,

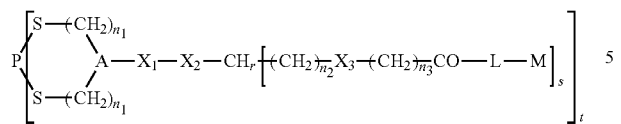
(IB2)

wherein
A is an aryl or a cycloalkyl radical, wherein said aryl or cycloalkyl radical is a carbocycle or a heterocycle, or
A is
a

group, a

group or a

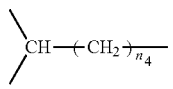

group;

$X_1$ is a C=O or an NH group or a single bond;
$X_2$ is an NH group or a C=O or a single bond;
$X_3$ is an oxygen or a single bond;
s is equal to 1, 2 or 3,
r is equal to 0, 1 or 2, wherein r+s is equal to 3;
$n_1$ is an integer equal to 0 or 1; $n_2$ is an integer equal to 1, 2 or 3 and $n_3$ is an integer equal to 1, 2 or 3;
$n_4$ is an integer equal to 1, 2, 3 or 4;
L is a linker;
M is a cytotoxic drug selected from a chemotherapeutic agent or a toxin;
P is a protein comprising at least one disulphide bridge; and
t is an integer from 1 to 15.

2. The method of claim 1, wherein M is monomethyl auristatin E or monomethyl auristatin F.

3. The method of claim 1, wherein the

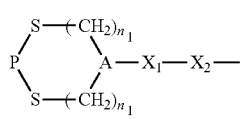

group is selected from

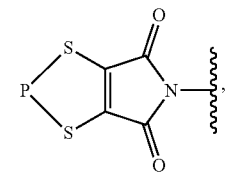

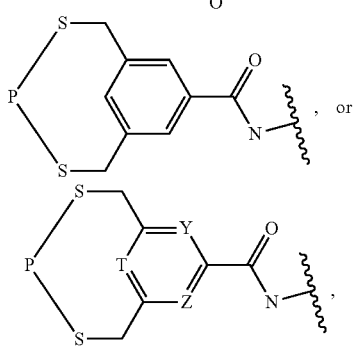

wherein each of T, Y and Z are independently carbon or nitrogen.

4. The method of claim 3, wherein T is a nitrogen atom, and Y and Z represent CH.

5. The method of claim 1, wherein -L-M corresponds to general formula III, IIIa or IIIb:

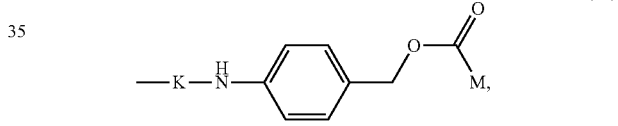

wherein:
K is a

radical, wherein the

radical is a sequence of $n_5$ amino acids, wherein said $n_5$ amino acids are identical or different, natural or non-natural, or
  a hydrazino radical optionally coupled to the

radical, or
  a saccharide group;
X is a hydrogen or an $NO_2$ group,
Y is a

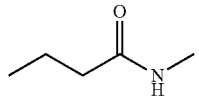

chain or a single bond or a spacer, optionally interrupted by one or more oxygen, sulfur or nitrogen atoms, and
  $n_5$ is an integer from 1 to 6.

6. The method of claim 5, wherein the saccharide group is selected from a beta-glucuronic acid, a beta-D-galactose, a beta-D-glucose, an alpha-D-mannose, an N-acetyl-D-glucosaminyl, an N-acetyl-D-galactosaminyl, a D-glucuronyl, an L-iduronyl, a D-glucopyranosyl, a D-galactopyranosyl, a D-mannopyranosyl or L-fucopyranosyl.

7. The method of claim 5, wherein the spacer is selected from a linear or branched alkyl radical having from 1 to 30 carbon atoms, optionally interrupted by one or more oxygen, sulphur or nitrogen atoms.

8. The method of claim 5, wherein the spacer is polyethylene glycol.

9. The method of claim 5, wherein $n_5$ in the

radical is an integer from 1-5.

10. The method of claim 9, wherein the integer is 2 or 3.

11. The method of claim 5, wherein AA in the

radical is a valine and a citrulline; a phenylalanine and a lysine; a valine and an aspartic acid; a lysine and a methionine; a lysine and an asparagine; a proline and an isoleucine; a proline and a lysine; a valine and a lysine; an alanine and a lysine; a phenylalanine and a lysine; two phenylalanines and a lysine; an alanine, a phenylalanine and a lysine; two arginines; a lysine and an arginine; a glutamic acid, a glycine and an arginine; or two glycines and an arginine.

12. The method of claim 1, wherein M is a chemotherapeutic agent selected from the group consisting of duocarmycin, dolastatins, combretastatin, calicheamicin, N-acetyl-γ-calicheamycin (CMC), maytansine, DM-I, auristatin E, auristatin EB (AEB), auristatin EFP (AEFP), monomethyl auristatin E (MMAE), monomethyl auristatin F (MMAF), tubulysin, disorazole, an epothilone, Paclitaxel, docetaxel, Topotecan, echinomycin, estramustine, cemadotine, eleutherobin, methopterin, actinomycin, daunorubicin, a daunorubicin conjugate, mitomycin C, mitomycin A, vincristine, retinoic acid, camptothecin, SN38, maytansine, DM1, DM4, TK1, amanitin, a pyrrolobenzodiazepine, a pyrrolobenzodiazepine dimer, methotrexate, ilomedine, aspirin, an IMID, lenalidomide and pomalidomide.

13. The method of claim 1, wherein M is a toxin selected from *pseudomonas* exotoxin (PE), deBouganin, Bouganin, diphtheria toxin (DT) and ricin.

14. The method of claim 1, wherein P is an antibody, an antibody fragment or a fusion protein comprising an antibody or an antibody fragment.

15. The method of claim 1, wherein P is an antibody or an antibody fragment, wherein the antibody or fragment is chimeric, humanized, human, monospecific or bispecific.

16. The method of claim 1, wherein P is the antibody fragment selected from the group consisting of Fab, F(ab)'2, Fc, F'c, pFc', ScFv, Fv, Fd, Fabc, diabody, minibody, ScFv-Fc and ScFv-Fv.

17. The method of claim 1, wherein P is an antibody or antibody fragment directed against a tumor antigen.

18. The method of claim 1, wherein P is an antibody or an antibody fragment directed against
  (i) a cluster of differentiation (CD) antigen selected from CD1a, CD3, CD4, CD13, CD19, CD20, CD21, CD22, CD25, CD30, CD31, CD33, CD34, CD37, CD39, CD40, CD44, CD47, CD52, CD56, CD66e, CD70, CD72, CD73, CD74, CD79, CD79b, CD80, CD86, CD117, CD138, CD194, CD205, CD227, CD248 or CD363; or
  (ii) an antigen selected from the group consisting of CA125, G250, GD2, HLA-DRβ, MUC1, VEGF, VEGFA, VEGF-R1/2, TRAIL-R2 (DR5), EpCAM, GPIIb, GPIIIa, TNF alpha, TNFR, TNT, Lewis Y, EGFR, HER-2, HER-3, HER-3 MM-111, HER-4, homodimer or heterodimer between members of the erbbn family, wherein n is an integer between 1 and 4, AXL, Protein F, IgE-Fc, VEGF-A, integrin 4, integrin alpha4beta7, integrin alphaV, C5, IL-6R, IL-6Ralpha, IL12, IL15, IL18, IL23, IL-1beta, IL-1, TPO-R, GPNMB, PSMA, PSA, PAP, PSM, integrin alphav, Cripto, TACSTD2, CEA, Folate receptor 1, Mucin 16, Endothelin Receptor ETB, STEAP1, SLC44A4 (AGS-5), Nectin 4, AGS-16, Guanylyl cyclase C, Mucin 1, EGFRvIII, Mesothelin, IL2R, A33, Can, VEGF-B, VEGF-C, VEGF-D, VEGF-E, VEGFR-1, VEGFR-2, VEGFR-3, TGFbeta, TGFbetaR, FGF, FGF8b, FGFR, PDGF, PDGFR, PDGFRalpha, PDGFRbeta, Ang-1, Ang-2, integrin, α2β1, alpha-v-beta3, alpha-v-beta5, alpha3beta1, alpha6beta4, alpha2beta1, anti-integrin alpha4, RANK-L, BLyS, c-MET, DR, DR10, TCRalpha, beta, ICOS, CTLA-4, CAIX (MN), EphA2, CA6, ovarian CA6, cervical CA6, breast CA6, angiopoietin-2, Cripto, ENPP3, Mesothelin, FOLR1, Nectin-4, TIM-1, Muc-16, Tissue Factor, LIV-1, GM2, alpha5 integrin, TLR-7, PD-1, AFP, CA125 (MUC16), Sialyl Lewis$^Y$, CAMPATH-1, HLA-DR, anti-idiotype, carcinoembryonic antigen (CEA), TAG-72, Folate-binding protein, A33, G250, a ganglioside, Le$^Y$, collagen 4 (collagen IV), collagen 18 (collagen XVIII), SC6, CA-125, CA19-9, p185$^{HER2}$, de2-7 EGFR, Fibroblast activation protein (FAP), Tenascin, metalloproteinases, Endosialin, Carbonic anhydrase, Galectin 9, Aldolase A, eIFgamma4, Tyrosinase, Galectin 4, HERKV-K10, p53, NY-LU-12, Restin, NY-CO-38, MAGE-1, MAGE-4a, SSX2, NY-ESO-1, SCP-1, HGFR, PTK 7, CCK-4, PDGFR, PTP-LAR, CDCP1, CADM1, IGSF4, Lu, BCAM, CEACAM6, JAM-A, PTGFRN (CD9P-1), MCAM, MUC18, MCP, EMMPRIN, TfR, TRAILR2, C1qR, hTERT, Survivin, MDM2, CYP1B1, Melan-A, MART-1, MART-2, Melanosomal proteins, gp100, neo-PAP, CDC27, MAGEs, WT1, MUM-1, MUM-2, MUM-3, BRAF, TPI, fibronectin, K-ras, beta-catenin, CDK4, caspase-8, $p14^{ARF}$, $p16^{INK4a}$, bcr-ab1, SYT-SSX, TRP-1, TRP-2, GnT-V, tyrosinase, FGF5, TEL-AML1, proteinase 3, HER2/neu, AFP, MUC-1, EBV-EBNA, HTLV-1 tax, HPV16-E7, mutated HLA-A2, HA1, SART3, GnT-V, CEACAM5, AGS-16, GPNMB, ESAT-6, RANK, CanAg, fibrin, TF, PRAME, CA19-9, CA50, CA125, CA195, CAM17.1/WGA, AFP, beta-MG, DU-PAN2, HE4, b-2 microglobulin, transferrin, transthyretin, ApoA1, TROP-2, CTLA-4, GITR, PD-1, PD-L1, c-KIT, CD11b-CD18 integrin heterodimer, DNA/Histon H1, Folate, EpCAM, Tenascin-c, Extracellular Matrix (ECM), fibrinogen, SV40 large T antigen, SC6-Ag, SC—Ag, death receptor 4 (DR4), DR5, ESA, mucin, hPAM4, hRS7, HLA-DR, CCR4, PECAM, thrombomodulin, Tn, cathepsin D, TYRO-3, MER or a PF4/heparin complex.

19. The method of claim 18, wherein TACSTD2 is TROP2 and/or EGP1, wherein the ganglioside is GD2, GD3 and/or GM2, or wherein the ECM is proteoglycan and/or fibronectin.

20. The method of claim 1, where the tumor is a colorectal cancer, a hepatocarcinoma, a lung cancer, a pancreatic cancer, a breast cancer, a liver cancer, a head and neck cancer, a Castleman disease tumor, a thyroid cancer, a medulloblastoma, a glioblastoma multiforme, a glioma, a sarcoma, an anaplastic astrocytoma, a kidney cancer, a stomach cancer, malignant ascites, a metastatic prostate cancer, a non-metastatic prostate tumor, a solid tumor, a leukemia, a melanoma, a myeloma, or a lymphoma.

21. The method of claim 20, wherein the breast cancer is a triple-negative breast cancer or a metastatic breast cancer, wherein the leukemia is acute myeloid leukemia or chronic lymphocytic leukemia, wherein the lymphoma is mantle cell lymphoma, Hodgkin's lymphoma, non-Hodgkin's lymphoma or follicular lymphoma, wherein the myeloma is multiple myeloma, wherein the lung cancer is not a small cell lung cancer or wherein the colorectal cancer is a K-RAS mutated colorectal cancer.

22. The method of claim 20, wherein the lung cancer is a small cell lung cancer.

23. The method of claim 20, wherein the lung cancer is not a small cell lung cancer.

24. The method of claim 1, wherein t is an integer from 1 to 13.

25. The method of claim 1, wherein t is an integer from 1 to 6.

* * * * *